US012440471B2

(12) United States Patent
Acharya et al.

(10) Patent No.: US 12,440,471 B2
(45) Date of Patent: Oct. 14, 2025

(54) COMPOSITIONS AND METHODS FOR THE TREATMENT OF BRONCHOPULMONARY DYSPLASIA (BPD) AND BPD-ASSOCIATED PULMONARY HYPERTENSION

(71) Applicant: AyuVis Research, Inc., Fort Worth, TX (US)

(72) Inventors: Suchismita Acharya, Grapevine, TX (US); Pragnya Das, Secane, PA (US)

(73) Assignee: AyuVis Research, Inc., Fort Worth, TX (US)

( * ) Notice: Subject to any disclaimer, the term of this patent is extended or adjusted under 35 U.S.C. 154(b) by 0 days.

(21) Appl. No.: 17/873,453

(22) Filed: Jul. 26, 2022

(65) Prior Publication Data

US 2023/0097886 A1 Mar. 30, 2023

Related U.S. Application Data

(60) Provisional application No. 63/227,819, filed on Jul. 30, 2021.

(51) Int. Cl.
*A61K 31/351* (2006.01)
*A61K 9/00* (2006.01)
*A61K 45/06* (2006.01)
*A61P 29/00* (2006.01)

(52) U.S. Cl.
CPC .......... *A61K 31/351* (2013.01); *A61K 9/0078* (2013.01); *A61K 45/06* (2013.01); *A61P 29/00* (2018.01)

(58) Field of Classification Search
CPC ................ A61K 31/351; A61K 31/702; A61K 31/7034; A61K 31/7042; A61K 31/7052; A61K 9/0078; A61P 11/08; A61P 29/00; A61P 11/00
See application file for complete search history.

(56) References Cited

U.S. PATENT DOCUMENTS

| | | | |
|---|---|---|---|
| 7,897,577 B2 | 3/2011 | Johansson et al. | |
| 2005/0255048 A1 | 11/2005 | Hirsh et al. | |
| 2017/0281667 A1 | 10/2017 | Acharya et al. | |
| 2018/0177832 A1 | 6/2018 | Fabbri et al. | |
| 2020/0022995 A1 | 1/2020 | Acharya et al. | |

FOREIGN PATENT DOCUMENTS

| | | | |
|---|---|---|---|
| CN | 112638414 A | 4/2021 | |
| WO | WO-2006074296 A1 * | 7/2006 | ............. A61K 31/00 |
| WO | 2020/010090 | 1/2020 | |

OTHER PUBLICATIONS

Abdullah, O. M., et al., (2016). "Diffusion tensor imaging and histology of developing hearts." NMR Biomed 29(10): 1338-1349.

Aghai, Z. H., et al., (2008). "Angiopoietin 2 concentrations in infants developing bronchopulmonary dysplasia: attenuation by dexamethasone." J Perinatol 28(2): 149-155.

Albertine, K. H. (2012). "Brain injury in chronically ventilated preterm neonates: collateral damage related to ventilation strategy." Clin Perinatol 39(3): 727-740.

Albertine, K. H., et al., (1999). "Chronic lung injury in preterm lambs. Disordered respiratory tract development." Am J Respir Crit Care Med 159(3): 945-958.

Albertine, K. H., et al., (2010). "Chronic lung disease in preterm lambs: effect of daily vitamin A treatment on alveolarization." Am J Physiol Lung Cell Mol Physiol 299(1): L59-72.

Alejandre-Alcazar, M. A., et al., (2007). "Hyperoxia modulates TGF-beta/BMP signaling in a mouse model of bronchopulmonary dysplasia." Am J Physiol Lung Cell Mol Physiol 292(2): L537-549.

Bassler, D., et al., (2010). "The Neonatal European Study of Inhaled Steroids (Neurosis): an eu-funded international randomised controlled trial in preterm infants." Neonatology 97(1): 52-55.

Bassler, D., et al., (2018). "Long-Term Effects of Inhaled Budesonide for Bronchopulmonary Dysplasia." N Engl J Med 378(2): 148-157.

Bhandari, V. (2002). "Developmental differences in the role of interleukins in hyperoxic lung injury in animal models." Front Biosci 7: d1624-1633.

Bhandari, V. (2014). "Drug therapy trials for the prevention of bronchopulmonary dysplasia: current and future targets." Front Pediatr 2: 76.

Bhandari, V., et al., (2006). "Hyperoxia causes angiopoietin 2-mediated acute lung injury and necrotic cell death." Nat Med 12(11): 1286-1293.

Bhandari, V., et al., (2008). "Developmental regulation of NO-mediated VEGF-induced effects in the lung." Am J Respir Cell Mol Biol 39(4): 420-430.

Chen, X., et al., (2017). "Bone Morphogenetic Protein 9 Protects against Neonatal Hyperoxia-Induced Impairment of Alveolarization and Pulmonary Inflammation." Front Physiol 8: 486.

(Continued)

*Primary Examiner* — Sarah Pihonak
(74) *Attorney, Agent, or Firm* — Edwin S. Flores; Daniel J. Chalker; Chalker Flores LLP

(57) ABSTRACT

The present invention includes a composition and method for preventing at least one of: neonatal lung injury, bronchopulmonary dysplasia (BPD), or BPD-associated pulmonary hypertension (BPD-PH) comprising: a compound of formula (I) and variants thereof:

Formula-I

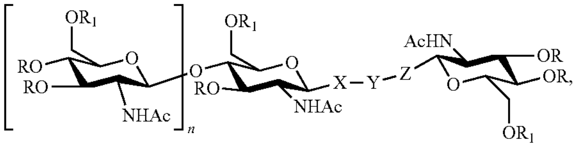

in an amount sufficient to prevent at least one of: neonatal lung injury, bronchopulmonary dysplasia (BPD), or BPD-associated pulmonary hypertension (BPD-PH).

39 Claims, 28 Drawing Sheets

(56) References Cited

OTHER PUBLICATIONS

Curtale, G., et al., (2013). "Negative regulation of Toll-like receptor 4 signaling by IL-10-dependent microRNA-146b." Proc Natl Acad Sci U S A 110(28): 11499-11504.
Dahl, M. J., et al., (2018). "Former-preterm lambs have persistent alveolar simplification at 2 and 5 months corrected postnatal age." Am J Physiol Lung Cell Mol Physiol 315(5): L816-I833.
Das, P., et al., (2019) "Novel Chitohexaose Analog Protects Young and Aged mice from CLP Induced Polymicrobial Sepsis." Scientific Report, 9(1):2904.
Das, P., et al., (2020). "Chitin Analog AVR-25 Prevents Experimental Bronchopulmonary Dysplasia." J Pediatr Intensive Care 9(3): 225-232.
Das, P., et al., (2020). "Small Molecule Inhibitor Adjuvant Surfactant Therapy Attenuates Ventilator- and Hyperoxia-Induced Lung Injury in Preterm Rabbits." Front Physiol 11: 266.
Filippone, M., et al., (2019). "Update on Postnatal Corticosteroids to Prevent or Treat Bronchopulmonary Dysplasia." Am J Perinatol 36(S 02): S58-S62.
Gilfillan, M., et al., (2020). "Inhibition of microRNA-451 is associated with increased expression of Macrophage Migration Inhibitory Factor and mitgation of the cardio-pulmonary phenotype in a murine model of Bronchopulmonary Dysplasia." Respir Res 21(1): 92.
Hansmann, G., et al., (2021). "Pulmonary hypertension in bronchopulmonary dysplasia." Pediatr Res 89(3): 446-455.
Horbar, J. D., et al., (2017). "Variation in Performance of Neonatal Intensive Care Units in the United States." JAMA Pediatr 171(3): e164396.
Joss-Moore, L. A., et al., (2010). "Epigenetics and fetal adaptation to perinatal events: diversity through fidelity." J Anim Sci 88(13 Suppl): E216-222.
Jung, Y. H., et al., (2019). "Respiratory severity score as a predictive factor for severe bronchopulmonary dysplasia or death in extremely preterm infants." BMC Pediatrics 19(1): 121.
Kim, H. M., et al., (2007). "Crystal Structure of the TLR4-MD-2 Complex with Bound Endotoxin Antagonist Eritoran." Cell 130(5): 906-917.
Lavoie, P., et al., (2010) "Profound Lack of Interleukin (IL)-12/IL-23p40 in Neonates Born Early in Gestation Is Associated with an Increased Risk of Sepsis," The Journal of Infectious Diseases, 202(11):1754-1763.
Leary, S., et al., (2019). "Genetic Strain and Sex Differences in a Hyperoxia-Induced Mouse Model of Varying Severity of Bronchopulmonary Dysplasia." Am J Pathol 189(5): 999-1014.
Li, N., et al., (2009). "Liposome coated with low molecular weight chitosan and its potential use in ocular drug delivery." International Journal of Pharmaceutics 379(1): 131-138.
Lui, K., et al., (2019). "Trends in Outcomes for Neonates Born Very Preterm and Very Low Birth Weight in 11 High-Income Countries." J Pediatr 215: 32-40 e14.
Meau-Petit, V., et al., (2013). "[Bronchopulmonary dysplasia-associated pulmonary arterial hypertension of very preterm infants]." Arch Pediatr 20(1): 44-53.
Null, D. M., et al., (2014). "High-frequency nasal ventilation for 21 d maintains gas exchange with lower respiratory pressures and promotes alveolarization in preterm lambs." Pediatr Res 75(4): 507-516.
Panda, S. K., et al., (2012). "Chitohexaose activates macrophages by alternate pathway through TLR4 and blocks endotoxemia." PLoS Pathog 8(5): e1002717.
Reyburn, B., M. et al., (2008). "Nasal ventilation alters mesenchymal cell turnover and improves alveolarization in preterm lambs." Am J Respir Crit Care Med 178(4): 407-418.
Sahni, M. and V. Bhandari (2020). "Recent advances in understanding and management of bronchopulmonary dysplasia." F1000Res 9.
Sahni, M., et al., (2020). "Novel biomarkers of bronchopulmonary dysplasia and bronchopulmonary dysplasia- associated pulmonary hypertension." J Perinatol 40(11): 1634-1643.
Shah, D., et al., (2021). "Small Immunomodulatory Molecules as Potential Therapeutics in Experimental Murine Models of Acute Lung Injury (ALI)/Acute Respiratory Distress Syndrome (ARDS)." Int J Mol Sci 22(5).
Speer, C. P. (2006). "Pulmonary inflammation and bronchopulmonary dysplasia." J Perinatol 26 Suppl 1: S57-62; discussion S63-54.
Stenmark, K. R. and S. H. Abman (2005). "Lung vascular development: implications for the pathogenesis of bronchopulmonary dysplasia." Annu Rev Physiol 67: 623-661.
Sun, H., et al., (2013). "A critical regulatory role for macrophage migration inhibitory factor in hyperoxia-induced injury in the developing murine lung." PLoS One 8(4): e60560.
Sun, Y., et al., (2019). "High Neutrophil-to-Lymphocyte Ratio Is an Early Predictor of Bronchopulmonary Dysplasia." Front Pediatr 7: 464.
Sureshbabu, A., et al., (2016). "Inhibition of Regulatory-Associated Protein of Mechanistic Target of Rapamycin Prevents Hyperoxia-Induced Lung Injury by Enhancing Autophagy and Reducing Apoptosis in Neonatal Mice." Am J Respir Cell Mol Biol 55(5): 722-735.
Syed, M., et al., (2017). "Hyperoxia causes miR-34a-mediated injury via angiopoietin-1 in neonatal lungs." Nat Commun 8(1): 1173.
Tam, J. S. Y., et al., (2021). "Toll-like receptor 4 (TLR4) antagonists as potential therapeutics for intestinal inflammation." Indian J Gastroenterol.
Thebaud, B., et al., (2019). "Bronchopulmonary dysplasia." Nat Rev Dis Primers 5(1): 78.
Tolia, V. N., et al., (2014). "The effect of the national shortage of vitamin A on death or chronic lung disease in extremely low-birth-weight infants." JAMA Pediatr 168(11): 1039-1044.
Williams, J., et al., (2003). "Nanoparticle drug delivery system for intravenous delivery of topoisomerase inhibitors." Journal of Controlled Release 91(1-2): 167-172.
Yee, M., et al., (2011). "Neonatal hyperoxia causes pulmonary vascular disease and shortens life span in aging mice." Am J Pathol 178(6): 2601-2610.
Piersigilli, Fiammetta et al. (2016) Biomarkers in neonatology: the new "omics" of bronchopulmonary dysplasia, The Journal of Maternal-Fetal & Neonatal Medicine, 29:11, 1758-1764 [abstract].
International Search Report [ISR/US] PCT/2022/038426 dated Jul. 27, 2022.
Acharya, S. A., et al. "Preclinical Profile of a Novel Immunomodulatory Compound AVR-48 to Prevent Bronchopulmonary Dysplasia." C27. Bronchopulmonary Dysplasia And Congenital Lung Lesions I. American Thoracic Society, 2020. A4647-A4647.
Bhandari, Vineet, et al. "Novel Immunomodulatory Compounds to Prevent Bronchopulmonary Dysplasia." D27. Mechanistic Insights Into Bronchopulmonary Dysplasia. American Thoracic Society, 2019. A6031-A6031.
Shah, Dilip, et al. "Small immunomodulatory molecules as potential therapeutics in experimental murine models of acute lung injury (ALI)/acute respiratory distress syndrome (ARDS)." International journal of molecular sciences 22.5 (2021): 2573.
Das, Pragnya, et al. "Chitin-derived AVR-48 prevents experimental bronchopulmonary dysplasia (BPD) and BPD-associated pulmonary hypertension in newborn mice." International journal of molecular sciences 22.16 (2021): 8547.
Das, Pragnya, et al. "Chitin Analog AVR-25 Prevents Experimental Bronchopulmonary Dysplasia." Journal of pediatric intensive care 9.03 (2020): 225-232.
Supplemental European Search Report, EP 228502142, dated Apr. 22, 2025.

* cited by examiner

Biotin-AVR-48 (BT-AVR-48)

COMPOSITIONS AND METHODS FOR THE TREATMENT OF BRONCHOPULMONARY DYSPLASIA (BPD) AND BPD-ASSOCIATED PULMONARY HYPERTENSION

CROSS-REFERENCE TO RELATED APPLICATIONS

This application claims priority to U.S. Provisional Application Ser. No. 63/227,819, filed Jul. 30, 2021, the entire contents of which are incorporated herein by reference.

STATEMENT OF FEDERALLY FUNDED RESEARCH

This invention was made with government support under R44HD107857 awarded by the National Institute of Health, National Institute for Child Development. The government has certain rights in the invention.

TECHNICAL FIELD OF THE INVENTION

The present invention relates in general to the field of treatments for pulmonary hypertension, and more particularly, to compositions and methods for the prophylactic therapeutic treatment to prevent or treat neonatal lung injury, bronchopulmonary dysplasia (BPD) and BPD-associated pulmonary hypertension (BPD-PH).

INCORPORATION-BY-REFERENCE OF MATERIALS FILED ON COMPACT DISC

None.

BACKGROUND OF THE INVENTION

Without limiting the scope of the invention, its background is described in connection with respiratory distress.

Bronchopulmonary Dysplasia (BPD) is a neonatal condition that occurs in infants born at <28 weeks of gestation and birth weights <1000 grams. The strongest risk factors for BPD are prematurity and low birth weight (Bhandari 2016). Secondary to premature birth, the babies have immature lungs. While affected infants can improve over time due to lung growth, they will suffer from significant morbidity in childhood, extending up to adulthood, due to neurodevelopmental impairment, asthma and emphysematous changes of the lung. While many drugs have been tried to prevent/attenuate BPD (Bhandari 2014, Sahni and Bhandari 2020), no specific and effective treatment is available, and therefore this disease is still associated with high mortality and morbidity (Lui, Lee et al. 2019). Despite improved neonatal care, the number of BPD cases due to this condition have not decreased (Horbar, Edwards et al. 2017), secondary to increased survival of infants of lower gestational ages. Although exogenous surfactant is standard-of-care treatment for respiratory distress syndrome (RDS) in premature neonates, there is no effective prevention or treatment for BPD to date (Bhandari 2014). Use of steroids as anti-inflammatory therapy is partially helpful in minimizing inflammation in BPD; however, in babies administered the drug (either ante- and post-natally via parenteral or inhaled routes), the incidence of BPD is either not decreased or the risk of death and poor neurodevelopmental outcome outweighs the overall benefit. There have been no randomized clinical trials (RCTs) where inhaled budesonide has been used to treat 'established BPD' (Andrews 2020). In the largest RCT on inhaled budesonide (Bassler, Halliday et al. 2010), although there was a significant lowering of the incidence of BPD (Bassler 2017), there was no difference in neurodevelopmental outcomes (Bassler, Shinwell et al. 2018) and significantly increased mortality in the treatment group (Filippone, Nardo et al. 2019).

BPD is a multifactorial clinical syndrome of lung injury that affects normal alveolarization and microvascular development leading to anatomical changes that contribute to abnormal gas exchange and pulmonary mechanics (Thebaud, Goss et al. 2019). This imbalance results in increased cell death and decreased cell proliferation associated with overall lung inflammation that contributes to a BPD phenotype. The alveoli become expanded with simplified alveolar epithelium and disrupted endothelium that interferes with the growth of distal airspace (Stenmark and Abman 2005). The progression towards BPD is an uncertain and unpredictable process, and there are no definitive medications available to date to reduce the risk of the progression of this disease in RCTs (Jensen, Roberts et al. 2020). Trials of using inhaled budesonide, and/or budesonide-surfactant combination or mother's milk or use of intramuscular vitamin A and prophylactic hydrocortisone has resulted in a modest reduction in the rate of BPD, but does not cure the disease (Tolia, Murthy et al. 2014, Jensen, Roberts et al. 2020). A new preclinical meta-analysis has demonstrated the benefits of mesenchymal stromal cell therapy in animal models, while the results of early clinical trials are still pending (Strueby and Thebaud 2018).

BPD-associated pulmonary hypertension (BPD-PH) is a chronic inflammatory co-morbid condition with devastating short- and long-term consequences (Sahni, Yeboah et al. 2020). Infants with BPD are predisposed to abnormal growth of pulmonary vasculature with dysregulated pulmonary vascular density and increased pulmonary vascular resistance, which contributes to BPD-PH. The pathogenesis of BPD-PH is poorly understood and therefore there is less data currently about appropriate therapy. Animal studies and a few clinical studies suggest that medications targeting the nitric oxide (NO) signaling pathway (NO inhalation, oral sildenafil citrate) could be effective treatment for BPD-PH, but they have not been specifically approved for this indication (Meau-Petit, Thouvenin et al. 2013).

Despite these efforts, a need remains for novel compositions and methods to prevent or treat neonatal lung injury, bronchopulmonary dysplasia (BPD) and BPD-associated pulmonary hypertension (BPD-PH).

SUMMARY OF THE INVENTION

In one embodiment, the present invention includes a composition for preventing at least one of: neonatal lung injury, bronchopulmonary dysplasia (BPD), or BPD-associated pulmonary hypertension (BPD-PH) comprising: a compound of formula (I) or stereoisomer, enantiomer, tautomer or a pharmaceutically acceptable salt thereof:

Formula-I

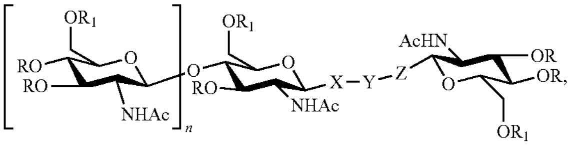

wherein n=0-5; X=NH, O, S, or $CH_2$; Y=Phenyl, a phenyl group substituted with at least one methyl, a phenyl group substituted with at least one nitro, a phenyl group substituted with at least one nitrogen, a phenyl group substituted with at least one boron, aryl, substituted aryl, heteroaryl, four to six membered cycloalkyl, four to six membered heterocycloalkyl; Z=NH, O, S, $CH_2$ or none; R=H, $C(O)R_2$, $SO_2R_2$; $R_1$=H, $C(O)R_2$, $SO_2R_2$; $R_2$=Ethyl, methyl, isopropyl, n-propyl, t-butyl, n-butyl, $NH_2$, $NR_3R_4$, $R_3$, $R_4$=ethyl, methyl, isopropyl, n-propyl, t-butyl, n-butyl, three to six membered cycloalkyl, wherein an amount of the compound is selected to prevent the at least one of neonatal lung injury, bronchopulmonary dysplasia (BPD), or BPD-associated pulmonary hypertension (BPD-PH) comprising. In one aspect, the compound of formula (I) or stereoisomer, enantiomer, tautomer, or a pharmaceutically acceptable salt thereof is formulated for intravenous administration. In another aspect, the composition is formulated into a pharmaceutical composition comprising one or more pharmaceutically acceptable excipients, buffers, or salts. In another aspect, the composition is formulated into a pharmaceutical composition adapted for pulmonary, alveolar, enteral, parenteral, intravenous, topical, or oral administration. In another aspect, the composition is formulated into an aerosol, a nebulizer, or an inhaler. In another aspect, the composition further comprises one or more liposomes, polymers, salts, or buffers. In another aspect, the composition further comprises an additional therapeutic agent selected from the group consisting of corticosteroids, bronchodilators, anticholinergics, vasodilators, diuretics, anti-hypertensive agents, acetazolamide, antibiotics, antivirals, immunosuppressive drugs, and surfactants. In another aspect, the composition is provided in an amount that competitively inhibits inflammation and modulates macrophages to protect lung tissue damage or limit lung tissue injury. In another aspect, the subject is a pediatric or adult human or a pediatric or adult animal. In another aspect, the composition is formulated for a delivery device that is a spray device or a pressurized delivery device. In another aspect, the compound of formula I wherein Z=none. In another aspect, the compound of formula I is:

8

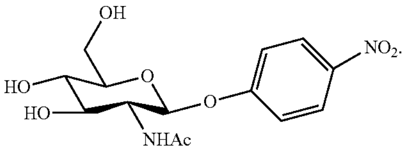

In another aspect, the compound is selected from at least one of:

1

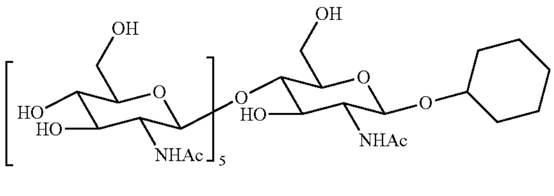

-continued

2

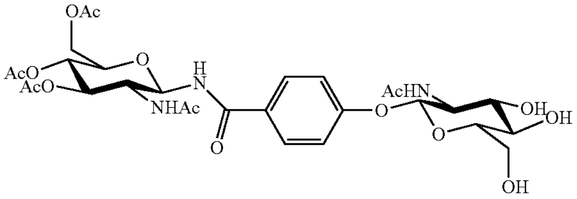

3

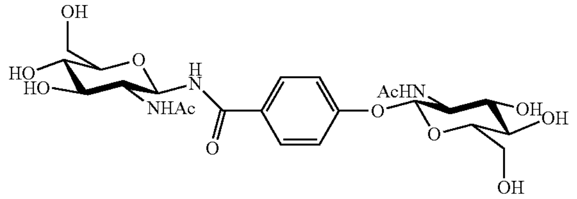

4

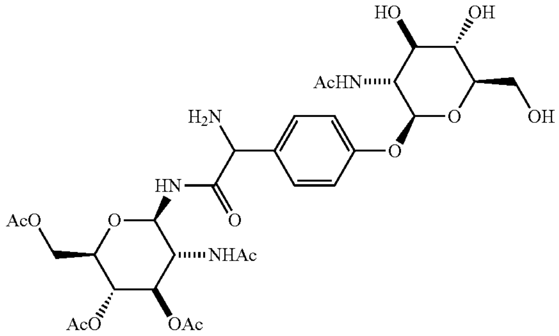

5

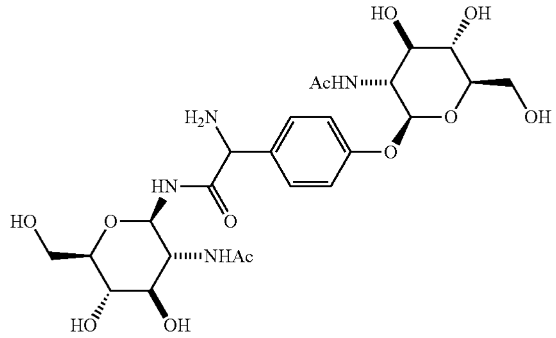

6

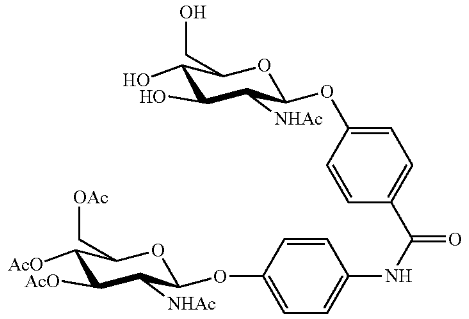

-continued
7
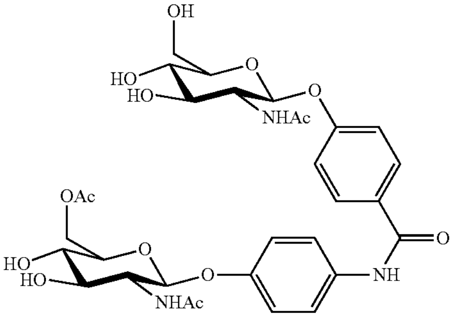
9
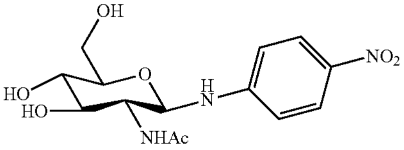
10
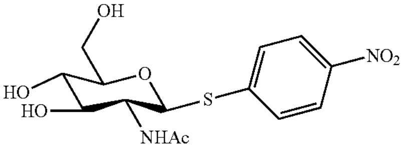
11
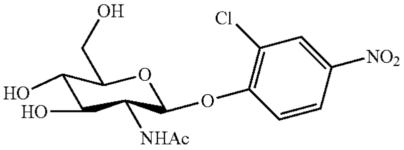
12
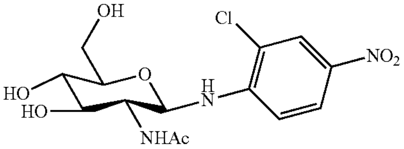
13
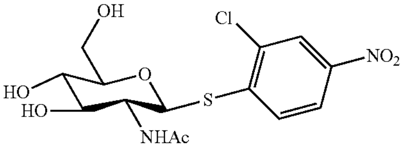
14
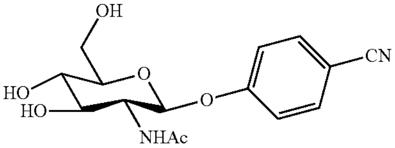
15
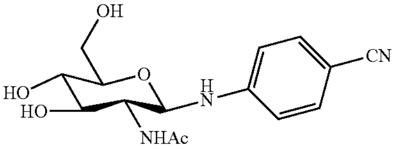
16
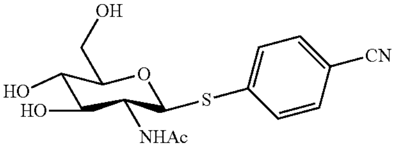
-continued
17
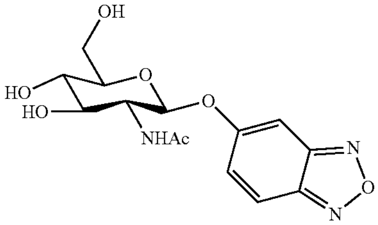
18
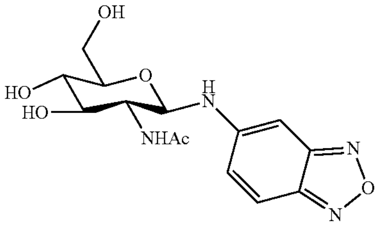
19
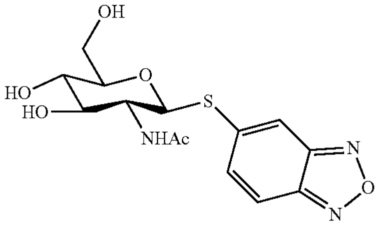
20
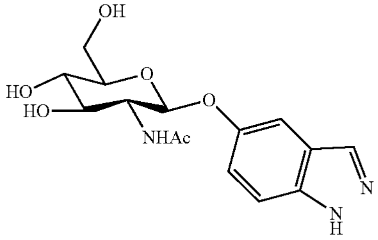
21
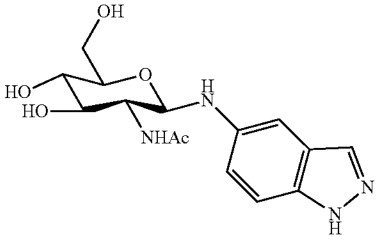
22
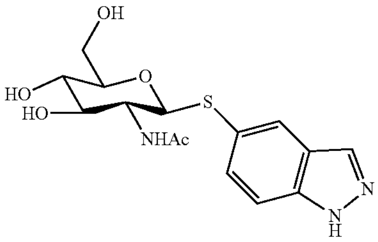

-continued
23
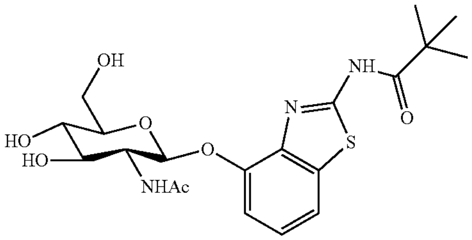
24
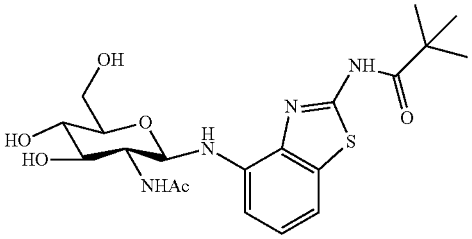
25
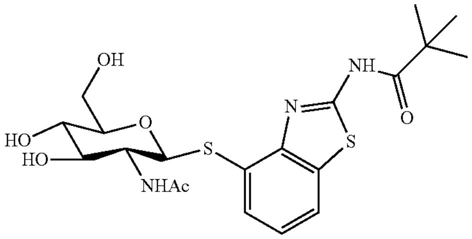
26
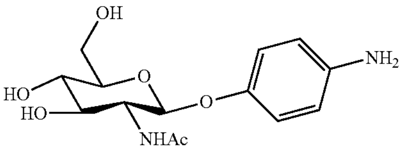
27
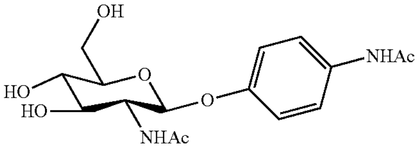
29
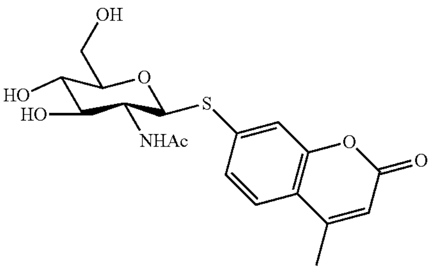
28
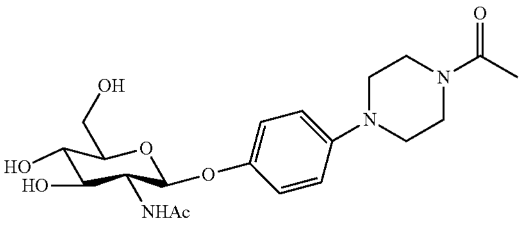
-continued
30
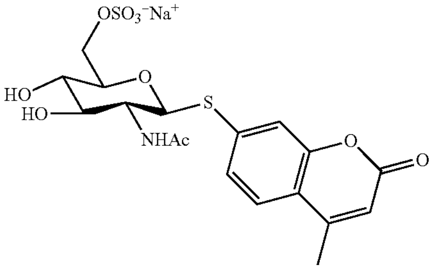
31
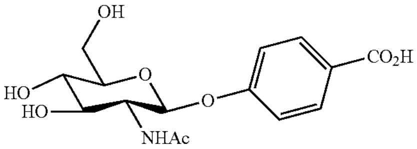
32
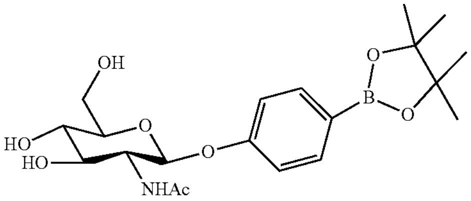
33
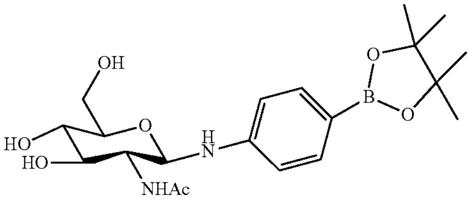
34
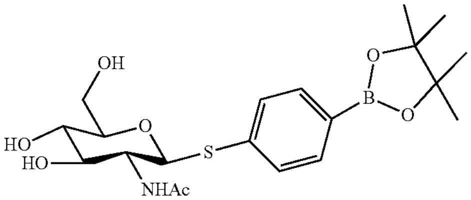
35
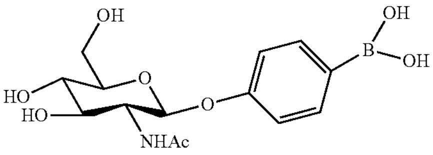
36
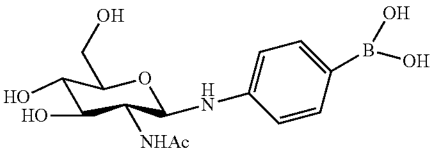
37
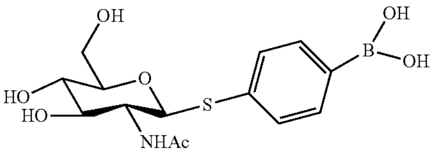

-continued

38

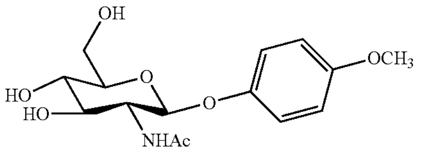

39

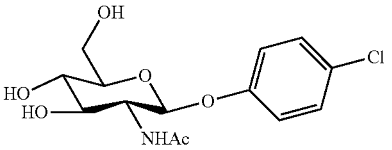

or

40

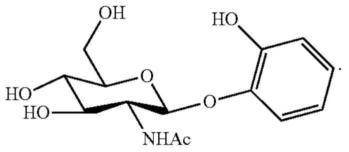

A method for preventing at least one of: neonatal lung injury, bronchopulmonary dysplasia (BPD), or BPD-associated pulmonary hypertension (BPD-PH), comprising: administering to the subject in need thereof a therapeutically effective and synergistic amount of a lung surfactant isolated from a lung extract or a synthetic equivalent thereof; and a compound of formula (I) or stereoisomer, enantiomer, tautomer or a pharmaceutically acceptable salt thereof:

Formula-I

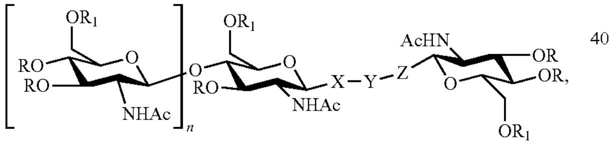

wherein n=0-5; X=NH, O, S, or $CH_2$; Y=Phenyl, a phenyl group substituted with at least one methyl, a phenyl group substituted with at least one nitro, a phenyl group substituted with at least one nitrogen, a phenyl group substituted with at least one boron, aryl, substituted aryl, heteroaryl, four to six membered cycloalkyl, four to six membered heterocycloalkyl; Z=NH, O, S, $CH_2$ or none; R=H, $C(O)R_2$, $SO_2R_2$; $R_1$=H, $C(O)R_2$, $SO_2R_2$; $R_2$=ethyl, methyl, isopropyl, n-propyl, t-butyl, n-butyl, $NH_2$, $NR_3R_4$, $R_3$, $R_4$=ethyl, methyl, isopropyl, n-propyl, t-butyl, n-butyl, three to six membered cycloalkyl, wherein an amount of the compound is selected to prevent the at least one of: neonatal lung injury, bronchopulmonary dysplasia (BPD), or BPD-associated pulmonary hypertension (BPD-PH) comprising. In one aspect, the compound of formula (I) or stereoisomer, enantiomer, tautomer or a pharmaceutically acceptable salt thereof. In another aspect, the composition is formulated into a pharmaceutical composition comprising one or more pharmaceutically acceptable excipients, buffers, or salts. In another aspect, the composition is formulated into a pharmaceutical composition adapted for pulmonary, alveolar, enteral, parenteral, intravenous, topical, or oral administration. In another aspect, the composition is formulated into an aerosol, a nebulizer, or an inhaler. In another aspect, the composition forms an inhalation dosage form. In another aspect, the method further comprises adding one or more liposomes, polymers, salts, or buffers. In another aspect, the method further comprises adding one or more additional therapeutic agent selected from the group consisting of corticosteroids, bronchodilators, anticholinergics, vasodilators, diuretics, anti-hypertensive agents, acetazolamide, antibiotics, antivirals, immunosuppressive drugs, and surfactants. In another aspect, the composition is provided in an amount that competitively inhibits inflammation and modulates macrophages to protect lung tissue damage or limit lung tissue injury. In another aspect, the subject is a pediatric or adult human or a pediatric or adult animal. In another aspect, the composition is formulated for a delivery device that is a spray device or a pressurized delivery device. In another aspect, the compound of formula I wherein Z=none. In another aspect, the compound of formula I is:

8

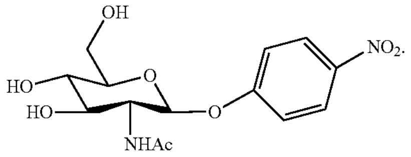

In another aspect, the compound is selected from at least one of:

1

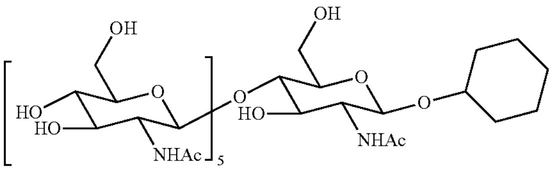

2

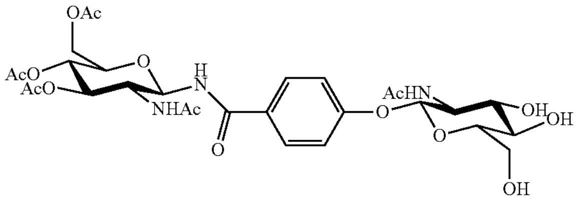

3

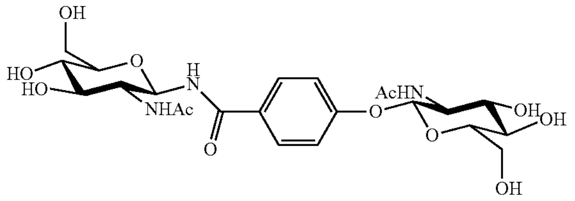

-continued
4
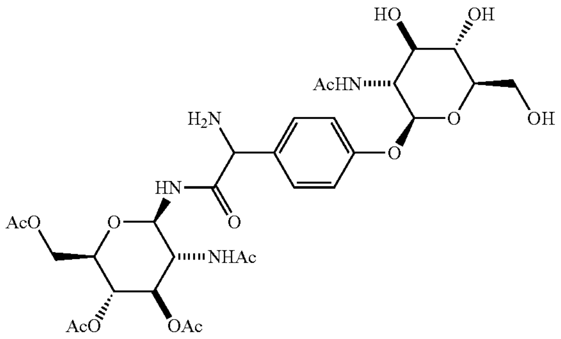
5
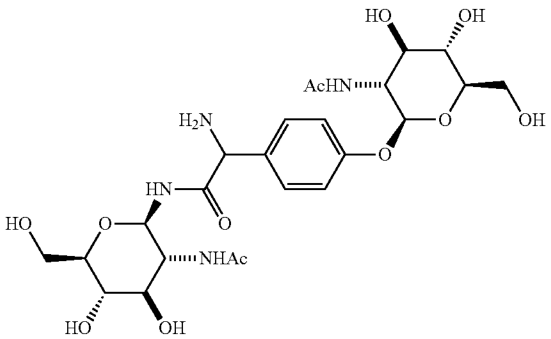
6
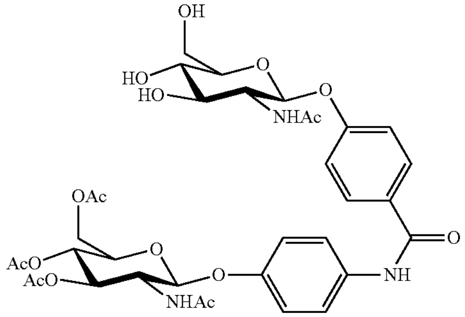
7
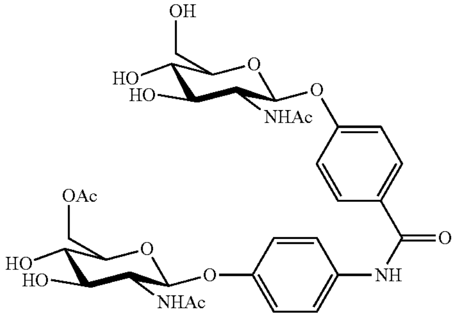
9
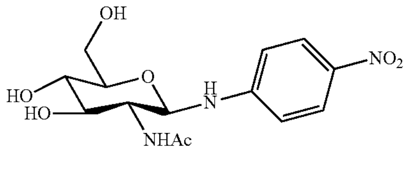
-continued
10
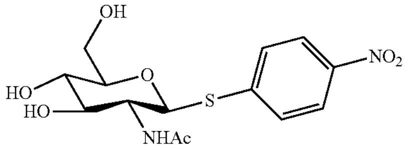
11
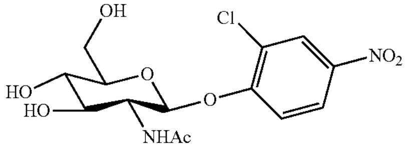
12
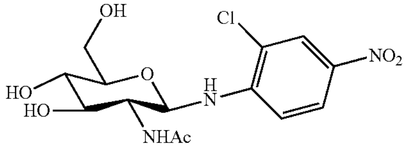
13
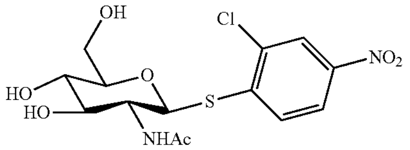
14
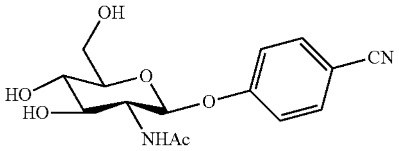
15
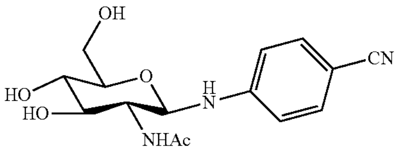
16
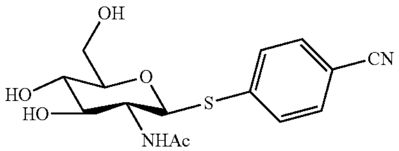
17
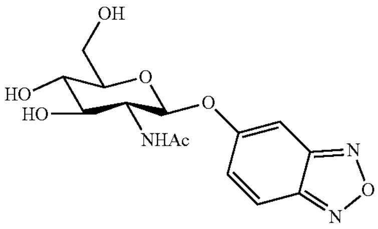
18
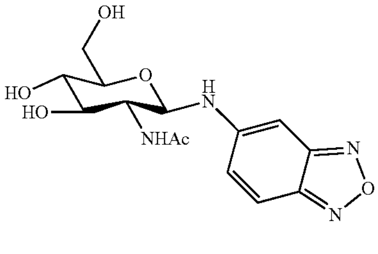

-continued
19
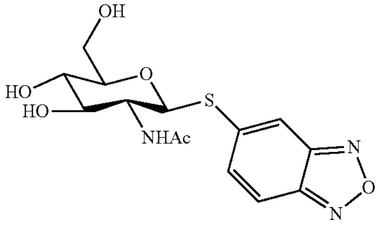
20
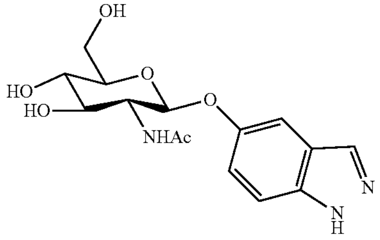
21
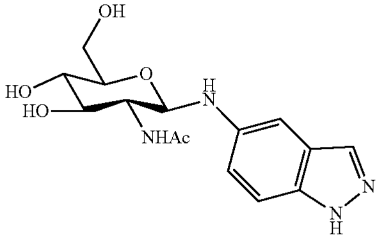
22
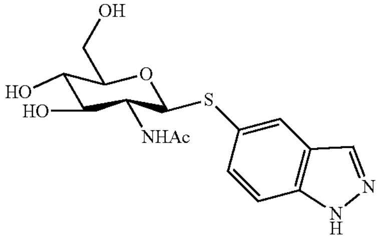
23
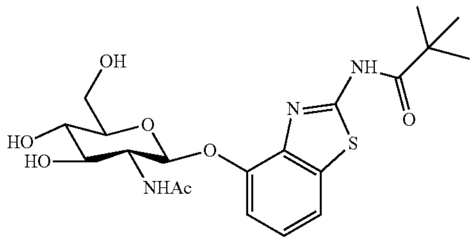
24
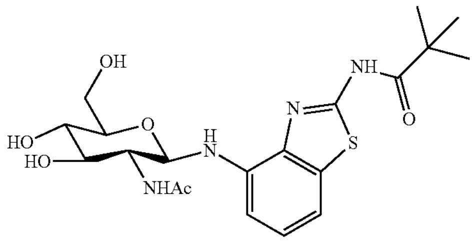
-continued
25
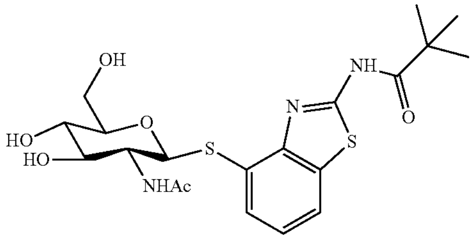
26
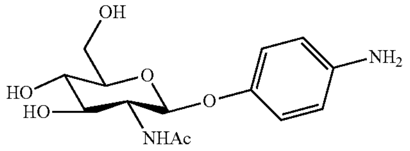
27
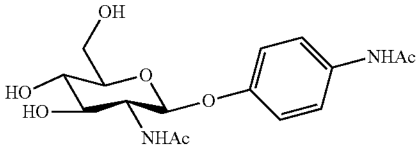
29
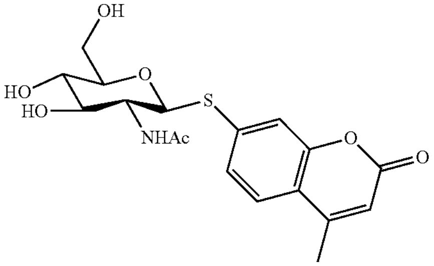
28
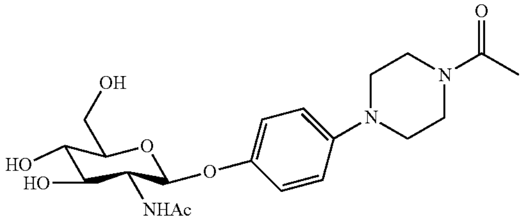
30
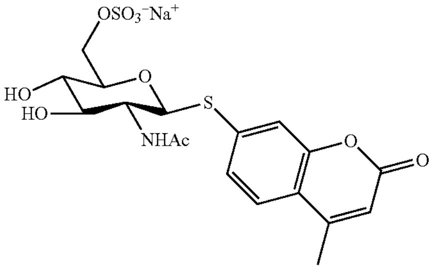
31
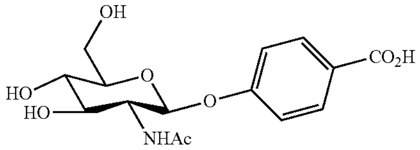

-continued

32

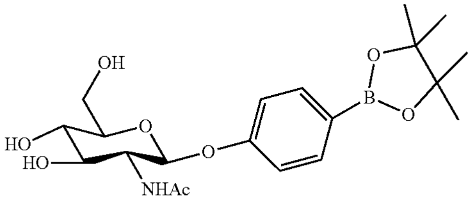

33

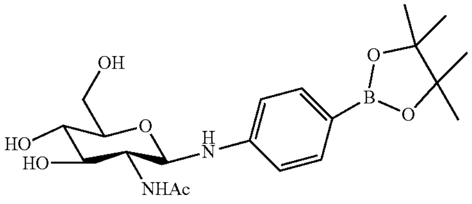

34

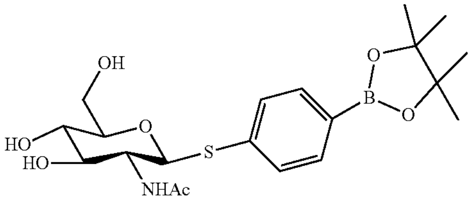

35

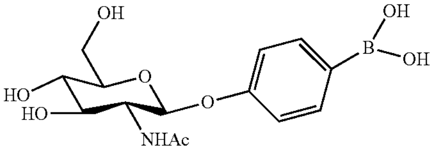

36

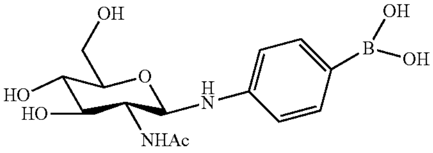

37

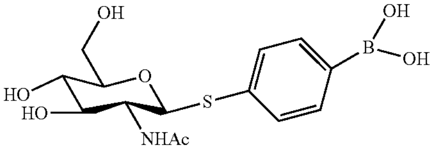

38

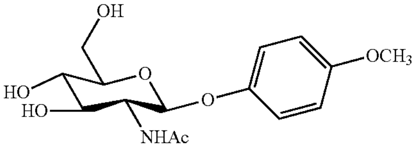

39

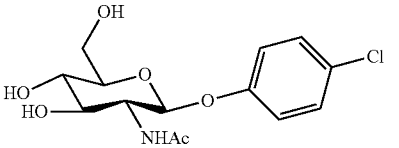

or

40

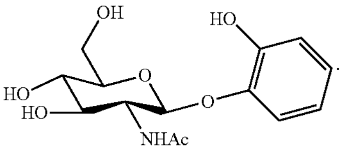

In another aspect, the method further comprises the step of identifying a subject in need of treatment for a pulmonary inflammation, distress or insufficiency prior to the treatment.

BRIEF DESCRIPTION OF THE DRAWINGS

For a more complete understanding of the features and advantages of the present invention, reference is now made to the detailed description of the invention along with the accompanying figures and in which:

(FIG. 2A) Representative H&E-stained lung paraffin sections showing histological changes after AVR-48 treatment. (FIG. 2B) Chord length (which measures the average free distance in the air spaces) is increased in the BPD group and normalizes after AVR-48 treatment. (FIG. 2C) The alveolar septal thickness is decreased and (FIG. 2D) the radial alveolar count (which measures the number of alveoli) is also improved after AVR-48 treatment. ***p<0.001, N=3-8; RA: room air; BPD: Bronchopulmonary dysplasia. Scale bar 100 μm.

(FIG. 3A) Total inflammatory cells in the BAL fluid in the BPD group is significantly decreased after AVR-48 treatment. (FIG. 3B) Total protein in the BAL fluid in the BPD group is significantly decreased after AVR-48 treatment. *p<0.05; p<0.01; *p<0.001, N=3-8; RA: room air; BAL: bronchoalveolar lavage; BPD: Bronchopulmonary dysplasia.

(FIG. 4B) Co-localization of SP-C (marker for Type II AECs) with PCNA. White arrows point to the respective cells that are proliferating. Extreme right panel shows higher magnification of proliferating Type II AECs positive for SP-C (cytoplasmic green) and PCNA (nuclear red) (FIG. 4C) Co-localization of RAGE (marker for Type I AECs) with PCNA. Extreme right panel shows higher magnification of proliferating Type I cells positive for RAGE (cytoplasmic green) and PCNA (nuclear red) p<0.01; *p<0.001; Scale bar 100 μm. RA: room air; BPD: Bronchopulmonary dysplasia; SP: surfactant protein; AECs: alveolar epithelial cells; PCNA: proliferating cell nuclear antigen; RAGE: receptor for advanced glycation end products.

(FIG. 6A) Representative immunofluorescent lung sections showing vascular development. vWF, a marker for blood vessels, is severely disrupted in BPD while after treatment with AVR-48, there is significant improvement. (FIG. 6B) Representative Western blotting showing Ang2 is restored after treatment with AVR-48, in the BPD group. The top right panel shows quantification of the number of blood vessels while the bottom right panel shows densitometric quantification for Ang2. Scale bar 100 μm; *p<0.05; p<0.01; *p<0.001; vWF: von Willebrand factor; Ang2: Angiopoetin 2; RA: room air; BPD: Bronchopulmonary dysplasia; HPF: high power field; N=3-5.

(FIG. 7A-7B) Representative western blot showing decrease of pro-inflammatory cytokines (TGFβ, NFkB, TNFα, IL-13, IL-1(3, IL-4) and increase of IL-10 in the lungs after treatment with AVR-48, as compared to the BPD group. The increased inflammation seen in the RA+AVR-48 treated group could be due to the natural defense adaptive mechanism. Vinculin is the loading control. The panels on the right show densitometric quantification of the proteins. N=5. (FIG. 7C) ELISA showing the expression of some selected cytokines in the blood serum of treated BPD group as compared to untreated BPD controls. The RA+AVR-48 group was not included for this assay. Although most of the pro-inflammatory cytokines and chemokines show a decrease after treatment, there was no change in MIP-2, IL-21 and IL-17. *p<0.05; p<0.01; *p<0.001, N=4-5; RA: room air; BPD: Bronchopulmonary dysplasia; TGFβ: transforming growth factor beta; MCP-1: monocyte chemoattractant protein 1; MIP-2: macrophage inflammatory protein 2; NfkB: nuclear factor kappa B, TNFα: tumor necrosis factor alpha, IFNγ: interferon gamma; IL: interleukin.

(FIG. 8A) The RV/LV ratio and Fulton's Index (RV/LV+IVS) is improved after AVR-48 treatment, in the BPD group. (FIG. 8B) Representative western blot showing an increased expression of Vegf in the BPD+AVR-48 treated group as compared to BPD group. (FIG. 8C) eNOS, BmpRII and VegfD which are increased in BPD, is noticeably decreased after treatment with AVR-48. Vinculin is the loading control. As the same samples were used for FIGS. 8A-8B and FIGS. 8B-8C, the same vinculin has been shown for both images as the loading control. N=4-5. BPD-PH: Bronchopulmonary dysplasia-associated pulmonary hypertension; RV: right ventricle; LV: left ventricle; IVS: interventricular septum; RA: room air; BPD: Bronchopulmonary dysplasia; Vegf: vascular endothelial growth factor; eNOS: endothelial nitric oxide synthase; BmpRII: Bone morphogenetic protein receptor 2.

(FIG. 12A) There was no difference in the total inflammatory cells as well as (FIG. 12B) the total protein in the BAL fluid between the BPD group treated with CS alone or with AVR-48 alone or with a combination of CS+AVR-48. *p<0.05; **p<0.01; RA: room air; BPD: Bronchopulmonary dysplasia; CS: Curosurf®, the surfactant used in this study; BAL: bronchoalveolar lavage; N=3-6.

(FIG. 13B) Mean AVR-48 concentrations in the lungs after IN or IP administration IP: intraperitoneal; IN: intranasal; N=6.

(FIG. 14B) Mean AVR-48 concentrations in the BAL following IV and SC administration. IV: intravenous; SC: subcutaneous; BALf: bronchoalveolar lavage fluid; N=6.

DETAILED DESCRIPTION OF THE INVENTION

Figure 1:
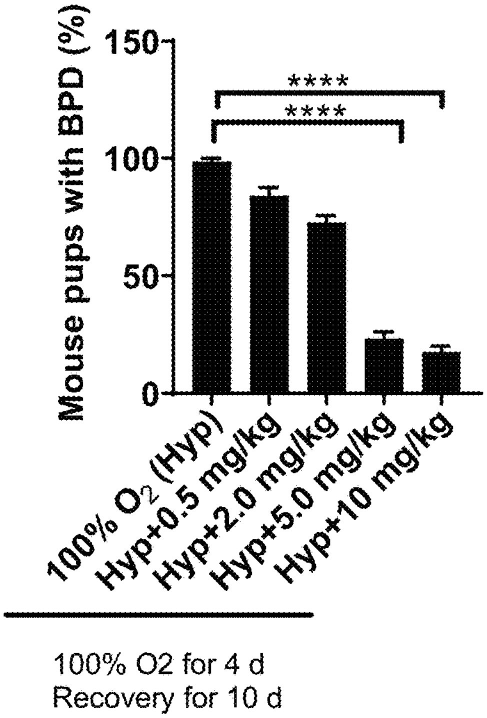
FIG. 1 is a dose response study of AVR-48 at different doses of 0.5, 2.0, 5.0 and 10 mg/kg, given IP. ****p<0.0001. N=5-7 mice per group. 10 mg/kg (IP) was selected as the most efficacious dose. IP: intraperitoneal; Hyp: hyperoxia; BPD: Bronchopulmonary dysplasia.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention combines surfactants isolated from lungs, such as bovine and porcine lungs (e.g., from pups or calves), with a bioactive molecule of Formula I:

Formula-I

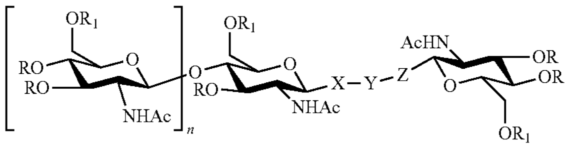

where n=0-5; X═NH, O, S, or $CH_2$; Y=Phenyl, or a phenyl group substituted with at least one methyl, a phenyl group substituted with at least one nitro, a phenyl group substituted with at least one nitrogen, a phenyl group substituted with at least one boron, or aryl, substituted aryl, heteroaryl, four to six membered cycloalkyl, four to six membered heterocycloalkyl; R═H, $C(O)R_2$, $SO_2R_2$; $R_1$═H, $C(O)R_2$, $SO_2R_2$; $R_2$=Ethyl, methyl, isopropyl, n-propyl, t-butyl, n-butyl, $NH_2$, $NR_3R_4$, $R_3$, $R_4$=Ethyl, methyl, isopropyl, n-propyl, t-butyl, n-butyl, three to six membered cycloalkyl and Z═NH, O, S, $CH_2$, or none. In one aspect, an amount of the compound is varied or selected to either inhibit or activate the immune response. In one aspect, the compound has the formula:

1

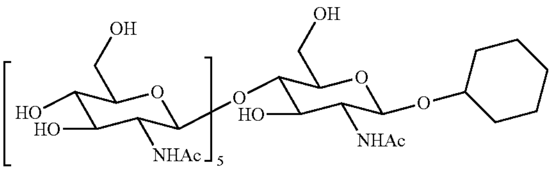

-continued

2

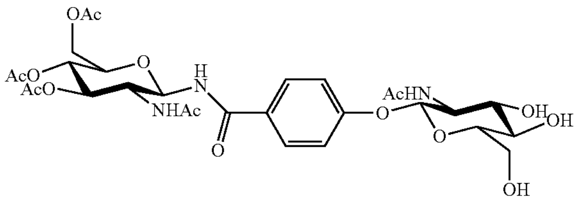

3

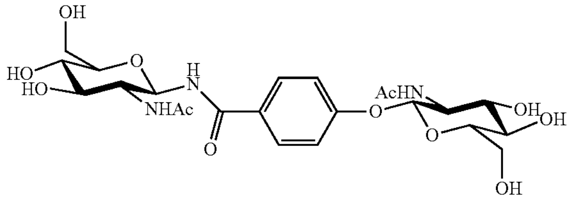

4

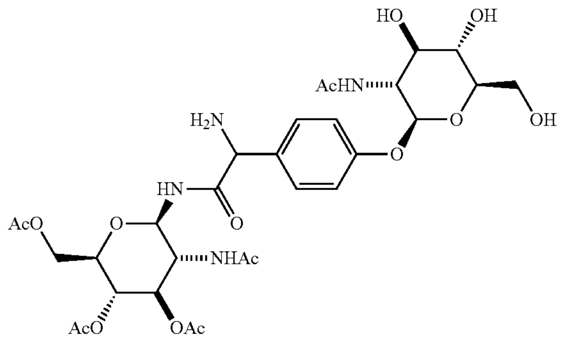

5

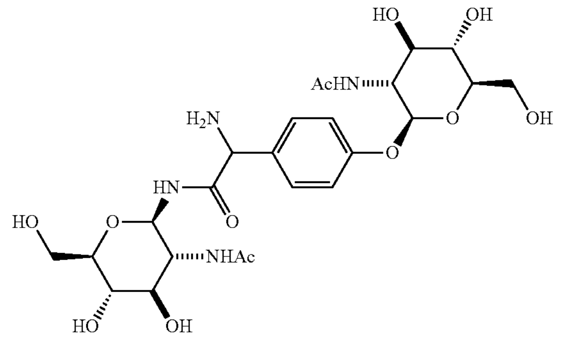

6

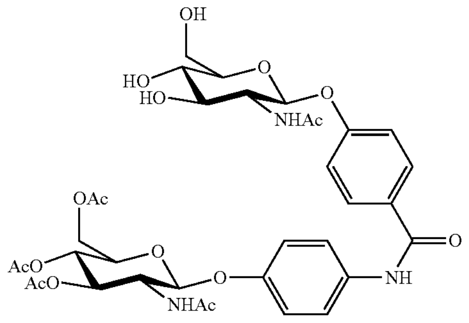

-continued
7
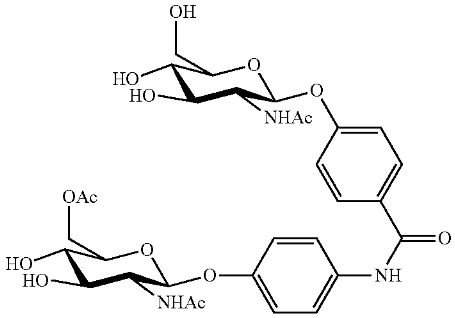
8
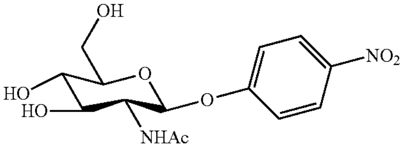
(AVR-48)
9
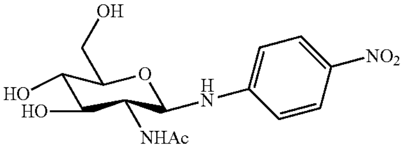
10
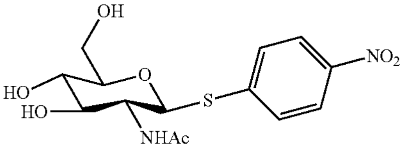
11
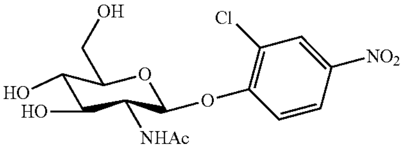
12
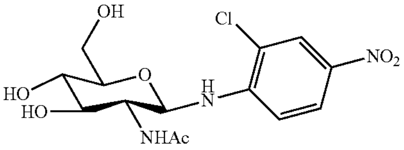
13
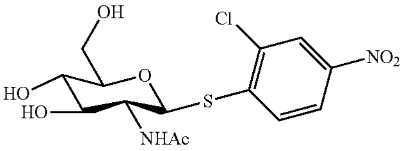
14
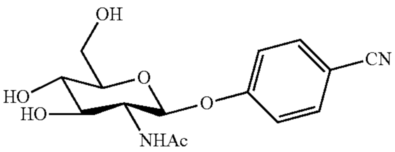
15
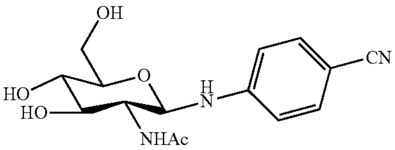
-continued
16
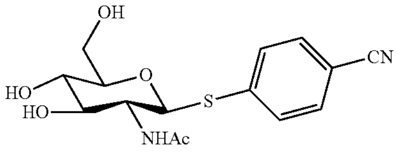
17
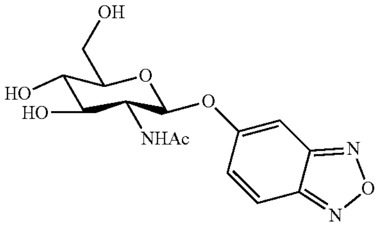
18
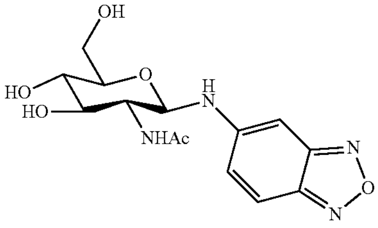
19
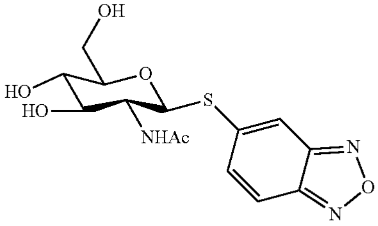
20
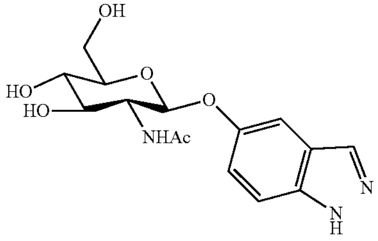
21
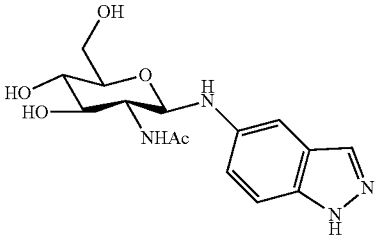
22
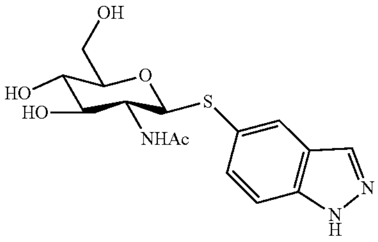

-continued
23
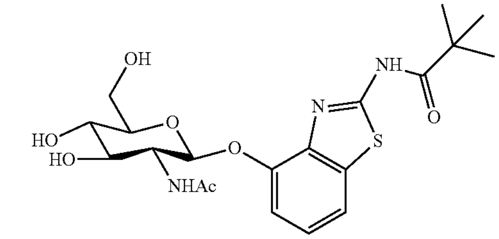
24
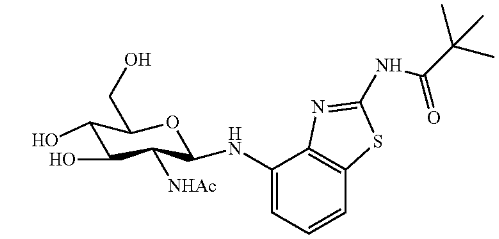
25
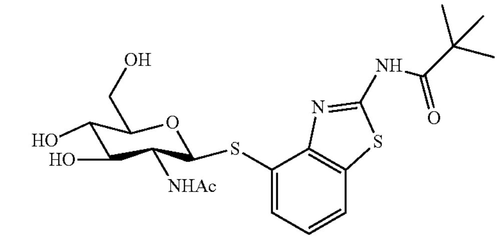
26
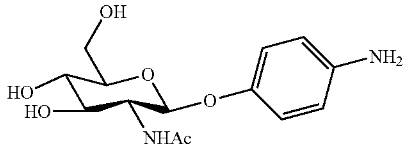
27
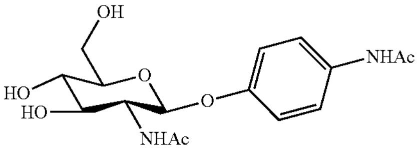
28
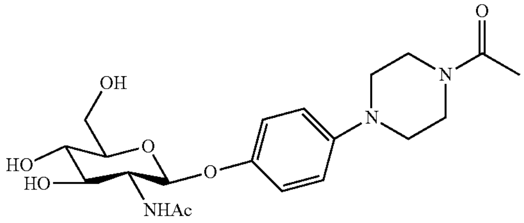
29
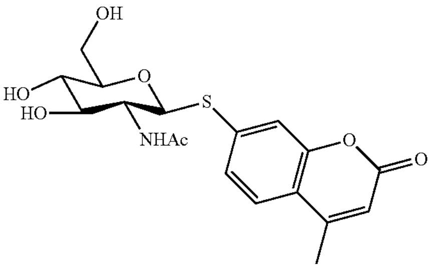
-continued
30
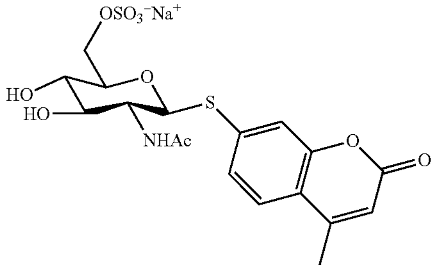
31
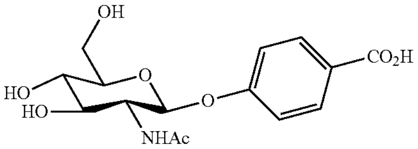
32
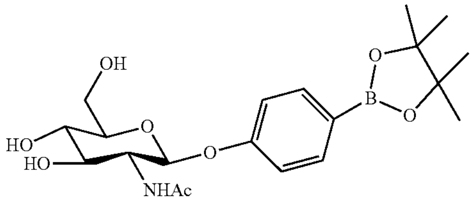
33
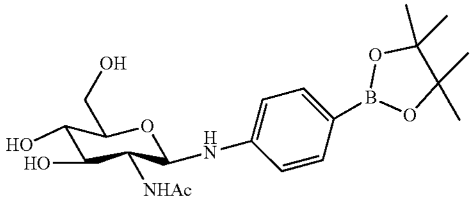
34
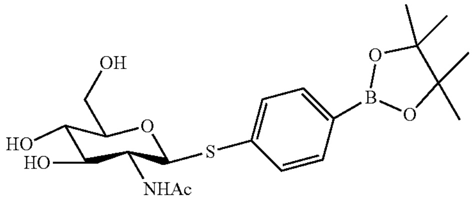
35
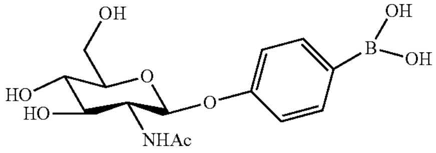
36
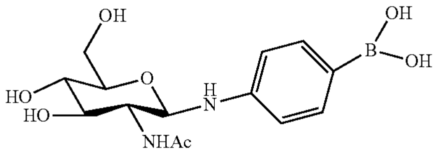
37
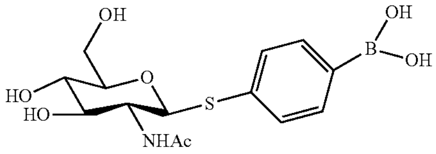

-continued

38

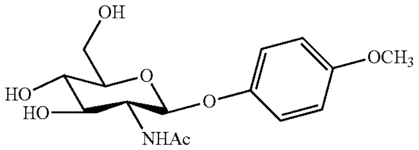

39

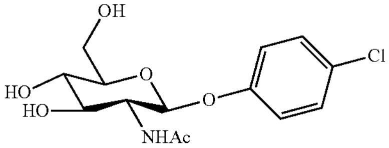

40

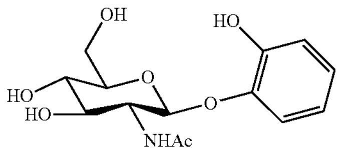

The compounds of the present invention find particular uses in the delivery of particles of low density and large size for drug delivery to the pulmonary system. Biodegradable particles have been developed for the controlled-release and delivery of compounds, such as those disclosed herein. Langer, R., Science, 249: 1527-1533 (1990).

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The present invention can be formulated for delivery to any part of the respiratory tract, e.g., Gonda, I. "Aerosols for delivery of therapeutic and diagnostic agents to the respiratory tract," in Critical Reviews in Therapeutic Drug Carrier Systems 6:273-313, 1990, relevant portions incorporated herein by reference. On one non-limiting example, the deep lung or alveoli are the primary target of inhaled therapeutic aerosols for systemic drug delivery of the present invention.

Inhaled aerosols have been used for the treatment of local lung disorders including asthma and cystic fibrosis and have potential for the systemic delivery of the compounds of the present invention. Pulmonary drug delivery strategies present many difficulties for the delivery of macromolecules, including: excessive loss of inhaled drug in the oropharyngeal cavity (often exceeding 80%), poor control over the site of deposition, irreproducibility of therapeutic results owing to variations in breathing patterns, the often too-rapid absorption of drug potentially resulting in local toxic effects, and phagocytosis by lung macrophages.

Considerable attention has been devoted to the design of therapeutic aerosol inhalers to improve the efficiency of inhalation therapies and the design of dry powder aerosol surface texture. The present inventors have recognized that the need to avoid particle aggregation, a phenomenon that diminishes considerably the efficiency of inhalation therapies owing to particle aggregation, is required for efficient, consistent deep lung delivery.

In one example for a formulation for pulmonary delivery, particles containing the active compound(s) of the present invention may be used with local and systemic inhalation therapies to provide controlled release of the therapeutic agent. The particles containing the active compound(s) permit slow release from a therapeutic aerosol and prolong the residence of an administered drug in the airways or acini, and diminish the rate of drug appearance in the bloodstream. Due to the decrease in use and increase in dosage consistency, patient compliance increases.

The human lungs can remove or rapidly degrade hydrolytically cleavable deposited aerosols over periods ranging from minutes to hours. In the upper airways, ciliated epithelia contribute to the "mucociliary escalator" by which particles are swept from the airways toward the mouth. It is well known that, in the deep lung, alveolar macrophages are capable of phagocytosing particles soon after their deposition. The particles containing the active compound(s) provided herein permit for an effective dry-powder inhalation therapy for both short- and long-term release of therapeutics, either for local or systemic delivery, with minimum aggregation. The increased particle size consistency is expected to decrease the particles' clearance by the lung's natural mechanisms until drugs have been effectively delivered.

PLGA encapsulated nanosuspension with extended drug release profile Nanoparticle formulation. Nanoparticle formulation can be carried out through a single or double emulsion technique. For example, for a single emulsion technique, 10 mg of compounds Or was dissolved in 3 ml of chloroform containing 100 mg of PLGA to form an oil phase. This solution was then added dropwise into 20 ml of 5% PVA solution (water phase) and emulsified at 50 W for 5 minutes to form the compound loaded nanoparticles. The final emulsion was stirred overnight to allow solvent evaporation. The nanoparticles were washed and collected by ultracentrifugation and lyophilized before use.

For example of a double emulsion technique, 30 mg of poly(D,L-lactide-co-glycolide) (PLGA) were dissolved in 1 mL of chloroform at 4° C. Concurrently, 2 mL of a 2% w/v poly(vinyl alcohol) (PVA)/distilled deionized water solution was formed. Upon solubilization of the PVA in water, 1 mL of ethanol or methanol was added as a non-solvent to the PVA solution. The active compound was then added to the PVA/ethanol solution at a concentration of 1 mM and stirred. A stock solution of active agent, e.g., 10 mg/ml, is formed by the dissolution of curcumin into water under alkaline conditions using, e.g., 0.5 M NaOH. The active agent is added to the PLGA/Chloroform solution at concentrations of 0.5, 1.0, and 2.0 mg/mL per 150 microliters of aqueous volume. Formation of the primary emulsion is done by vortexing the active agent-PLGA/cholorform solution for 20 seconds, followed by tip sonication at 55 W for 1 minute on a Branson Sonifier model W-350 (Branson, Danbury, CN). The primary emulsion is then added to a BS3/PVA/ethanol solution to initiate formation of the secondary emulsion. Completion of the secondary emulsion is done through vortexing for 20 seconds and tip sonication at 55 W for 2 minutes. Stabile activated nanoparticles are then aliquoted into 1.5 mL Eppendorf tubes and centrifuged for 5 minutes at 18,000 g. The chloroform and residual PVA supernatant were aspirated off and particles were resuspended by tip sonication in, e.g., 1 mL of phosphate buffered saline (PBS) pH 7.2. Following resuspension, nanoparticles were placed at −80° C. for 1 hour and lyophilized overnight. Lyophilization can be carried out in an ATR FD 3.0 system (ATR Inc, St. Louis, MO) under a vacuum of 250 µT. After lyophilization nanoparticles are stored at 4° C. Upon use nanoparticles were weighed into eppendorf tubes and resuspended in 1 mL of PBS pH 7.4.

In some embodiments, the compounds of the present disclosure are incorporated into parenteral formulations. The term parenteral as used herein includes subcutaneous, intravenous, intramuscular, and intra-arterial injections with a variety of infusion techniques. Intra-arterial and intravenous injection as used herein includes administration through catheters. Preferred for certain indications are methods of administration that allow rapid access to the tissue or organ being treated, such as intravenous injections for the treatment of endotoxemia or sepsis.

The compounds of the present disclosure will be administered in dosages which will provide suitable inhibition or activation of TLRs of the target cells; generally, these dosages are, preferably between 0.25-50 mg/patient, or from 1.0-100 mg/patient or from 5.0-200 mg/patient or from 100-500 mg/patient, more preferably, between 0.25-50 mg/patient and most preferably, between 1.0-100 mg/patient. The dosages are preferably once a day for 28 days, more preferably twice a day for 14 days or most preferably 3 times a day for 7 days.

Pharmaceutical compositions containing the active ingredient may be in any form suitable for the intended method of administration. Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000, and updates thereto; Martindale, The Extra Pharmacopoeia, Thirty-Second Edition (The Pharmaceutical Press, London, 1999); all of which are incorporated by reference, and the like, relevant portions incorporated herein by reference.

The present invention includes compositions and methods for making and generating aerosols for delivery of the active agents described herein at the specific doses. In one embodiment, the compounds are formulation to be aerosolized with an aerosol-generating device. A typical embodiment of this invention includes a liquid composition having predetermined physical and chemical properties that facilitate forming an aerosol of the formulation. Such formulations typically include three or four basic parameters, such as, (i) the active ingredient; (ii) a liquid carrier for the active ingredient; (iii) an aerosol properties adjusting material; and optionally, (iv) at least one excipient. The combination of these components provides a therapeutic composition having enhanced properties for delivery to a user by generating an inhalable aerosol for pulmonary delivery.

Aqueous suspensions of the compounds of the present invention contain the active materials in admixture with excipients suitable for the manufacture of aqueous suspensions. Such excipients include a suspending agent, such as sodium carboxymethylcellulose, methylcellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate.

The pharmaceutical compositions of the invention can be in the form of a sterile injectable preparation, such as a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenteral-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables.

In some embodiments the formulation comprises PLA or PLGA microparticles and may be further mixed with $Na_2HPO_4$, hydroxypropyl methylcellulose, polysorbate 80, sodium chloride, and/or edetate disodium.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

It will be understood, however, that the specific dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

In some embodiments the compositions of the present disclosure also contain from about 80% to about 99.5%, preferably from about 90 or 95% to about 98.5% of a compatible non-aqueous pharmaceutically acceptable topical vehicle. Some vehicles are described in U.S. Pat. No. 4,621,075, which is incorporated herein for this disclosure. Although it is preferred that these vehicles be free of water, the compositions of the present invention may contain up to about 5% water without significant adverse effects on the formation of the desired gels. These non-aqueous vehicle components are also well-known in the pharmaceutical arts, and they include (but are not limited to) short chain alcohols and ketones and emollients, such as hydrocarbon oils and waxes, lanolin and lanolin derivatives, silicone oils, monoglyceride, diglyceride, and triglyceride esters, fatty alcohols, alkyl and alkenyl esters of fatty acids, alkyl and alkenyl diesters of dicarboxylic acids, polyhydric alcohols and their ether and ester derivatives; wax esters and beeswax derivatives. Preferred vehicles incorporate methanol, ethanol, n-propanol, isopropanol, butanol, polypropylene glycol, polyethylene glycol and mixtures of these components.

Particularly preferred vehicles include ethanol, n-propanol and butanol, especially ethanol. These preferred solvents may also be combined with other components, such as diisopropyl sebacate, isopropyl myristate, methyl laurate, silicone, glycerine and mixtures of these components, to provide non-aqueous vehicles which are also useful in the present invention. Of these additional components, diisopropyl sebacate is especially useful. In fact, preferred vehicles include mixtures of ethanol and diisopropyl sebacate in ratios, by weight, of from about 4:1 to about 1:4. Preferred vehicles contain from about 15% to about 35% diisopropyl sebacate and from about 65% to about 85% ethanol.

Compositions of the present invention may additionally contain, at their art-established usage levels, compatible adjunct components conventionally used in the formulation of topical pharmaceutical compositions. These adjunct components may include, but are not limited to, pharmaceutically-active materials (such as supplementary antimicrobial or anti-inflammatory ingredients, e.g., steroids) or ingredients used to enhance the formulation itself (such as excipients, dyes, perfumes, skin penetration enhancers, stabilizers, preservatives, and antioxidants). Examples of such agents include the pharmaceutically-acceptable acidic carboxy polymers, such as the Carbopol compounds commercially available from B. F. Goodrich Chemicals, Cleveland, Ohio.

In one embodiment, the compounds of the present invention may be formulated into a cream, lotion or gel packaged in a common trigger spray container will be firmly adhered to the area of interest as a regular cream does after it is sprayed out from the container. This is described in WO 98/51273, which is incorporated herein by reference. Accordingly, in one aspect, the present disclosure provides a pharmaceutical that can be incorporated into a non-aerosol spray composition for topical application, which comprises the compounds as described herein alone or in combination. The compounds are present in an amount in the range of 0.1% to 20% or in some embodiments from 1 to 15% by weight, or in some embodiments from 2 to 10% by weight of cream, lotion or gel. The compounds of the present invention can be incorporated into a neutral hydrophilic matrix cream, lotion or gel. In a first embodiment, the cream or lotion matrix for topical application is characterized by polyoxyethylene alkyl ethers. In a second embodiment, the gel is characterized by high molecular weight polymer of cross-linked acrylic acid. Polyoxyethylene alkyl ethers are non-ionic surfactants widely used in pharmaceutical topical formulations and cosmetics primarily as emulsifying agents for water-in-oil and oil-in-water emulsions. It is characterized in this invention as a base for non-aerosol trigger sprayable cream or lotion. Cross-linked acrylic acid polymer (Carbomer) employed to form the gel is another object of this invention.

A particularly suitable base for non-aerosol spray is therefore a cream or lotion containing from 1 to 25% of polyoxyethylene alkyl ethers, 3 to 40% of humectant and 0.1 to 1% of preservative or preservatives and the balance to 100% being purified water. Aptly the polyoxyethylene alkyl ether can be one or any combination selected from the group consisting of polyoxyl 20 cetostearyl ether (Atlas G-3713), poloxyl 2 cetyl ether (ceteth-2), poloxyl 10 cetyl ether (ceteth-10), poloxyl 20 cetyl ether (ceteth-20), poloxyl 4 lauryl cetyl ether (laureth-4), poloxyl 23 lauryl cetyl ether (laureth-23), poloxyl 2 oleyl ether (oleth-2), poloxyl 10 oleyl ether (oleth-10), poloxyl 20 oleyl ether (oleth-20), poloxyl 2 stearyl ether (steareth-2), poloxyl 10 stearyl ether (steareth-10), poloxyl 20 stearyl ether (steareth-20), and poloxyl 100 stearyl ether (steareth-100). Suitable humectant can be one or any combination selected from the group consisting of propylene glycol, polyethylene glycol, sorbitol or glycerine. Suitable preservative is one or any combination selected from the group consisting of methylparaben, propylparaben, benzyl alcohol, benzoic acid, sodium benzoate, sorbic acid and its salt or phenylethyl alcohol.

Another suitable base for non-aerosol spray is a gel containing from 0.1 to 2.0% of Carbomer, 0.1 to 1% of alkaline solution, 3 to 40% of humectant and 0.1 to 1% of preservative or preservative as and the balance to 100% being purified water. Aptly the Carbomer can be one or any combination selected from the group consisting of Carbomer 934, Carbomer 940 or Carbomer 941. The suitable humectant, preservative and purified water for the gel are same as that in the case or cream or lotion. Other sprayable formulations are described in US Pre-Grant Publication US2005/00255048, which is expressly incorporated herein by reference.

The present invention provides for the first time a dual acting small molecule that can produce alternatively activated macrophages and inhibit LPS induced inflammation leading to organ protection and limit tissue injury. One such compound is compound 8 (AVR-48), which was designed and identified to bind differently to its target. Instead of binding to the TLR4-MD2 complex like other antagonists such as Eritoran (Kim, Park et al. 2007), it binds directly to the active site of TLR4, thus inhibiting the downstream components. In addition, a novel series of compounds were designed and identified by SAR study such as Compounds 1, 3, 8 and 32 that also bind TLR4 in an in vitro model system using THP-1 human monocytic cell line, peripheral blood mononuclear cells and decrease inflammatory cytokines in neonatal mouse pups with BPD. The present invention provided first time the invention that, Compounds 8 bind to the surface receptor proteins TLR4 and scavenger receptor CD163 in mouse spleen monocytes and macrophages and via binding to the receptor it polarizes them towards more phagocytic resident/anti-inflammatory macrophages.

Chitin and chitosan have excellent properties for ideal drugs delivery (Janes, Fresneau et al. 2001, Williams, Lansdown et al. 2003, Li, Zhuang et al. 2009). LMW chitosan are natural molecules with no systemic toxicity. These are excellent candidates for drug-like target with the ability to be delivered as polymeric nanoparticles The in silico model of binding of N-hexaacetyl chitohexaose to the TLR4 active site was presented in the inventors' previous publication (Panda, Kumar et al. 2012). Based on preliminary results and molecular docking, the inventors designed and synthesized several compounds as shown above and screened in in vitro assays. Based on the optimal physicochemical property, the inventors have selected compounds 1, 3, 8 and 32 to be studied in the developmentally-appropriate hyperoxia-exposed BPD mouse model. Compound 8 (AVR-48) was further selected as the lead compound based on the mouse BPD model results and further evaluated in a large animal model of BPD; pre-term lamb model.

Example 1. Chitin-Derived AVR-48 (Compound 8) Prevents Experimental Bronchopulmonary Dysplasia (BPD) and BPD-Associated Pulmonary Hypertension in Newborn Mice Safety Profile of AVR-48. To assess the safety of AVR-48 (compound 8), two doses of intravenous (IV) slow bolus injections or subcutaneous (SC) injections or intranasal (IN)

instillation were given to mice or rat pups (postnatal day 3-5 or P3-P5), >6 h apart. The total daily doses were up to 100 mg/kg/day IV, and up to 150 mg/kg/day SC, for 3 consecutive days. All doses were well tolerated and there were no observed adverse clinical signs and or any change in body weight (data not shown). A slight decrease in white blood cell count, lymphocyte count (in females only) and total bilirubin levels (SC groups only) were noted in treated animals that were considered to be non-adverse since they were mild and not dose dependent in frequency or severity (data not shown). In the pups dosed with AVR-48 (compound 8) twice daily IV at 50 mg/kg/dose, a higher incidence of dermal/subcutaneous hemorrhage at the injection site was frequently associated with subcutaneous mixed cell infiltrate in the cheek, mandibular or cervical areas, as compared to animals dosed IV with vehicle only. Although uncertain, a higher incidence of these symptoms in IV dosed pups indicates that they could be drug-related vascular irritation. There was no change in any of the hematological or clinical chemistry parameters. Signs of discoloration, swelling, and macroscopic and microscopic signs of local irritation occurred at the site of administration in all treatment groups and were attributed to the administration vehicle (formulation of 10% DMSO, 20% Tetraglycol, and 20% PEG 400 in sterile water). There was no evidence of any AVR-48 related systemic gross observations at necropsy in the visceral organs of both mouse and rat pups (data not shown), and no adverse findings attributable to AVR-48. Based on the parameters monitored in this study, the maximum tolerated dose (MTD) and no-observed-adverse-effect level (NOAEL) were considered to be 100 mg/kg/day via IV and 150 mg/kg/day via SC routes of dosing.

Pharmacokinetic (PK) Profile of AVR-48 (compound 8). The PK studies of AVR-48 were developed and designed in-house, by high performance liquid chromatography (HPLC), in both mouse and rat pups by IV, IP and IN dosing, to check the bioavailability of the drug formulated as solution, suspension or nanoparticle encapsulation in plasma, broncho-alveolar lavage fluid (BALF) and lung tissues.

The first study was done in the plasma of mouse pups by IP and IN routes to determine the dose range for efficacy. A $T_{max}$ of 0.0833 hours (hr) was found for either 10 mg/kg or 0.22 mg/kg IP dose with rapid clearance from the blood with $T_{1/2}$ of 0.36 hr for the 10 mg/kg dose. The number of samples with AVR-48 levels above the lower limit of quantitation (LLOQ) did not allow for $T_{1/2}$ determination in the 0.22 mg/kg dose. For IN dosing, a $T_{max}$ of 1 h was found even with a dose of 0.22 mg/kg and rapid clearance was observed by 2 h. The availability of AVR-48 in the lung tissues was similar to that of plasma both by IP and IN routes; a $T_{max}$ of 0.0833 hour was recorded for the 10 mg/kg dose. Low levels of AVR-48 did not allow for $T_{1/2}$ determination in the 10 mg/kg dose. Also, extremely low levels of AVR-48 in the lung tissue did not allow for any PK parameters to be calculated for the 0.22 mg/kg dose. Taken together, these data suggest that AVR-48 is cleared from circulation rapidly in the mouse pups following IP injection (Shah, Das et al. 2021) and that the observed efficacy in preventing BPD in the mouse pups by IP injection may be due to systemic exposure of AVR-48. Nevertheless, these data demonstrate the feasibility of delivering AVR-48, via IN as well as IP routes.

The second PK study was performed in rat pups wherein AVR-48 was administered by either SC or IV at 100 and 150 mg/kg/day for 3 consecutive days and the maximum plasma concentration of the drug was recorded at 30 and 60 minutes (min) ($T_{max}$) for the above 2 groups, respectively. For the IV dosed animals, the maximum concentration of AVR-48 in plasma declined in a bi-exponential fashion where $T_{1/2}$ was not estimable. For SC dosed animals only, $AUC_{(0-t)}$ increased in a dose-proportional manner between 50 and 75 mg/kg/dose. The exposure to AVR-48 did not change substantially after 3 days of twice daily administration and there was no accumulation of the drug. Absolute bioavailability was estimated at (2010/5460)*100=36% on Day 1 and (2610/4200)*100=62% on Day 3 using $AUC_{(0-t)}$.

In the BALF, the maximum AVR-48 (compound 8) concentration on Day 1 ranged from 0.891 to 1.07 μg/mL ($C_{max}$) and appeared between 2- and 15-min post dosing. The maximum BALF AVR-48 concentration on Day 3 ranged from 0.780 to 1.67 μg/mL ($C_{max}$) and occurred between 15- and 60-min post doses ($T_{max}$) for both routes of administration. A sustained level of AVR-48 was observed only where $T_{1/2}$ was not estimable. For the IV dosed animals only, maximum concentration was followed by decline on PK Day 1 but was followed by sustained level of AVR-48 on PK Day 3. $T_{1/2}$ was also not estimable. For SC dosed animals only, $AUC_{(0-t)}$ increased in a dose-proportional manner between 100 and 150 mg/kg/day, except on Day 3 where $AUC_{(0-t)}$ decreased in a less than dose-proportional manner. In summary, exposure to AVR-48 increased for 100 mg/kg/day for both routes after 3 days of twice daily administration but not for the 150 mg/kg/day groups. The accumulation ratio using $AUC_{(0-t)}$ for the IV dosed animals was 2.04, and for the SC dosed animals they were 1.90 and 0.880 for the 100 and 150 mg/kg/day doses, respectively.

Drug release and dose response study. The size of the poly D, L-lactic-co-glycolic acid (PLGA) encapsulated nanoparticle form of AVR-48 was determined using dynamic light scattering (DLS) and was found to be 369±45 nm and zeta potential to be −19.36 mV. There was ~60% drug release from the PLGA encapsulated AVR-48 nanosuspension in PBS7.4 at 37° C. during first 12 h followed by 70-100% release over 15 days. The inventors conducted a maximum dose response study using several concentrations of AVR-48 nanosuspension and determined that 0.11 mg/kg is a safe and efficacious dose. In an earlier report (Shah, Das et al. 2021), the inventors demonstrated the efficacy dose of AVR-48 (compound 8) to be 10 mg/kg/dose IV, in an adult respiratory distress syndrome/acute lung injury (ARDS/ALI) mouse model. In the present study, the $C_{max}$ values in the plasma of the mouse pups gave a clue that a single IV or IP injection of 10 mg/kg dose of AVR-48 provided $C_{max}$ of 5.78±0.91 μM should be sufficient to produce the desired anti-inflammatory therapeutic response. Hence, 10 mg/kg was selected as the optimum dose for AVR-48 to be tested in the BPD mouse model studies to subsequently conduct a dose response study to determine the minimum efficacy dose.

Simultaneously, the AVR-48 nanosuspension formulation IN (0.11 mg/kg) was tested as well as in solution form, IP and IV (10 mg/kg) (through the facial vein), and confirmed that all routes of administration gave similar outcomes. To prove that AVR-48 reached the lungs when delivered IN, the test compound was conjugated with fluorescein isothiocyanate (FITC) and then evaluated histologically to confirm that it did reach the lungs, as was evident from green fluorescent staining on lung sections. From the PK study, as described above, the bioavailability of the drug in the plasma and lungs were similar when delivered as solution formulation via either IN or IP routes. As the goal of this study is to develop AVR-48 as a commercially viable and applicable therapeutic candidate for BPD, the IP route was selected as the preferred mode of drug delivery in neonatal murine pups, with the rationale that it would be easier to deliver the drug systemically to preterm babies IV, rather than the IN route. The results and outcome of all the routes of administration have been presented in a cumulative manner, as the endpoint was similar for all routes of administration. The dose response study via IP dosing using 0.5, 2.0, 5.0 and 10 mg/kg doses demonstrated that 5.0 mg/kg is the minimum efficacious dose while 10 mg/kg was the optimum dose in preventing the BPD (>80%) phenotypes (FIG. 1). The PLGA nanosuspension (0.11 mg/kg) when delivered IN also resulted in similar efficacy. FIG. 1 is a dose response study of AVR-48 at different doses of 0.5, 2.0, 5.0 and 10 mg/kg, given IP. ****$p<0.0001$. N=5-7 mice per group. 10 mg/kg (IP) was selected as the most efficacious dose. IP: intraperitoneal; Hyp: hyperoxia; BPD: Bronchopulmonary dysplasia.

Figure 2A:
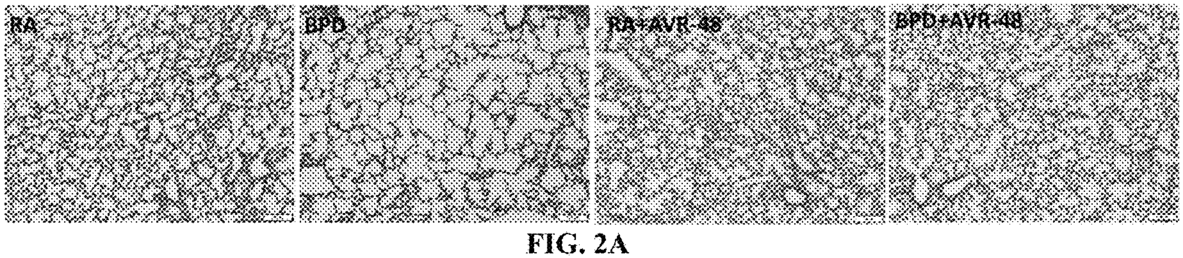
FIGS. 2A to 2D show that AVR-48 improves lung morphology.
Figure 2B:
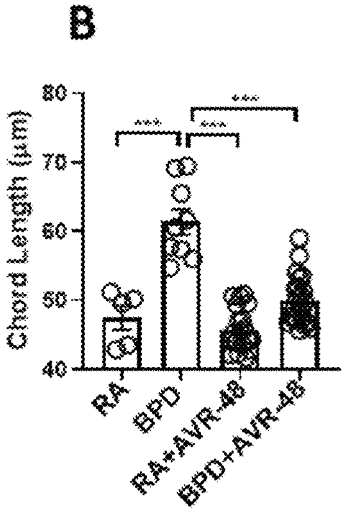
Figure 2C:
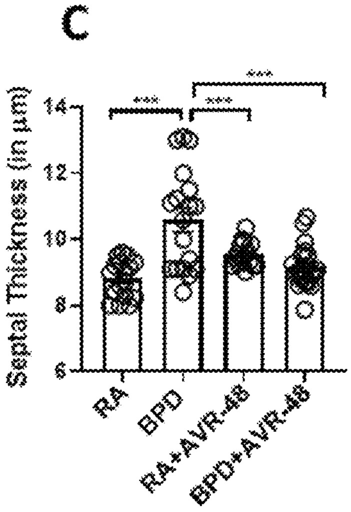
Figure 2D:
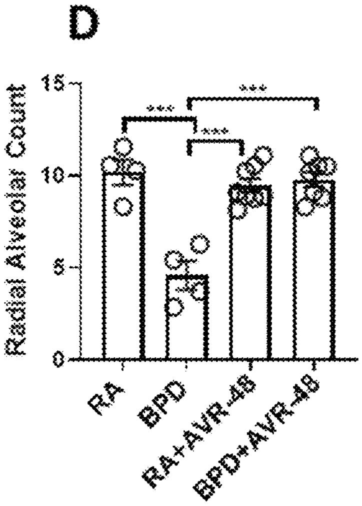
Figure 3A:
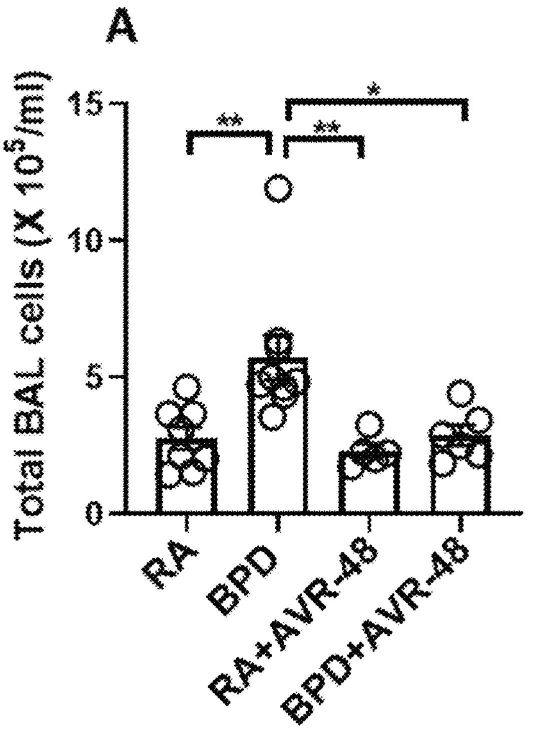
FIGS. 3A and 3B show that AVR-48 decreases inflammation and vascular leak.
Figure 3B:
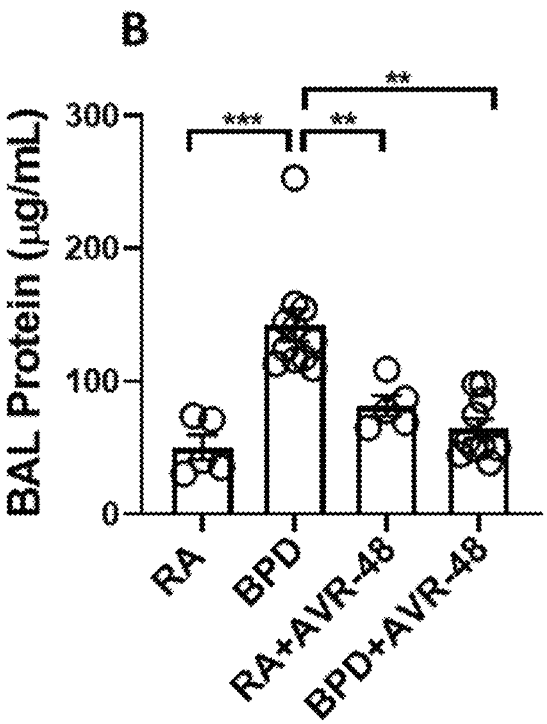
Figure 4A:
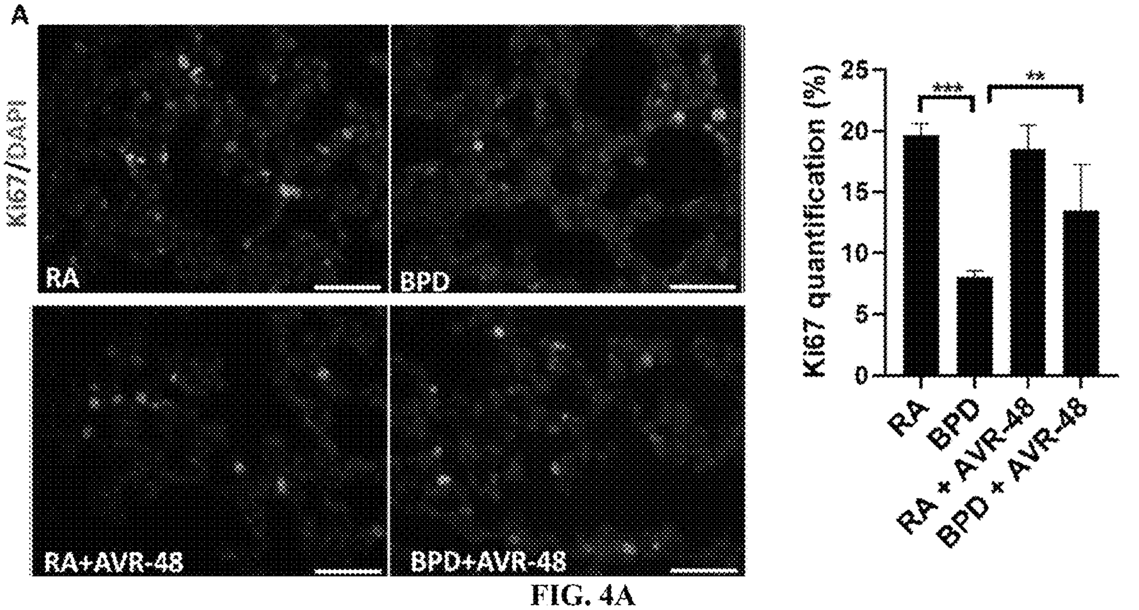
FIGS. 4A to 4C shows that AVR-48 improves cell proliferation (FIG. 4A) AVR-48 treatment in the BPD group increases cell proliferation (as shown by Ki67 staining) and the right panel shows quantification for Ki67.
Figure 4B:
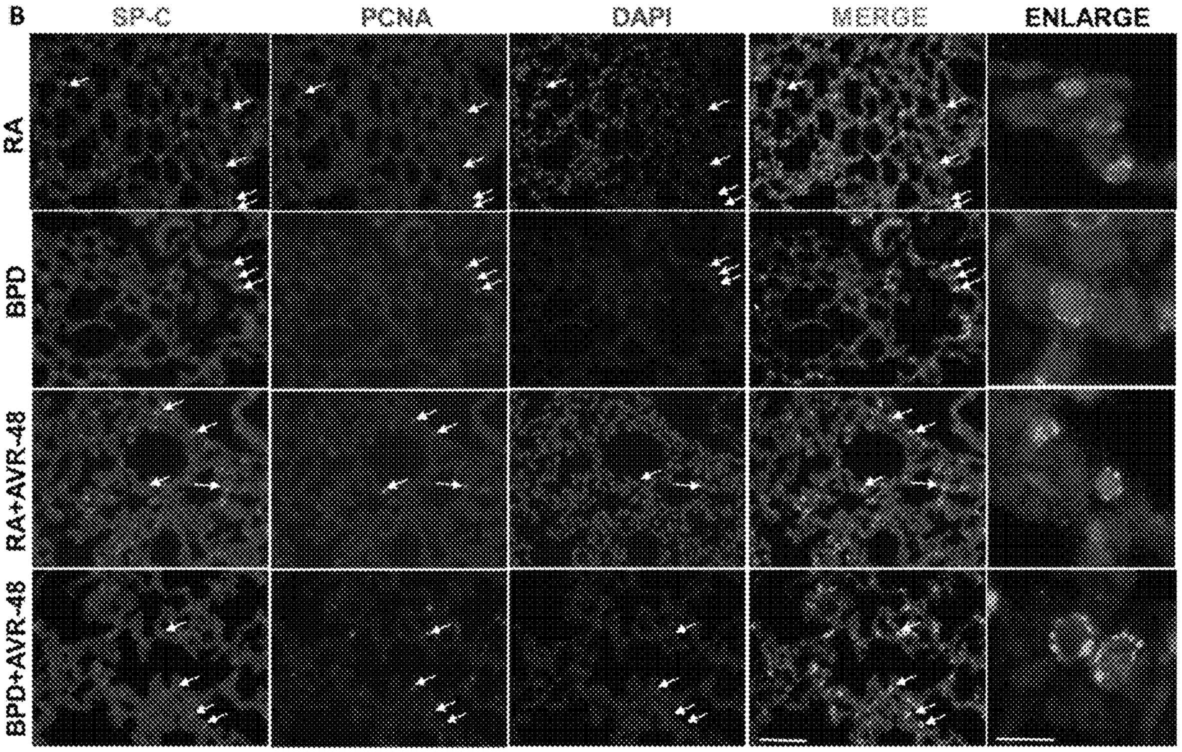
Figure 4C:
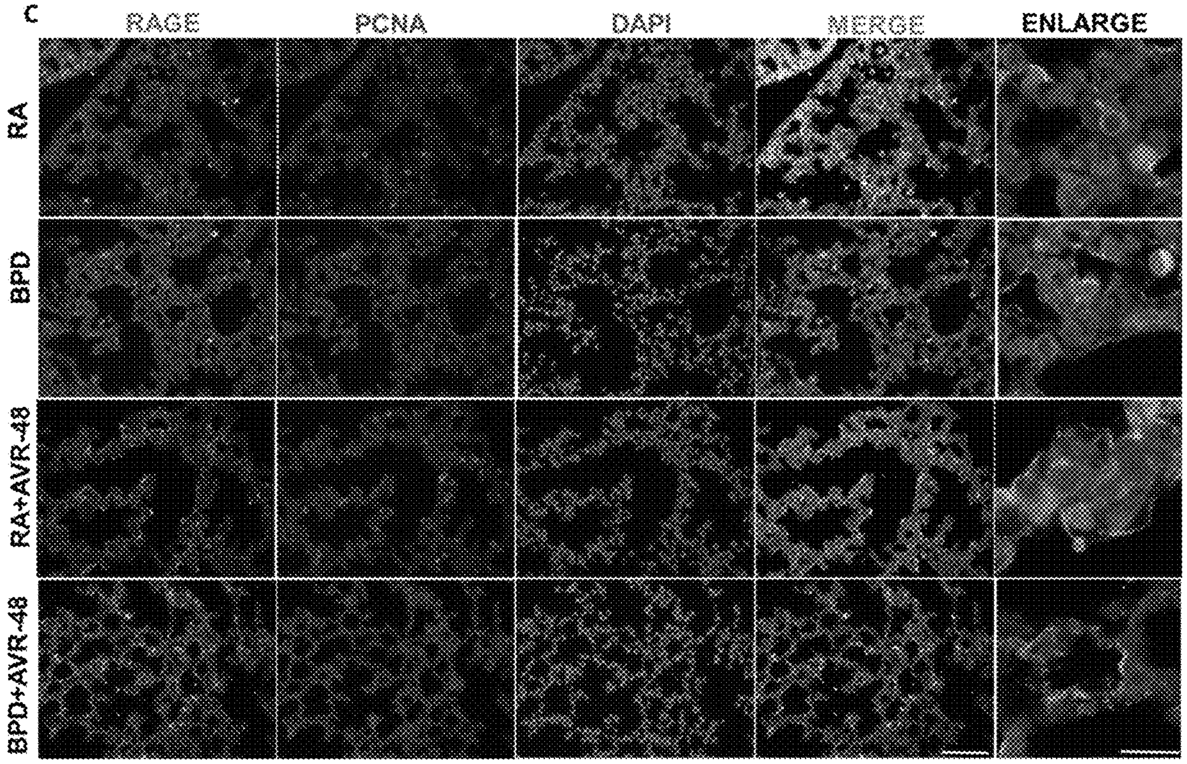
Figure 5A:
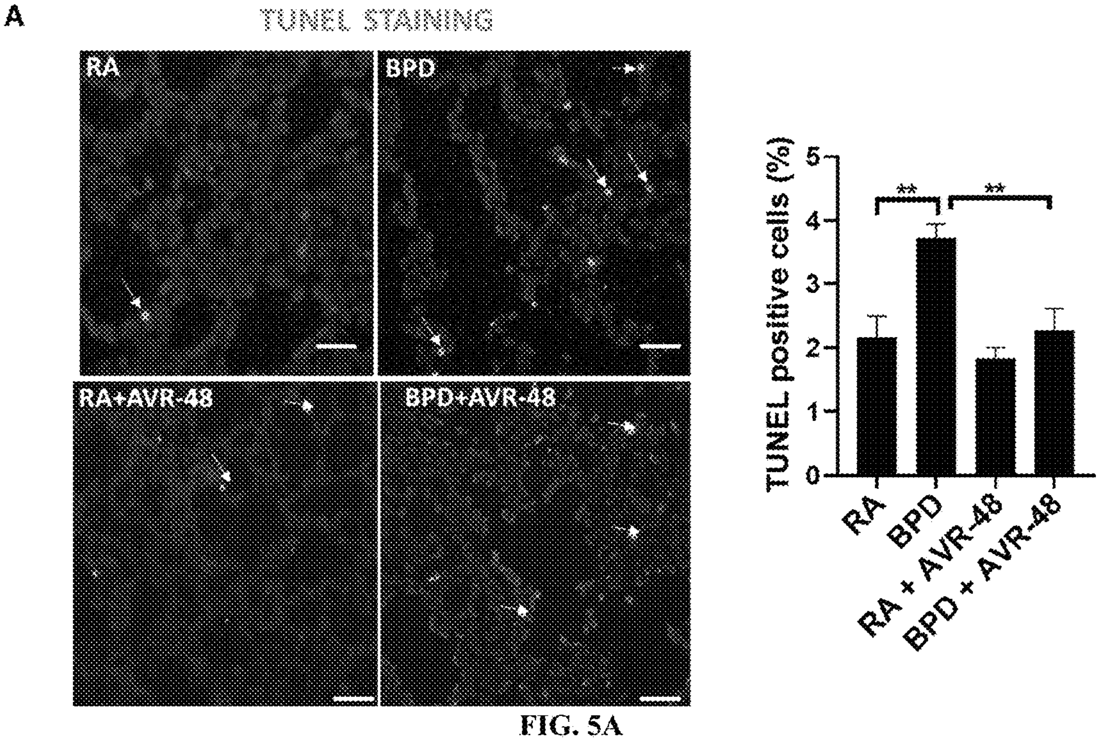
FIGS. 5A and 5B show that AVR-48 decreases cell death: TUNEL staining (white arrows point to TUNEL positive cells) (FIG. 5A) and western blotting of total caspase 3 and cleaved caspase 3, (FIG. 5B) shows decrease in cell death and apoptosis after treatment with AVR-48. Right panel shows quantification of TUNEL positive cells (top) and densitometric quantification of total caspase 3 and cleaved caspase 3. N=3-4 p<0.01; *p<0.001; Scale bar 100 μm. RA: room air; BPD: Bronchopulmonary dysplasia; Cl Cas: cleaved caspase.
Figure 5B:
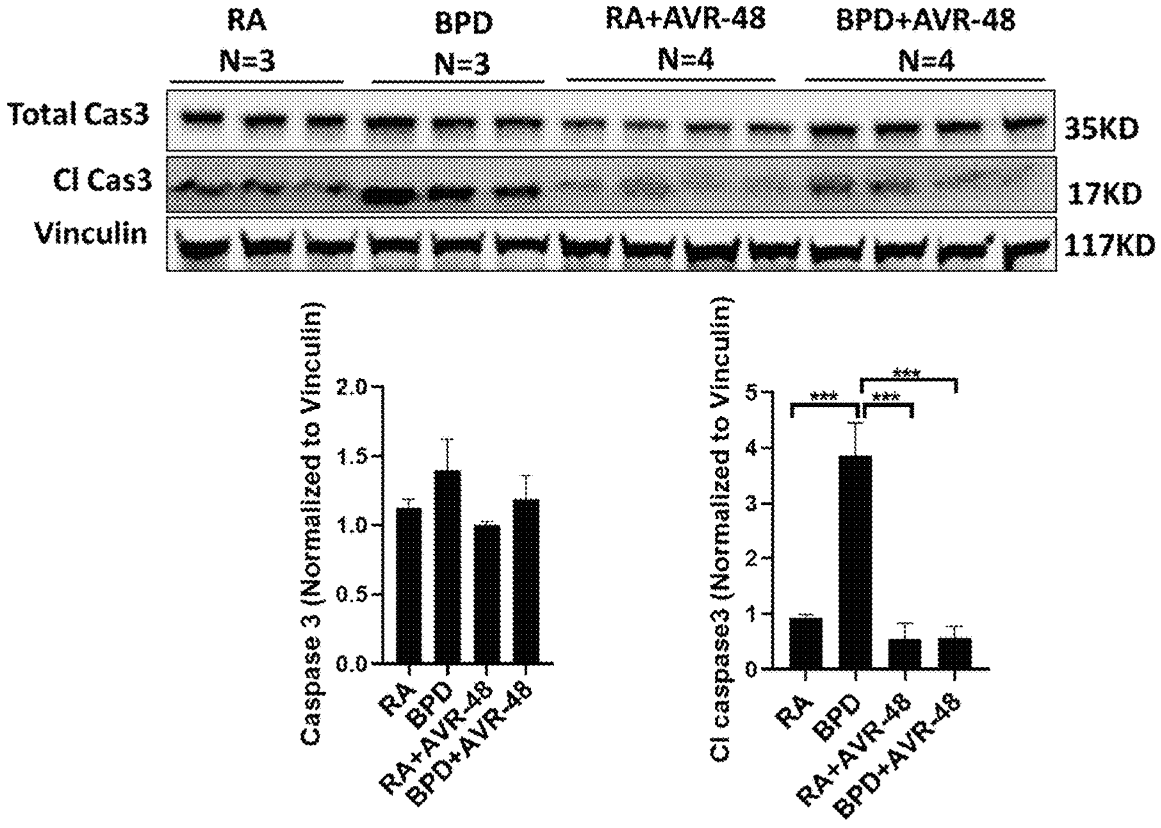

AVR-48 restored lung morphology and improved alveolar cellular physiology. After assessment of the safety profile of the AVR-48, and confirmation of the ideal dose to be used, the inventors then performed studies to evaluate the therapeutic effect on the lung in the experimental BPD mouse model, as previously described (Bhandari, Choo-Wing et al. 2008, Leary, Das et al. 2019, Das, Acharya et al 2020, Das, Curstedt et al 2020). BPD is characterized by enlarged simplified alveoli with large air sacs, thickened septum, and thin alveolar epithelium (FIG. 2A) accompanied by overall decrease in alveolar cell proliferation, decreased/dysregulated angiogenesis and increased cell death. All these features were restored after injection of 2 doses of AVR-48, IP (10 mg/kg) on days P2 and P4. The alveolar sacs, as evident from the chord length (FIG. 2B) and the septal thickness (FIG. 2C), regained their normal shape and size in the treated group, comparable to that of RA controls. The radial alveolar counts (RAC), which is decreased in the diseased condition, was also improved after AVR-48 treatment (FIG. 2D). The total inflammatory cells present in the BALF (FIG. 3A) and the total protein content (FIG. 3B)—both increase in BPD, was decreased after treatment with AVR-48. There was a revival in cell proliferation (as evident from Ki67 immunostaining; FIG. 4A). To assess cell specificity, the inventors focused on Type I and Type II alveolar epithelial cells (AECs), as they are most relevant to the process of alveolarization, as described in the manuscript. The inventors utilized the receptor for advanced glycation end-products (RAGE) as the preferred marker for Type I AECs [26, 27] and surfactant protein (SP)-C for the Type II AECs [28, 29]. Due to Ki67 and SP-C being raised in the same species, we used proliferating cell nuclear antigen (PCNA) expression—a well-established marker of cell proliferation because cells remain a longer time in the G1/S phase when proliferating—as a preferred marker for proliferating cells. The number of cells co-localizing with surfactant protein (SP)-C and PCNA were less in the BPD group as compared to RA, RA+AVR-48 and BPD+AVR-48 groups (FIG. 4B). There were few cells which were double positive for PCNA as well as RAGE in the RA and RA+AVR-48 groups (FIG. 4C). On the other hand, although the number of RAGE+ve cells were decreased in the BPD group as compared to RA, RA+AVR-48 and BPD+AVR-48 groups, these did not co-localize with PCNA in the BPD or BPD+AVR-48 groups (FIG. 4C). In addition, there was a decrease in cell death (as shown by TUNEL staining (FIG. 5A) and immunoblotting of cleaved caspase 3; FIG. 5B) after treatment with AVR-48, as compared to the BPD group.

Figure 6A:
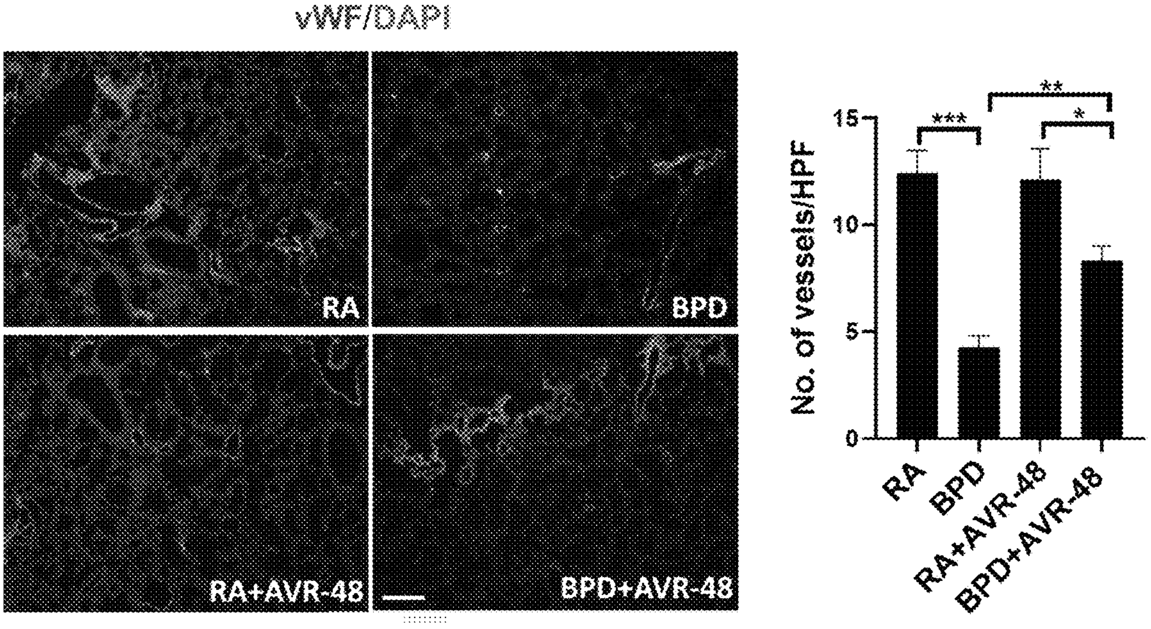
FIGS. 6A and 6B show that AVR-48 promotes vascular development.
Figure 6B:
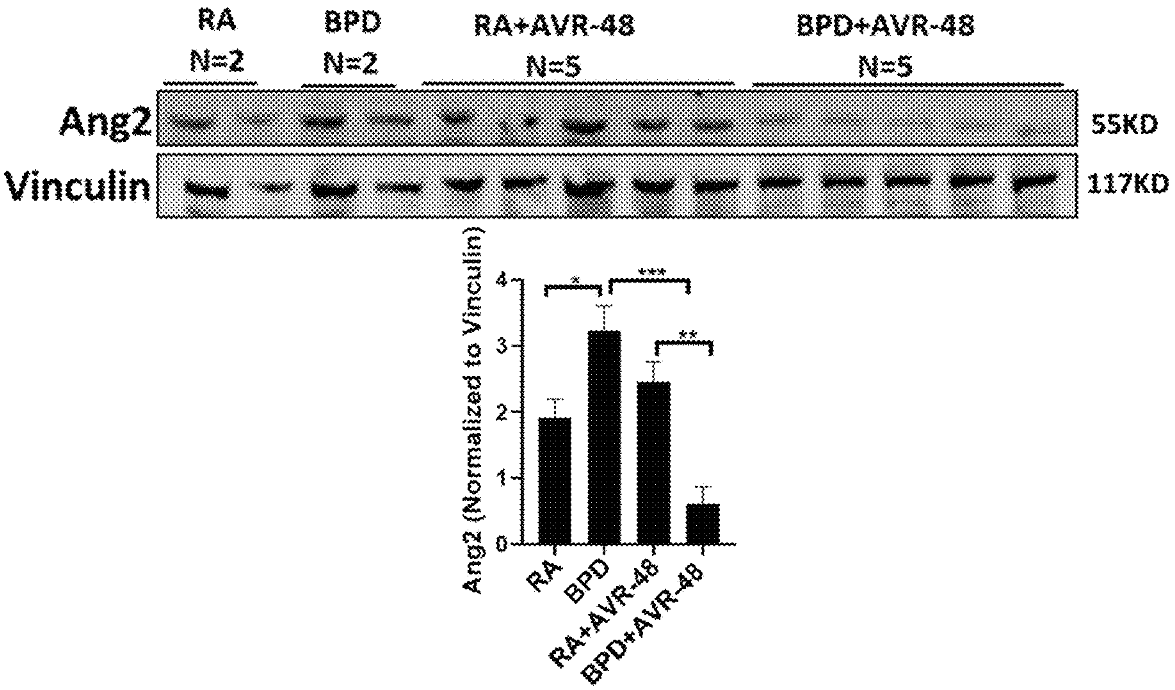

The blood vessels, which are usually disrupted in BPD, showed improvement (as was evident from vWF immunostaining; FIG. 6A). Angiopoetin 2 (Ang2), which is increased in BPD [30, 31], was significantly decreased after treatment with AVR-48 (FIG. 6B), thus suggesting that AVR-48 treatment may be able to stabilize vascular leak and promote sprouting neo-angiogenesis.

AVR-48 did not have any adverse effect with surfactant. Since exogenous surfactant is used as the standard of care in neonatal intensive care units (NICUs) to prevent and manage RDS in early life of preterm neonates, the inventors wanted to test the impact (if any) of the concomitant use of AVR-48 with surfactant. Although mice are surfactant sufficient (unlike preterm human infants who are surfactant deficient), the inventors delivered Curosurf® (CS; a commercially available surfactant from Chiesi Parma, Italy) IN, to mimic the intratracheal (IT) instillation in human babies, followed by AVR-48 injected IP, to demonstrate if AVR-48 has good compatibility with CS, when given as adjuvant treatment. There was no change in the total cells or the total protein content in BALF between the BPD groups treated with AVR-48 alone or CS alone or in combination with CS and AVR-48, as compared to untreated BPD group alone.

AVR-48 increases lung TLR4 expression. From in silico molecular modelling and in vitro studies, it was found that AVR-48 has a binding affinity for toll-like receptor (TLR) 4 and therefore decreases the expression of TLR4 level in THP-1 human monocytic cells with an EC50 of 76.0 nM after 48 h of treatment, as determined by ELISA (data not shown). In the clinical scenario, neonates are vulnerable to infection due to weakened immunity and rely on their innate immune system to combat any externally acquired infection and TLR4 is a crucial component of the neonatal immune system. To determine TLR4 expression in the lung with AVR-48 treatment, western blot was performed on whole lung homogenates. Surprisingly, there was an increase in the expression of TLR4 in the lungs after treatment. Although AVR-48 decreases TLR4 expression in a cell line, it increases TLR4 in the present in vivo BPD murine model.

AVR-48 treatment decreases the number of BAL cells in BPD pup lung where a commercial TLR4 antagonist TAK 242 did not. (FIG. 9) showing differential activity.

Figure 7A:
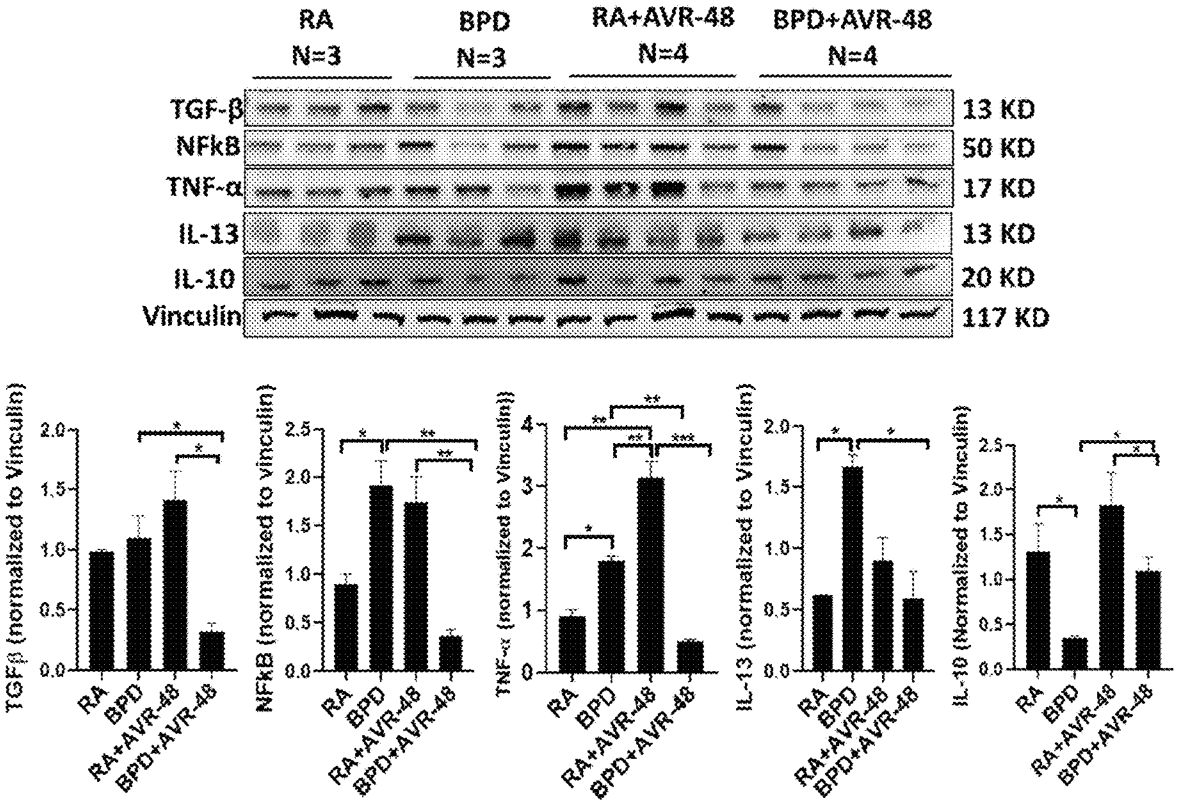
FIGS. 7A to 7C show that AVR-48 suppresses inflammation.
Figure 8A:
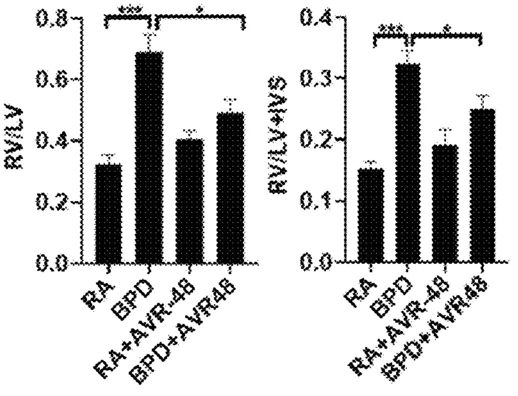
FIGS. 8A to 8C show that AVR-48 protects against BPD-PH.
Figure 8B:
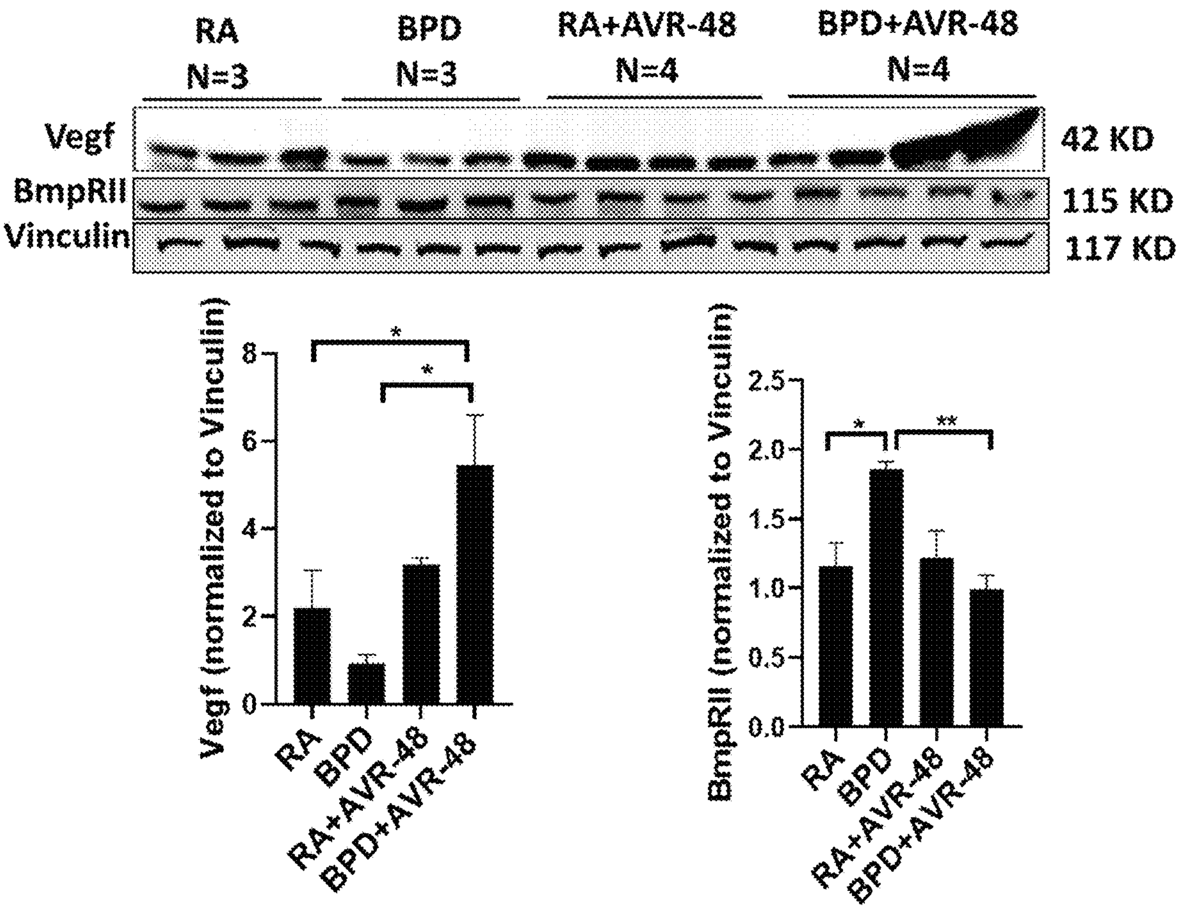
Figure 10:
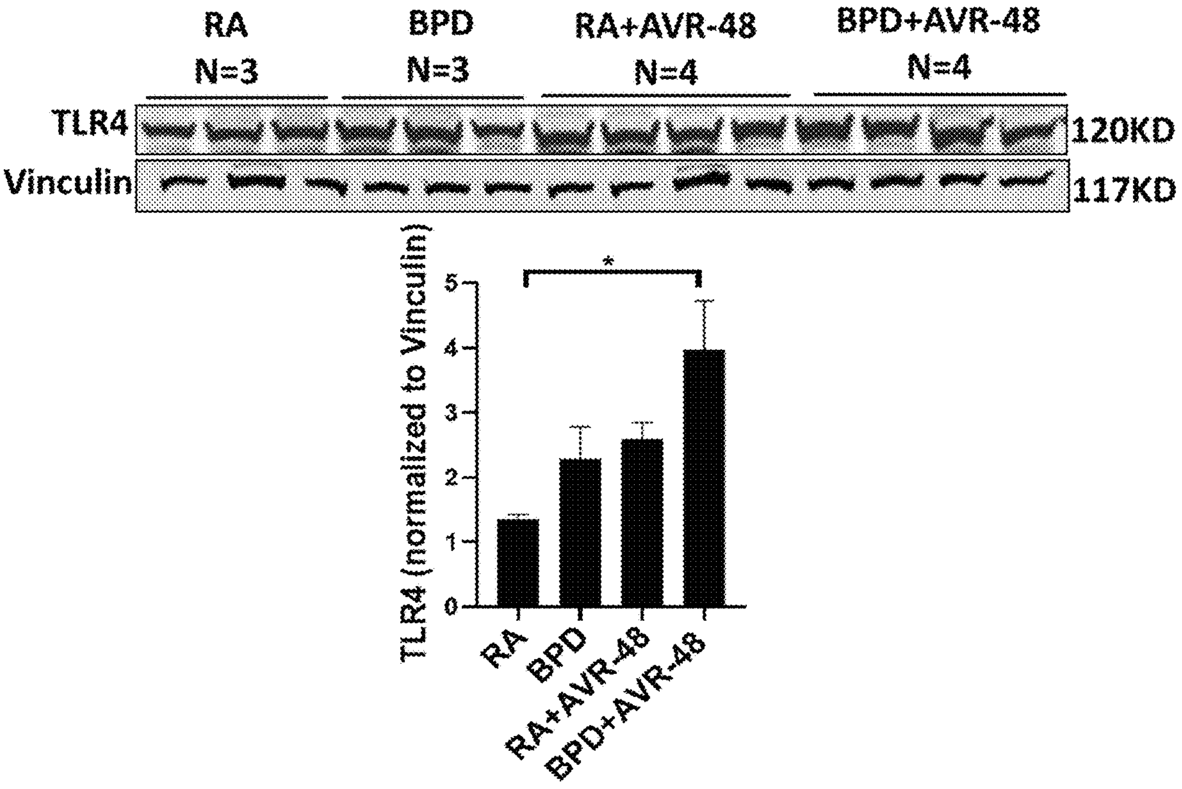
FIG. 10 shows the representative western blotting of lung homogenates with corresponding densitometric quantification (top right panel) of TLR4. Vinculin is the loading control and is the same one as shown in FIGS. 7A and 8B because the same samples were used.

FIG. 10 shows the representative western blotting of lung homogenates with corresponding densitometric quantification (top right panel) of TLR4. Vinculin is the loading control and is the same one as shown in FIGS. 7A and 8B because the same samples were used.

Figure 11:
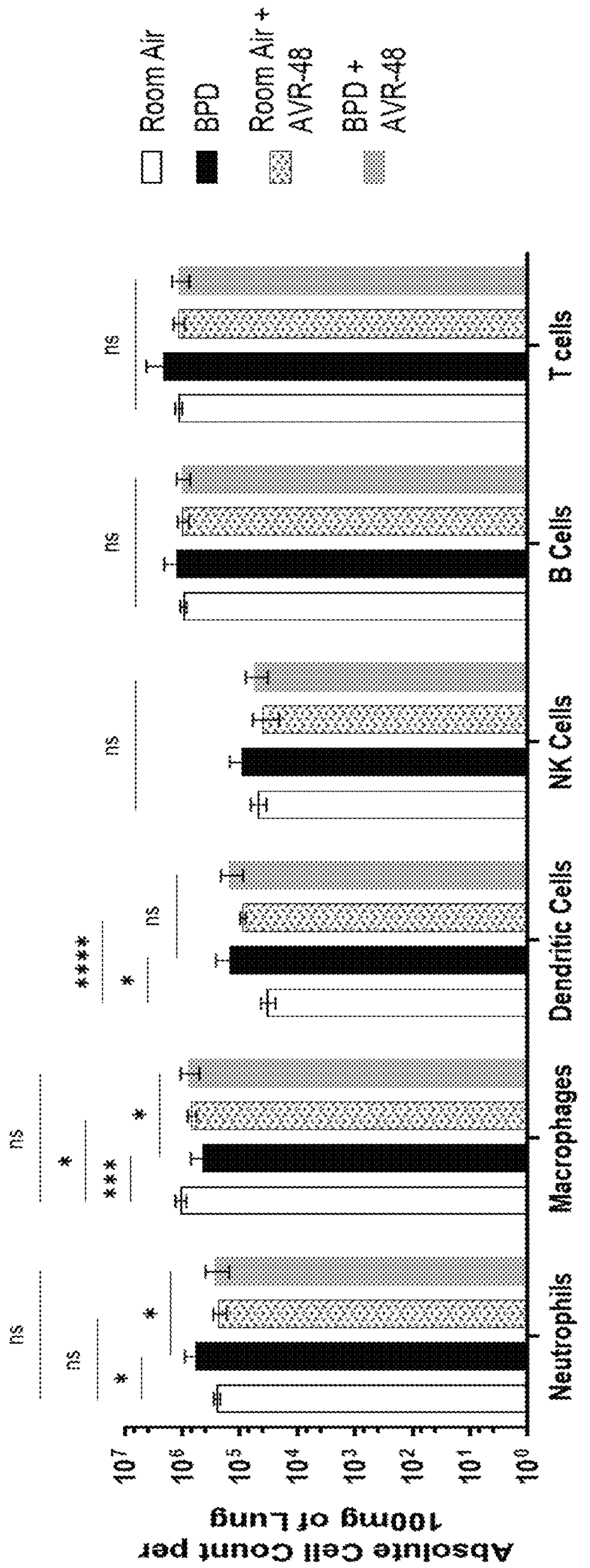
FIG. 11 shows that AVR-48 normalizes two important innate immune cell populations in animals with BPD. There was a significant increase in neutrophils and dendritic cells, but a decrease in macrophages, in the BPD versus RA groups in the lung. AVR-48-treated RA animals had a slight, but statistically significant, decrease in macrophages and increase in dendritic cells in the lung, compared to RA animals. AVR-48 treated BPD animals had decreased neutrophils and increased macrophages compared to untreated BPD animals, and these cell populations were at similar levels as the RA control group. *p<0.05; ***p<0.001; ns: not significant. RA: room air; BPD: Bronchopulmonary dysplasia; TLR: toll-like receptor; N=5-8.

AVR-48 normalizes two important innate immune cell populations in animals with BPD. Based on the affinity of AVR-48 for TLR4 and the increased TLR4 expression in AVR-48 treated BPD animals, the inventors determined if there would be an impact on immune cell recruitment to the lung interstitium. Flow cytometry was performed to determine absolute numbers of key immune cell populations in the lung of neonatal mice pups from AVIS-48-treated and untreated animals in the RA and BPD groups. The cell populations were identified as follows: macrophages ($CD45^+CD11b^+$ $Ly6G^-F4/801$, dendritic cells ($CD45^+$ $CD11c^+CD103^+MCHII^{high}$) neutrophils ($CD45^+CD11b^+$ $Ly6G^+$), B cells ($CD3^-CD19^+$), T helper cells ($CD3^+CD4^+$), cytotoxic T lymphocytes ($CD3^+CD8^+$) and NK cells ($CD3^-$ $NIK1.1^+$), These cell populations were chosen to identify both innate and adaptive immune cell populations. First, to determine the impact of AVR-48 alone on immune cell recruitment to the lung, RA animals were compared to AVR-48-treated RA animals, AVR treated RA animals had a slight, but statistically significant, decrease in macrophages and increase in dendritic cells in the lung. All other cell populations were similar (FIG. 11). Therefore, AVR-48 by itself had a minimal impact on the immune cell composition in the lung.

In agreement with the published literature and prior studies (Sureshbabu, Syed et al. 2016, Syed, Das et at 2017, Gilfillan, Das et al. 2020) there was a significant increase in neutrophils (Sun, Chen et al. 2019) and dendritic cells (De Paepe, Hanley et al. 2011) in the BPD group over the RA group. Next, AVR-48 treated and untreated BPD animals were compared. Interestingly, AVR-48 treated BPD animals had decreased neutrophils and increased macrophages compared to untreated BPD animals, and these cell populations were at similar levels as the RA control group. Therefore, AVR-48 normalized two important innate immune cell populations in the setting of BPD.

Figure 7B:
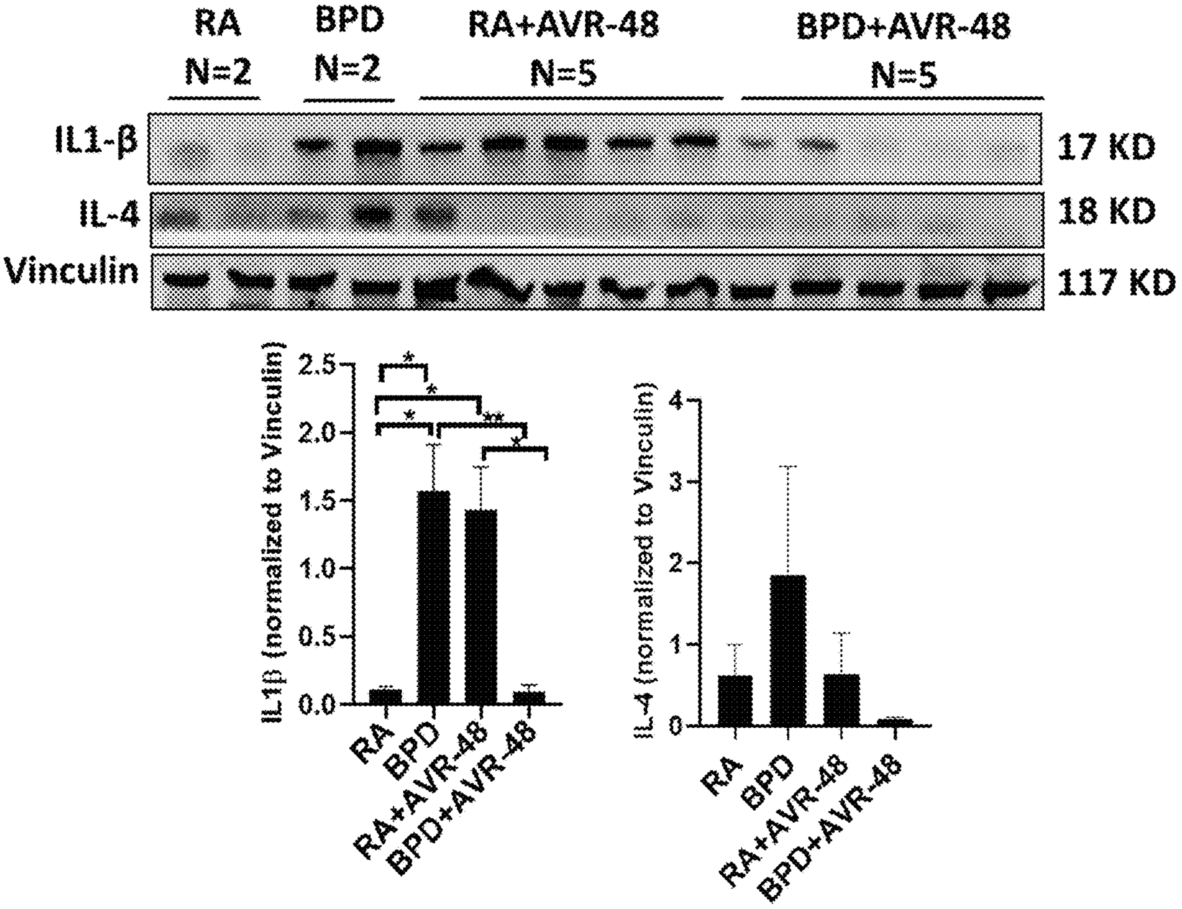
Figure 7C:
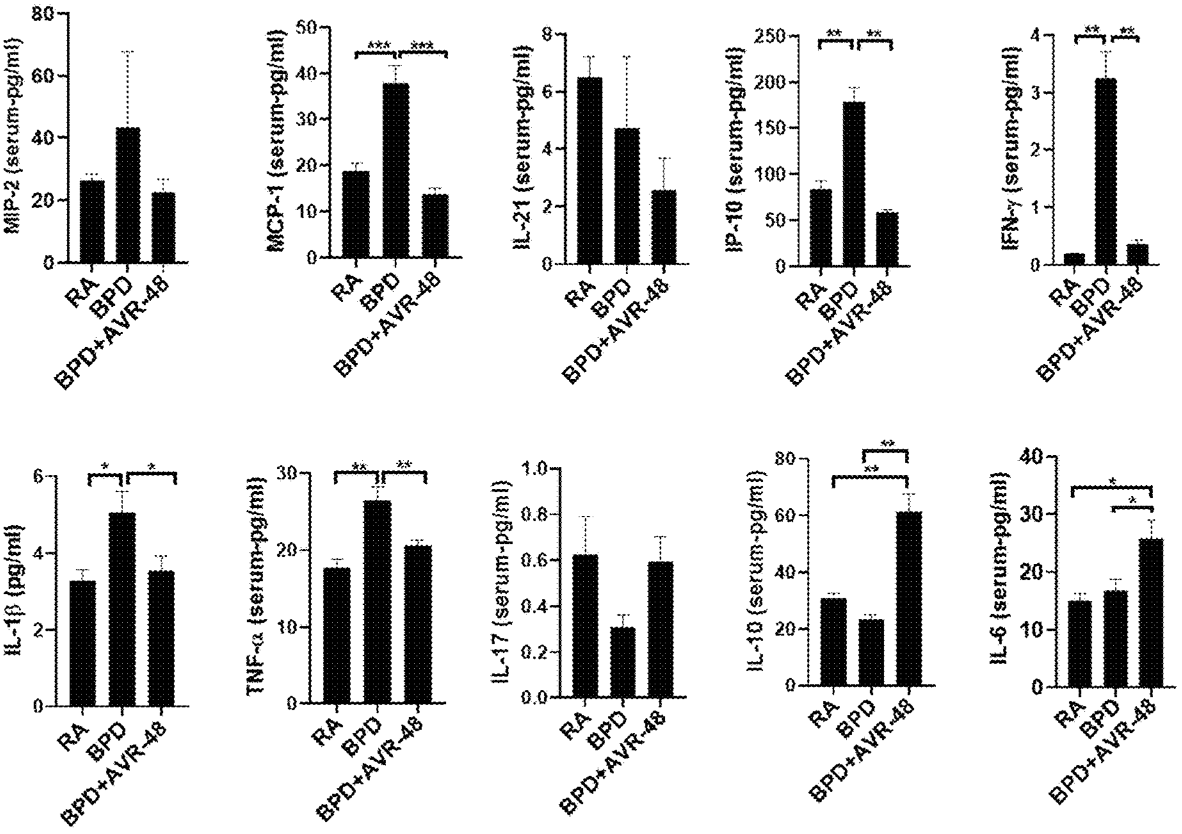

AVR-48 suppresses inflammation in the lungs by decreasing the pro-inflammatory, and increasing anti-inflammatory cytokines. Based on this difference in neutrophil and macrophage balance with AVR-48 treatment and the significant improvement in important metrics for BPI) severity (FIG. 2A), the inventors hypothesized that inflammatory cytokine production would be improved in the AVR-48 treated animals. Alveolar inflammation is one of the hallmark features in the pathogenesis of BPD. As reported by the present inventors (Bhandari 2002, Bhandari and Elias 2006) and others (Speer 2006), several cytokines and chemokines are upregulated in BPD. Upon treatment with AVR-48, there was a marked decrease in the master inflammatory transcription factor nuclear factor kappa B (NtkB), and some pro-inflammatory cytokines tumor necrosis factor (TNF)α, interleukin (IL)-13, and IL-1β, which are otherwise dramatically increased in BPD group, as compared to RA controls in lung homogenates (FIGS. 7A-B). On the contrary, the anti-inflammatory cytokine IL-10 increased upon treatment, which was considerably decreased in BPD group (FIG. 7A), as was evident by western blotting. Similar results were also obtained from lung lysates (data not shown) and blood serum by HASA assay. Some of the pro-inflammatory cytokines such as monocyte chemoattractant protein (MCP)-1, interferon gamma induced protein (IP)-10, interferon (IFN)γ, IL-1β and TNFα were significantly upregulated in the serum in the BPD group as compared to RA controls and decreased to normal levels after treatment with AVR-48 (FIG. 7C). The RA+AVR-48 group was not included as the samples were not available at the time of doing these assays. IL-10 was markedly increased after drug treatment in the BPD group (FIG. 7C). Together, these data indicate that AVR-48 does not impact immune cell recruitment to the lung in the setting of BPD. However, AVR-48 effectively modulates inflammatory and anti-inflammatory cytokine production, shifting treated animals in favor of an anti-inflammatory environment, which potentially improves the lung morphometry.

Figure 8C:
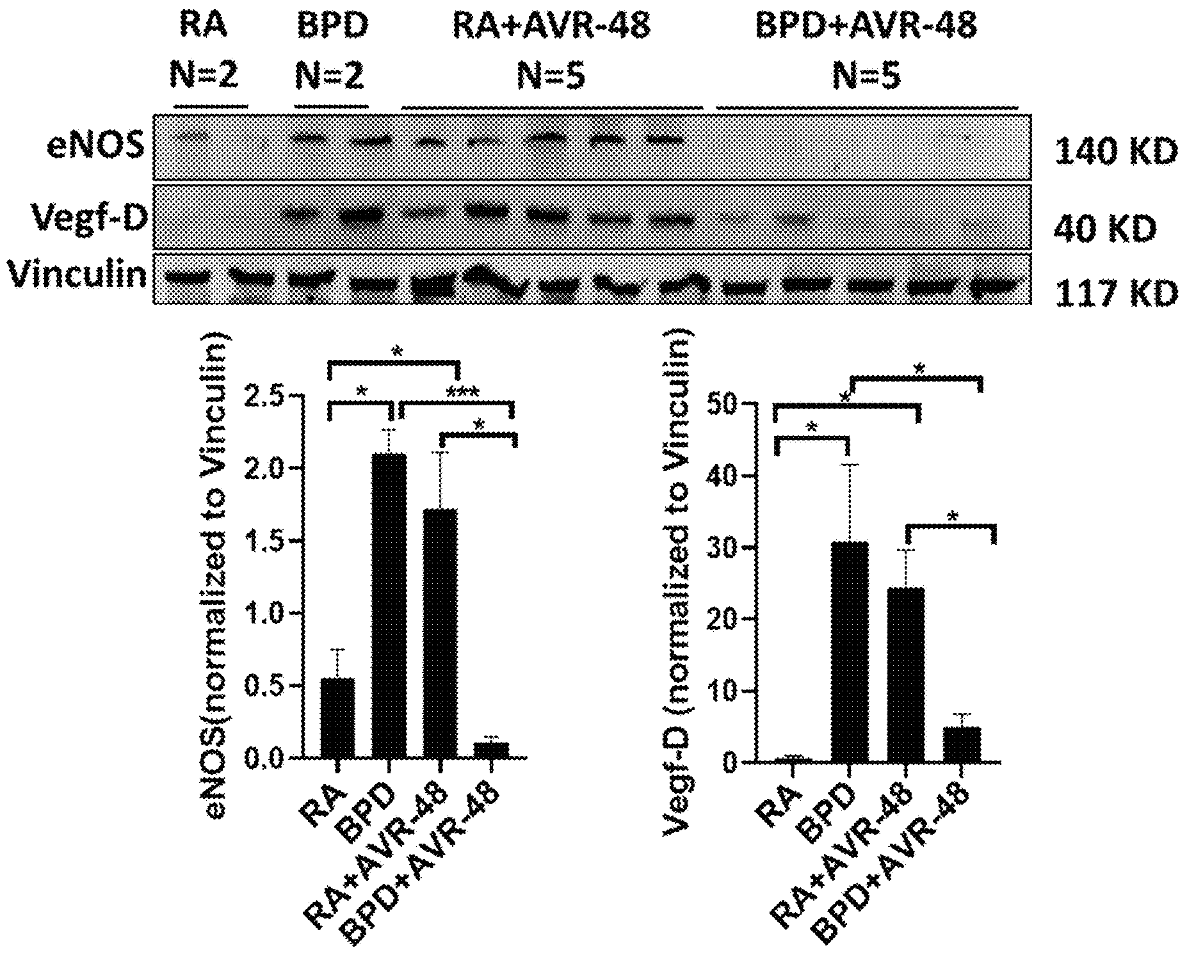

AVR-48 protects the lungs from progressing towards BPD-PH. BPD-PH is characterized by abnormal vascular remodeling and rarefication of the pulmonary vasculature leading to vascular growth arrest which eventually leads to increased pulmonary vascular resistance and right heart failure (Hansmann, Sallmon et al. 2021). A similar effect is also seen in mouse models of experimental BPD, as reported by the present inventors, previously (Sun, Choo-Wing et al. 2013, Sureshbabu, Syed et al. 2016, Syed, Das et al. 2017, Leary, Das et al. 2019). There is hypertrophy of the right ventricle (RV) with an increase in the thickness of interventricular septum (IVS). RV/left ventricle (LV) and Fulton's Index (RV/LV+IVS) is higher in the BPD group as compared to RA, but is decreased significantly after treatment with AVR-48 in the BPD group (FIG. 8A). There was no change in the ratio in the RA group treated with the drug, which was similar to RA control group (FIG. 8A). Total vascular endothelial growth factor (Vegf) was less in the BPD group, which increased considerably after treatment with AVR-48 (FIG. 8B); on the other hand, endothelial nitric oxide synthase (eNOS) (Potter, Kuo et al. 1999), and bone morphometric protein receptor (BmpR)II which are known to be elevated in BPD (Alejandre-Alcazar, Kwapiszewska et al. 2007, Chen, Orriols et al. 2017) were significantly decreased in the AVR-48 treated group (FIG. 8C). Vegf-D has not been reported earlier in mouse models of BPD, to the best of the inventors' knowledge, and in the present study, the inventors demonstrate an increase in the expression of Vegf-D protein in BPD, which decreases after treatment. All the above data clearly shows that AVR-48 is able to rescue the BPD cardiopulmonary phenotype.

FIG. 11 shows that AVR-48 normalizes two important innate immune cell populations in animals with BPD. There was a significant increase in neutrophils and dendritic cells, but a decrease in macrophages, in the BPD versus RA groups in the lung. AVR-48-treated RA animals had a slight, but statistically significant, decrease in macrophages and increase in dendritic cells in the lung, compared to RA animals. AVR-48 treated BPD animals had decreased neutrophils and increased macrophages compared to untreated BPD animals, and these cell populations were at similar levels as the RA control group. *$p<0.05$; ***$p<0.001$; ns: not significant. RA: room air; BPD: Bronchopulmonary dysplasia; TLR: toll-like receptor; N=5-8.

Despite several advances in neonatal lifesaving methodologies, BPD continues to be one of the most devastating life-threatening conditions in preterm babies. Repeated inflammatory insults from antenatal complications and postnatal consequences worsen the lung phenotype. BPD-PH further contributes significantly to the severe morbidity and mortality. However, if prevented early, this condition can be mitigated to improve the respiratory status and developmental delays in childhood of these preterm infants. The inventors recently reported that AVR-48 decreases severe lung inflammation in LPS-, hyperoxia- and CLP-induced ARDS in adult mice while AVR-25, another close analog of AVR-48, can prevent lung injury in the neonatal mouse model of experimental BPD (Das, Acharya et al. 2020). In order to facilitate bulk manufacture, and improve physicochemical properties, the inventors have optimized the chemical series and identified AVR-48 as a better lead than AVR-25. In this study it is shown that AVR-48 is prevents experimental BPD by alleviating lung injury and BPD-PH. As BPD is a neonatal disease, the inventors made every effort to make the compound nontoxic by synthesizing it in the purest form during formulation and noted that a high dose of 100 mg/kg did not have any toxic effects in the visceral organs. Most importantly, from the dose response efficacy and toxicokinetic studies, it was determined that the therapeutic index for AVR-48 in the juvenile mouse was 20-fold, based on the minimum efficacious dose of 5 mg/kg/day vs NOAEL of 100 mg/kg/day, which is a highly desirable profile for a lead drug candidate.

Figure 12A:
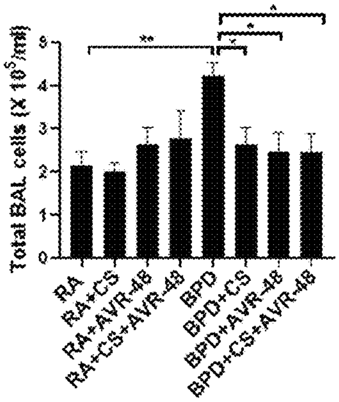
FIGS. 12A and 12B show that AVR-48 is compatible with exogenous surfactant.
Figure 12B:
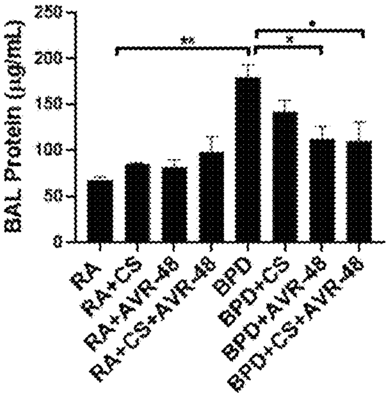

As surfactants are the standard of care in NICUs all over the world, the inventors tested AVR-48 administered adjuvantly with CS in mouse pups to rule out any cross reactivity with surfactant, in vivo. There was no adverse effect on the interaction between the drug and CS. The chord length was normal and total cells and protein content in the BALF were similar to that of the groups treated with AVR-48 alone or with CS alone (FIG. 12A and FIG. 12B).

Figure 13A:
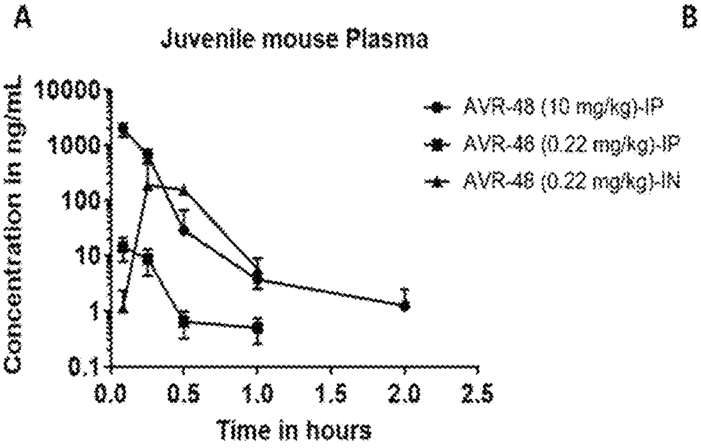
FIGS. 13A and 13B show the bioavailability of the drug in mouse pups (FIG. 13A) Mean AVR-48 concentrations in the plasma.
Figure 13B:
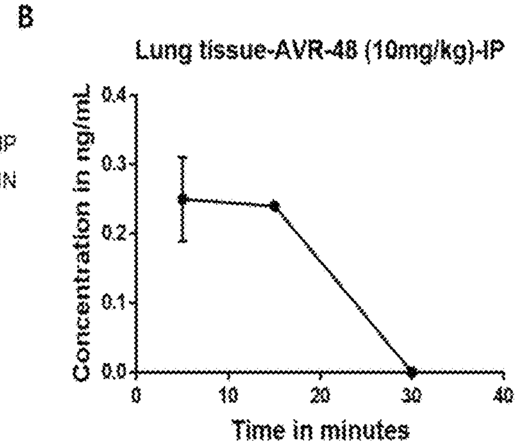

FIGS. 13A and 13B show the bioavailability of the drug in mouse pups (FIG. 13A) Mean AVR-48 concentrations in the plasma. (FIG. 13B) Mean AVR-48 concentrations in the lungs after IN or IP administration IP: intraperitoneal; IN: intranasal; N=6.

Figure 14A:
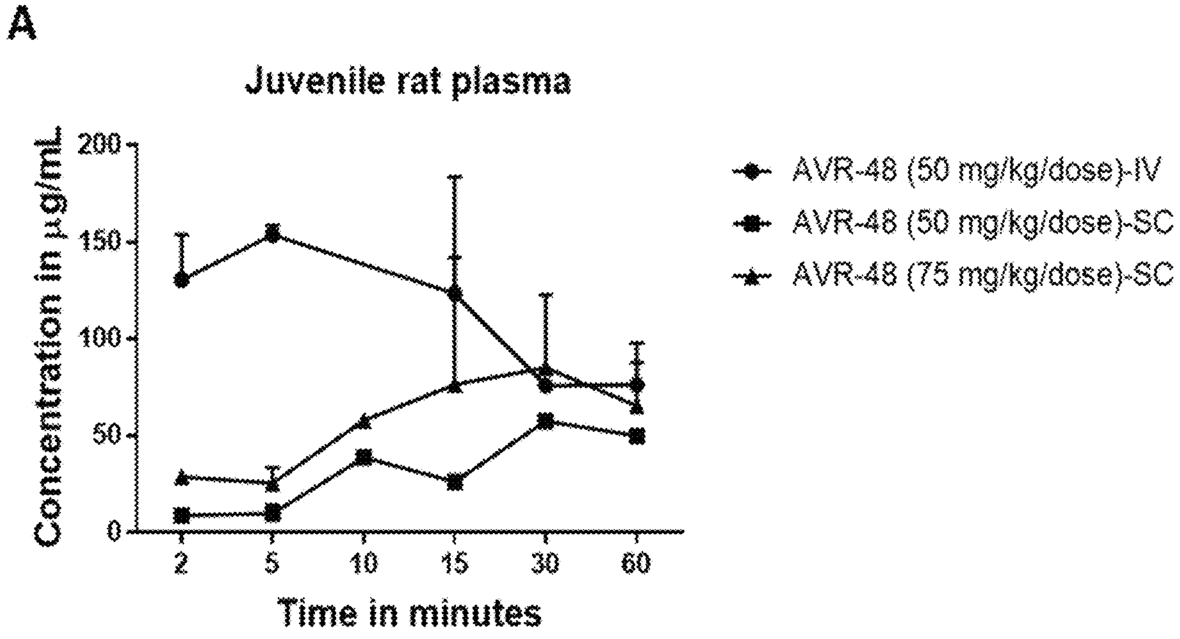
FIGS. 14A and 14B show the bioavailability of the drug in rat pups (FIG. 14A) Mean AVR-48 concentrations in plasma.
Figure 14B:
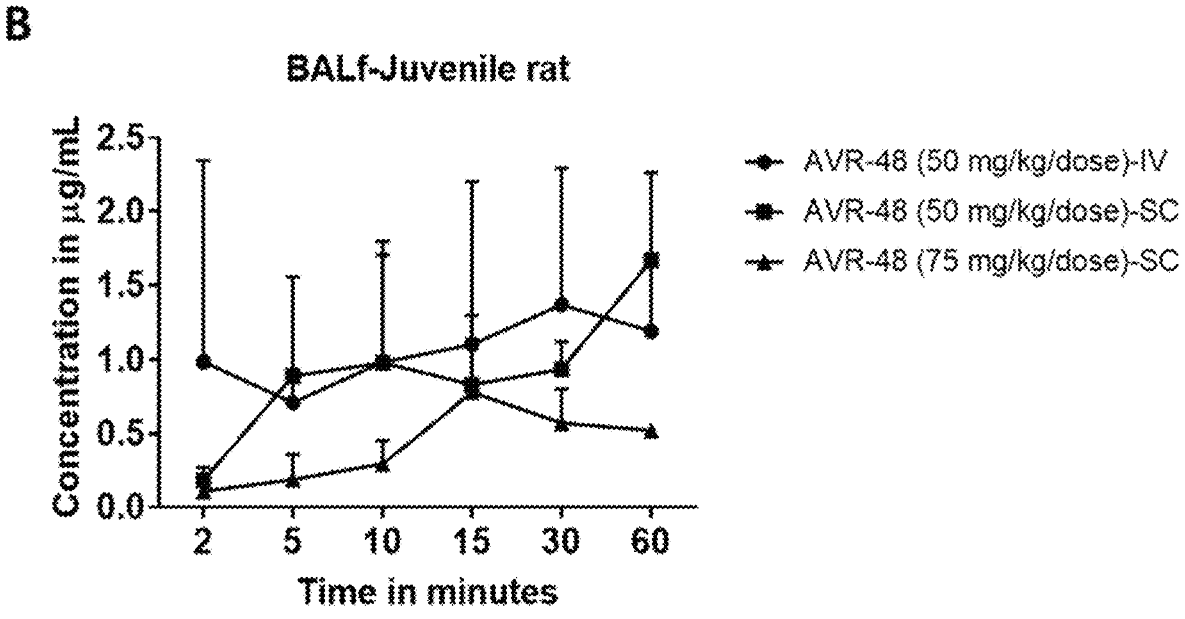

FIGS. 14A and 14B show the bioavailability of the drug in rat pups (FIG. 14A) Mean AVR-48 concentrations in plasma. (FIG. 14B) Mean AVR-48 concentrations in the BAL following IV and SC administration. IV: intravenous; SC: subcutaneous; BALf: bronchoalveolar lavage fluid; N=6.

Figure 15:
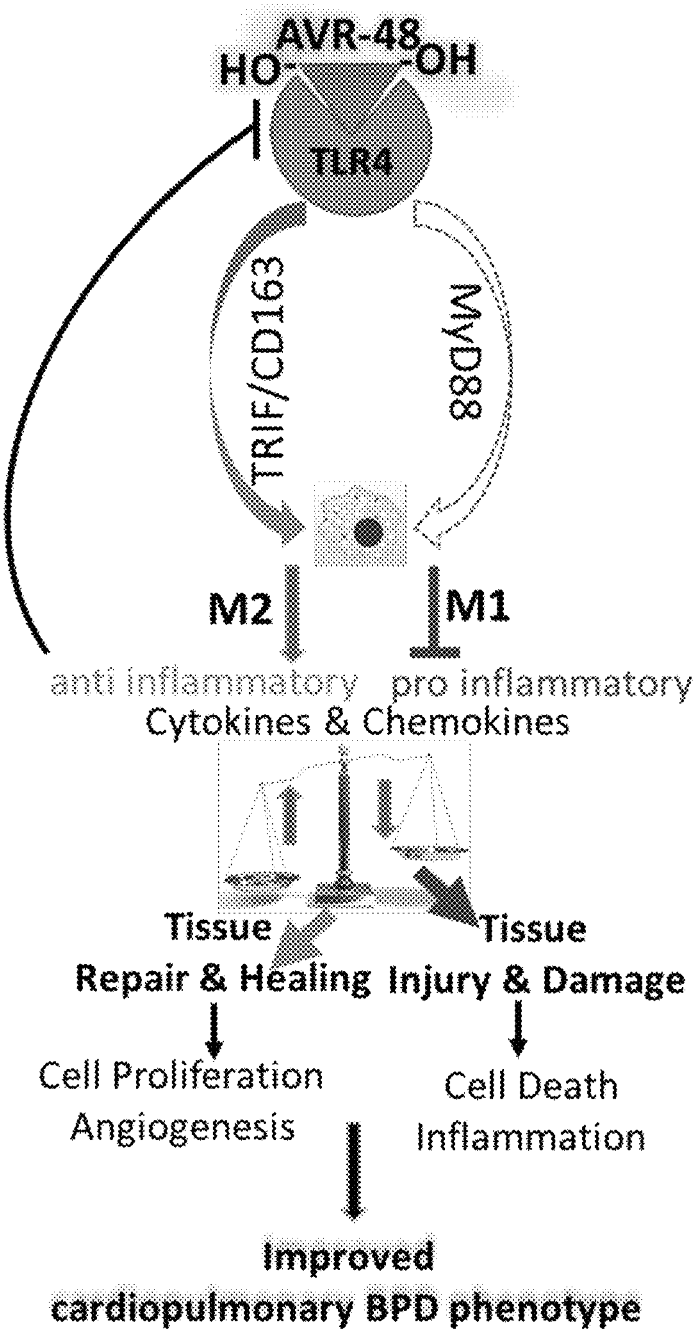
FIG. 15 shows a proposed mechanism of action of AVR-48 in neonatal lungs. AVR-48 after binding to TLR4 triggers the TRIF pathway to activate the M2 macrophages via the alternate pathway to produce IL-10, which in turn negatively regulates TLR4 to downregulate the MyD88 pathway so as to decrease the synthesis of a myriad of pro-inflammatory cytokines and chemokines by suppressing the M1 macrophages that are produced via activation of the classical pathway during BPD. This combinatorial effect results in decreasing tissue injury and increasing tissue repair and healing by maintaining a balance between M2 and M1 macrophages towards a favorable outcome with overall improvement of the BPD cardiopulmonary phenotype.

Increased inflammation, decreased/dysregulated angiogenesis, increased cell death and decreased cell proliferation are some of the key features associated with the pathogenesis of BPD. AVR-48 was able to suppress inflammation by inhibiting TGFβ, NFkB, TNFα, IL1β, MCP-1, IP-10, IFNγ—all of which are mediators of inflammation; in contrast, the anti-inflammatory cytokine IL-10 was upregulated upon treatment. Although AVR-48 has a binding affinity for TLR4, there was increased TLR4 expression after AVR-48 treatment. TLR4 is activated following hyperoxia exposure in the neonatal brain (Liu, Jiang et al. 2015) and lung (Chen, Li et al. 2015), which leads to inflammatory cytokine release. Potentially, AVR-48 may partially bind to TLR4, which may activate the TIR-domain-containing adapter-inducing the interferon-β (TRIF) pathway, which results in increased production of IL-10 and decreased production of MyD88-dependent inflammatory cytokines, such as TNFα and IL1β (Tam, Coller et al. 2021). IL-10 acts as a suppressor of TLR4 and so this increased IL-10 might serve as a negative feedback loop for TLR4 activation (Curtale, Mirolo et al. 2013). By way of explanation and in no way a limitation of the present invention, the inventors hypothesize that AVR-48 may act as a feedback modulator as a result of which the binding of AVR-48 with TLR4 enhances resident/anti-inflammatory macrophages M2 over inflammatory macrophages M1 via an alternate pathway activation, as has been shown with chitohexaose in a LPS-induced sepsis model (Panda, Kumar et al. 2012). It is further hypothesized that AVR-48 may act as a feedback modulator which acts through the TRIF pathway and initiates production of IL-10. This IL-10 production then suppresses TLR4 and downregulates MyD88-dependent production of pro-inflammatory cytokines (FIG. 15).

PH is often associated with BPD and this condition has also been observed in mice models of experimental BPD. Vegf, which is considered a classical marker for BPD-PH (Abman 2010) was decreased while eNOS was increased in BPD. For the first time, in this study the inventors report that Vegf-D, which is a lymphangiogenic growth factor, is increased in BPD. Both eNOS and Vegf-D are substantially decreased after treatment with AVR-48.

Mutations in BmpRII are associated with heritable pulmonary arterial hypertension (PAH) and there are multiple reports which shows that in adult PAH, there is a decrease in BmpRII. However, the role of BmpRII in neonatal hyperoxia and BPD-PH has received less attention. While Alejandre-Alcazar et al, show that BmpRII is significantly decreased after hyperoxia exposure (85% $O_2$ for 14 or 21 days) in P10 or P14 mouse pups (Alejandre-Alcazar, Kwapiszewska et al. 2007), Chen et al show that BmpRII is significantly increased in rat pups (P10) after hyperoxia (100% $O_2$) for 10 days exposure (Chen, Orriols et al. 2017). Interestingly, Yee et al, report that BmpRII decreases in the adult mice when these mice were exposed to hyperoxia in the neonatal stage; they do not have any data regarding the expression of BmpRII after hyperoxia exposure in the neonatal stage (Yee, White et al. 2011). Interestingly, all the 3 groups have reported only the mRNA expression of BmpRII because the antibodies for BmpRII did not work in their hands to evaluate the protein levels of the same. On the contrary, the inventors have shown that the protein expression of BmpRII is increased following hyperoxia exposure, which was subsequently downregulated after treatment with AVR-48. It is to be mentioned here that in many instances, the mRNA levels do not correlate with the protein levels. Hence, the role of BmpRII in hyperoxia-induced BPD-PH needs to be evaluated more elaborately in the neonatal context.

Based on the results of this study, AVR-48 (compound 8) can be used as a prophylactic therapy for an orphan disease like BPD and BPD-PH, for which there is no prevention or cure to date.

Animals. C57BL/6J mice were purchased from The Jackson Laboratory (Bar Harbor, ME, USA) and were maintained in a breeding colony at Drexel University, Philadelphia, PA, USA. Animal procedures were performed in accordance with the NIH Guide for the Care and Use of Laboratory Animals and were approved by the Institutional Animal Care and Use Committee (IACUC) of Drexel University Philadelphia, PA (Protocol No. 20706). Neonatal rat pups born from female pregnant Sprague Dawley Crl:CD (SD) rats (Charles River Laboratories, St-Constant, QC, Canada) were used for the toxicology and PK studies to evaluate safety, determine the maximum tolerated dose (MTD) and the PK profile of AVR-48. A minimum 6-day acclimation period was allowed between receipt of the animals and the start of treatment to accustom the rats to the laboratory environment. All rat studies were approved by the IACUC of ITR Laboratories, Canada (Protocol No. 74691).

Chemicals and Reagents. The synthesis and structural characterization of compound AVR-48 and the PLGA encapsulated AVR-48 were conducted in the laboratory of AyuVis Research Inc., following their in-house procedures (PCT No. WO2020010090). The synthesis, characterization and drug release of AVR-48 nanoparticle suspension is provided in the supplemental section. Endotoxin-free phosphate-buffered saline (PBS) was purchased from Sigma-Aldrich Inc., St. Louis, MO, USA.

Formulation of AVR-48 for efficacy and toxicokinetic studies. For the mouse dose response efficacy studies, AVR-48 was reconstituted in 0.9% sterile normal saline to give a final dose concentration of 1.0 mg/kg, 2.5 mg/kg, 5.0 mg/kg and 10 mg/kg as a colorless solution, and injected IP (30 μl) on P2 and P4. The PLGA encapsulated AVR-48 or the GFP-tagged analog was resuspended in deionized sterile water to make a nanosuspension with final dose concentration of 0.025, 0.05 and 0.11 mg/kg/drop. The surfactant Curosurf® (Cheisi Parma, Italy), available commercially, was delivered IN at a volume of 3 μl per nostril, on P2 and P4. For the toxicokinetic study of AVR-48 in rat pups, a formulation of 10% DMSO, 20% tetraglycol, 20% PEG 400, and 50% sterile water was made fresh before administration (Shah, Das et al. 2021).

Example 2. Hyperoxia Treatment

For the hyperoxia experiment, newborn pups were exposed to 100% hyperoxia (P0), along with their mothers, in cages in an airtight Plexiglas chamber (OxyCycler; Biospherix, Redfield, NY, USA) as described previously by the present inventors (Syed, Das et al., 2017, Leary, Das et al. 2019, Das, Acharya et al. 2020, relevant portions incorporated herein) for 4 consecutive days (till P4) and removed to RA on P5 to be recovered till P14, so as to emulate the human BPD condition. All pups were sacrificed on P14 for further experimental analyses. The pups without any hyperoxia exposure served as the corresponding RA (normoxia) controls.

Example 3. AVR-48 Treatment Decreases Respiratory Severity and Improves Lung Function in the Pre-Term Lamb BPD Model Next, the inventors tested the drug exposure to lung, brain, and plasma in a higher animal model that mimics preterm (PT) human infants and demonstrate the efficacy of the compounds taught herein to prevent BPD via IV dosing. A unique PT lamb model, developed by Dr. Albertine (University of Utah), was used to emulate the clinical setting for PT human infants with respiratory failure related to premature birth before the lungs are mature enough to support extra-uterine life. Both the PT lamb model and PT human infants are whole-organism physiological beings that have the setting of PT birth and prolonged ventilation support with oxygen-rich gas because of respiratory failure related to lung structural and functional immaturity, including surfactant deficiency. Ventilation support with oxygen-rich gas is for days, weeks, months, and is associated with co-morbidities of the brain, liver, distal ileum, and kidney injury, and inadequate nutrition and poor postnatal growth. This PT lamb model for BPD continues to provide mechanistic insights during the evolution of BPD (Joss-Moore, Metcalfe et al. 2010), development of multiple-organ dysfunction (Albertine 2012, Abdullah, Seidel et al. 2016), and long-term structural and functional impairments (Dahl, Bowen et al. 2018).

A dose range-finding study was conducted with the goal of treating two PT lambs with either a vehicle control or low, mid, and high doses of AVR-48 (compound 8) by twice daily intravenous infusions during 6 to 7 days of mechanical ventilation, followed by transition to noninvasive respiratory support (NIS) for 3 days, for a total of 10 days of management of these PT lambs. Compound 8 was not given during the period of noninvasive respiratory support to assess short-term persistence of effect of compound 8. The PK and PD parameters for compound 8 were also determined.

Detailed methods have been published previously by Reyburn et al. and Null et al (Reyburn, Li et al. 2008, Null, Alvord et al. 2014), relevant portions incorporated herein by reference. All protocols have been adhered to APS/NIH guidelines for animal research and have been approved by the Institution Animal Care and Use Committees (IACUC) at the University of Utah. Lung injury in PT neonates, including PT lambs, that are mechanically ventilated (MV) is the classical picture of alveolar simplification. Alveolar simplification is evident as distended terminal respiratory units that have few secondary septa and thick, cellular mesenchyme. This pathology does not develop when non-invasive support is used, such as high-frequency nasal ventilation (HFNV)(Reyburn, Li et al. 2008, Null, Alvord et al. 2014). The inventors used 3 d mechanical ventilation because that is the minimum number of days (72 h) required to find altered expression of genes involved in alveolar formation, either pathophysiologically upregulated (e.g., elastin, inflammatory cytokines) or downregulated (e.g., vascular endothelial growth factor or VEGF and its functional receptor, surfactant apoproteins, insulin-like growth factor 1)(Pierce, Albertine et al. 1997, Albertine, Jones et al. 1999, Albertine, Dahl et al. 2010).

The modified PT lamb model used 6 d to 7 d of mechanical ventilation for respiratory management to identify temporal pathogenesis of the disease. The 6 d to 7 d of respiratory management period using invasive mechanical ventilator emulates the clinical corollary in NICUs today: PT infants who are supported for 6 d to 7 d have more difficulty being extubated (fail to be extubated) or kept from being reintubated (failed extubation). The goal was to find the tolerable dose, PK parameters, and identify preliminary efficacy.

Figure 9:
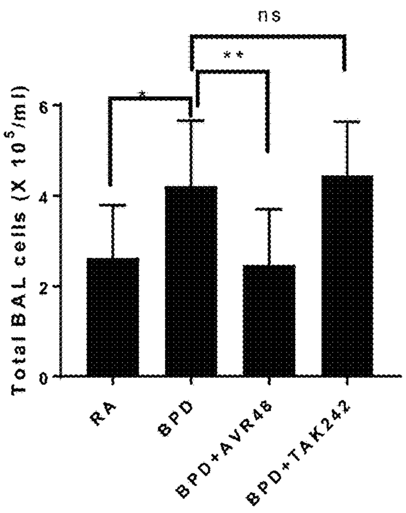
FIG. 9 shows the comparison of compound 8 (AVR-48) with a known TLR4 antagonist TAK 242. Treatment with AVR-48 (10 mg/kg) while significantly decreased the increase in total BAL cells that consisted of inflammatory macrophages and neutrophils from the BPD mouse lungs, TAK 242 treatment did not affect.

This PT lamb model for BPD continues to provide mechanistic insights during the evolution of BPD (Joss-Moore, Metcalfe et al. 2010), development of multiple-organ dysfunction (Albertine 2012, Abdullah, Seidel et al. 2016), and long-term structural and functional impairments (Dahl, Bowen et al. 2018). The respiratory severity score (RSS) which is predictive of severe BPD and death in clinic (Jung, Jang et al. 2019) is improved dramatically with 3.0 mg/kg being the highest efficacious dose (FIG. 9). An RSS≥3.0 at postnatal day 14 and an RSS≥3.6 at postnatal day 21 in PT babies are reliable values for predicting severe BPD or death.

A total 9 lambs were used for this study. One dose of Curosurf was given intratracheally to the PT lamb just after birth. Randomized doses of compound AVR-48 (8) (0, 0.1, 0.3, 1.0 and 3.0 mg/kg) were administered intravenously every 12 hr after the initial dose that will be given at 6 hr after delivery to n=2-4 lambs via slow intravenous injection. The beginning treatment at 6 hr post-delivery is selected to represent the human case where neonatologists attempt to allow an infant to breath without mechanical ventilation, if possible, and then begin invasive respiratory support as necessary. Whole blood was drawn from PT lambs at the time of delivery ("pre-dose"), immediately after dosing (IAD), at 15, 30, 45, and 60 min, and at 2, 4, 8, 12, 24, 48, 72, and 96 hr after the initial dose. Plasma extractions and bioanalysis of compound AVR-48 (8) were performed using a qualified bioanalysis method already developed by us. The PK parameters were calculated following both non-Compartmental Pharmacokinetic Modeling and population Pharmacokinetic Modeling as described by Roberts et al previously (Roberts, Stockmann et al. 2016). Blood was collected every 15 min for the first 90 min of postnatal life, followed by every 3 hours for 12 hours and then spaced at 1.5 d, 2.5 d, 3.5 d, 6.5 d, and 9.5 d for analysis of cytokines (Visconti, Senthamaraikannan et al. 2018) and VEGF levels (Albertine, Dahl et al. 2010). The blood samples also were analyzed for hematology and liver enzymes. After 6-7 d of mechanical ventilation, the lambs will be weaned from mechanical ventillation and weaned to non-invasive support for 3 d to ascertain longer-term outcome (Dahl, Bowen et al. 2018). Terminally, the PT lambs were euthanized after 10 days and their heart/lungs and brain were removed. Ex vivo BAL of the right cranial lobe (it has its own bronchus, pulmonary artery and vein) was done for similar analyses. Tracheal aspirates were collected according to the protocol for cytokines, BAL protein, ICAM-1 and VEGF. The spleen was collected to analyze immune cell population, using FACS.

Respiratory gas exchange and cardiovascular physiology.

Forced oscillation technique (FOT) allows non-invasive measurement of respiratory system (rs) impedance (Zrs) in uncooperative subjects by applying a pressure stimulus at the airway opening and measuring the resulting flow. The inventors have shown that FOT provides reliable noninvasive measurement of respiratory system mechanics in spontaneously breathing, normal term lambs from birth through the first 5 months of life (Dahl, Bowen et al. 2018). The methods and normal reference values defined in this study provide normal physiological context for determining the pathophysiological consequences of preterm birth.

The inventors measured cardiovascular function by indwelling arterial catheter to measure mean blood pressure and systolic/diastolic pressures coincident with oxygenation, ventilation, and renal function.

Bronchoalveolar lavage fluid (BALF) Analysis. Pups were sacrificed on PN14, and the trachea was cannulated with a small-caliber needle by instilling PBS endotracheally at 25 cm 1-120 pressure for 15 minutes. Two volumes of 300 μL of cold 1×PBS were instilled, gently aspirated, and pooled. Samples were centrifuged at 1000×g for 10 minutes at 4° C. The supernatant was collected, and total protein was quantified using the Pierce™ BCA Protein Assay Kit (Fisher Scientific Co, Houston, TX). The total cell count was done using the TC20 cell counter (BioRad, Hercules, CA). Similar method was followed for analyzing the protein concentration in BAL fluid collected from preterm lambs.

Histology, immunohistochemistry and immunofluorescence. Both the RA control and BPD mice were anesthetized (using an overdose of a cocktail of xylazine-ketamine) and lung and heart tissues were harvested after perfusion and fixed overnight in 4% paraformaldehyde. Fixed tissues were then washed in fresh PBS, dehydrated using 70% ethanol, cleared, and embedded in paraffin to be sectioned and stained with hematoxylin and eosin (H&E) for lung morphometry or immunohistochemistry/immunofluorescence as previously described (Leary, Das et al. 2019, Das, Achaiya et al. 2020, Das, Curstedt et al. 2020). Immunofluorescence staining was done for Ki67 (Abcam, 1:10) and Von Wilebrand Factor (vWF-DAKO, 1:100) on lung paraffin sections following the protocol as described earlier (Leary, Das et al. 2019) while TUNEL staining was done following the manufacturer's instructions (Roche).

Morphometry and quantification. To study chord length, septal thickness and radial alveolar count in the lungs, RV, LV and IVS thickness, 5 μm-thick left-lobe lung and heart paraffin-embedded sections were stained with H&E. Multiple randomly chosen areas (at least 10 areas) from each section were photographed using 100× total magnification. Sections with large airways or blood vessels from the lung were excluded for lung morphometry while quantitative measurements of PH-induced RV hypertrophy ratios (RV/LV and RV/LV+IVS) were done using the methodology described previously (Sun, Choo-Wing et al. 2013). The lung morphometry parameters were measured as described (Bhandari, Choo-Wing et al. 2008, Leary, Das et al. 2019, Das, Acharya et al. 2020, Das, Curstedt et al. 2020) either using ImageJ (a free software of NIH) or CellSens software (version 7, Olympus).

For quantification of cell proliferation and cell death, the entire lung section was divided into 3 areas, and the total number of Ki67+ve and TUNEL+ve cells nuclei were counted manually which was normalized with the total number of nuclei to give a percentage of positive cells. For vWF quantification, total number of closed vessels were counted per high power field area in one lung section. A minimum of 3 areas were chosen, and 3-7 animals were used for staining and counting.

Western Blot Analysis. Western blot analyses for TLR4 (Cell Signaling Technology, Danvers, MA; 1:1000), Ang2 (1:500; Sigma, St. Louis, MO), TGFβ, NFkB, TNFα, IL-10, IL-1(3, IL-4, Vegf, eNos, Vegf-D, BmpRII, Vinculin (1:500; SantaCruz, Dallas, TX), were performed, as previously described (Leary, Das et al. 2019), by loading 30 μg of lung protein, followed by immunoblotting with the above antibodies and visualizing with Odyssey infrared imaging system (LI-COR Biosciences, Lincoln, NE). Densitometric quantification was done using ImageJ after normalizing with Vinculin, the loading control housekeeping protein.

Multiplex ELISA. Lung lysate and blood plasma from control and AVR-48 treated group were used for Multiplex ELISA performed on 4 separate inflammatory panels of Meso Scale Discovery multispot assay system (MSD, Rockville, MD) to detect 2 chemokines (MIP-2, MCP-1) and 8 cytokines: IL-21, IP-10, IFNγ, IL-1(3, TNFα, IL-17, IL-10 and IL-6 following the manufacturer's instructions. Briefly, samples were diluted 1:1 in a total volume of 25 μl with the dilution buffer provided with MSD kit and incubated with the above labelling antibodies for 2 h, RT followed by washing with PB ST. The absorbance was detected using the MSD-specific luminometer.

Imaging. All images were captured on an Olympus IX70 with DP73 camera attachment. At least 5-7 images (magnifications of X10 or X20 or X40, as and when appropriate) were acquired for quantification. CellSens software version 7 was used for capturing of images and further modified with Adobe Photoshop 13 (Adobe Inc., San Jose, CA) for acquiring the best images.

Statistical Analysis. All statistical analyses were performed using Graph Pad Prism version 7.0 (GraphPad Software, San Diego, CA). The data are expressed as the mean±SEM with n=5 to 7 mice in each group. Groups were compared with the two-tailed unpaired t-test and one- or two-way analysis of variance (ANOVA), as appropriate. $P<0.05$ was considered statistically significant. For the toxicology and PK study, a generalized Analysis of Variance/Covariance (ANOVA/ANCOVA) test was performed on the numerical data (3 or more animals/groups) on the study as follows: An automatic transformation was used to analyze the data for homogeneity of variance using Levene's test. Parametric and non-parametric trends were analyzed using the Williams and the Shirley-Williams tests, respectively. Homogeneous data was analyzed using the ANOVA/ANCOVA, and the significance of intergroup differences between the control and test item-treated groups was analyzed using Dunnett's test. Heterogeneous data was analyzed using Kruskal-Wallis test and the significance of intergroup differences between the control and test item-treated groups was assessed using a nonparametric Dunnett's test. All data are reported as ±SEM. A significance level of $p<0.05$ at 95% confidence intervals was considered statistically significant for all the experiments reported in this study.

Figure 16:
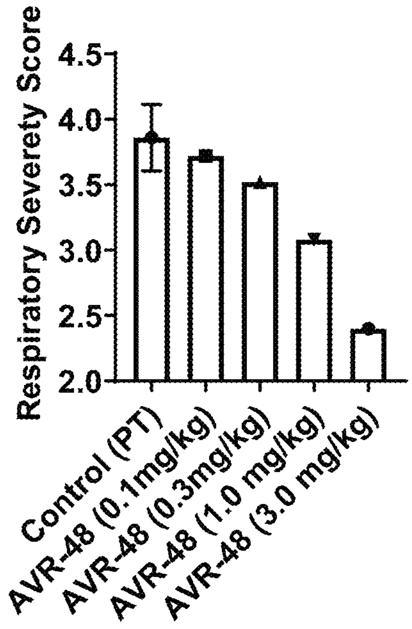
FIG. 16 shows the respiratory severity score pre-term lamb BPD model. Pre-term lambs delivered 128 days GA (n=2-4), dosed antenatally with steroid, and surfactant (Curosurf, 1 dose) immediately after delivery. The lambs were in invasive mechanical ventilator (IMV) for 7 days followed by 3 days in non-invasive ventilator. Either saline or AVR-48 (0.1, 0.3, 1.0 and 3.0 mg/kg) formulated in saline for IV dosing (2/d, 7 days) 6 h after delivery. Significant improvement in Respiratory Severity Score (RSS) after treatment with AVR-48 (1.0 and 3.0 mg/kg) over placebo treated control PT lambs (N=7, one from current study, 6 from previous studies). RSS is calculated using the formula: RSS=mean airway pressure (MAP)×fractional inspired oxygen ($FiO_2$). AVR-48 (3.0 mg·kg, n=4) showed the lowest RSS (2.4).

FIG. 16 shows the respiratory severity score pre-term lamb BPD model. Pre-term lambs delivered 128 days GA (n=2-4), dosed antenatally with steroid, and surfactant (Curosurf, 1 dose) immediately after delivery. The lambs were in invasive mechanical ventilator (IMV) for 7 days followed by 3 days in non-invasive ventilator. Either saline or AVR-48 (0.1, 0.3, 1.0 and 3.0 mg/kg) formulated in saline for IV dosing (2/d, 7 days) 6 h after delivery. Significant improvement in Respiratory Severity Score (RSS) after treatment with AVR-48 (1.0 and 3.0 mg/kg) over placebo treated control PT lambs (N=7, one from current study, 6 from previous studies). RSS is calculated using the formula: RSS=mean airway pressure (MAP)×fractional inspired oxygen ($FiO_2$). AVR-48 (3.0 mg·kg, n=4) showed the lowest RSS (2.4).

Figure 17A:
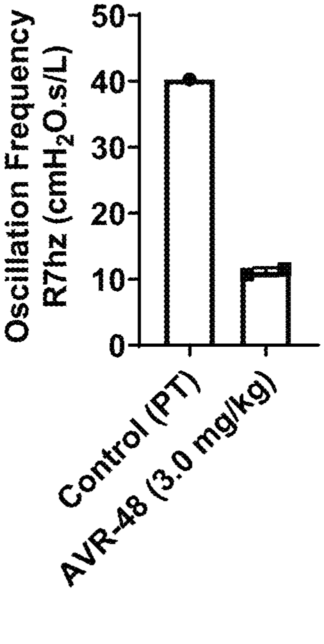
FIGS. 17A to 17C shows the respiratory system mechanics in pre-term lamb BPD model. Resistance (Rx) and reactance (Xr for the preterm lambs on day of life 10 (last day of life; hour of life 240 hr) are measured by the forced oscillation technique (FOT), which allows measurement of respiratory system mechanics in uncooperative subjects by applying a pressure stimulus at the airway opening and measuring the resulting flow. AVR-48 at 3.0 mg/Kg (N=4) led to lower resistance (R7 hz $cmH_2O$*s/L; respiratory system) relative to placebo. AVR-48 at 3 mg/Kg also led to less small airway resistance (R7-20 hz-$cmH_2O$*s/L) and less reactance (X7 hz-$cmH_2O$*s/L).
Figure 17B:
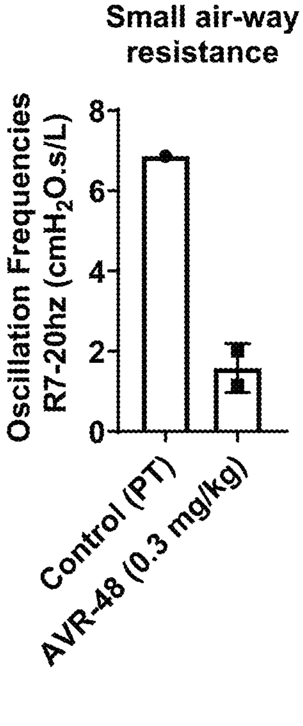
Figure 17C:
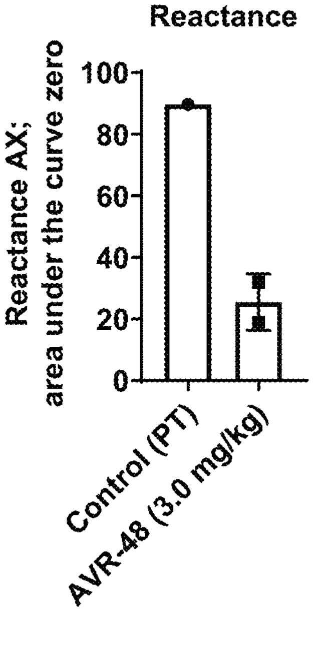

FIGS. 17A to 17C shows the respiratory system mechanics in pre-term lamb BPD model. Resistance (Rx) and reactance (Xr for the preterm lambs on day of life 10 (last day of life; hour of life 240 hr) are measured by the forced oscillation technique (FOT), which allows measurement of respiratory system mechanics in uncooperative subjects by applying a pressure stimulus at the airway opening and measuring the resulting flow. AVR-48 at 3.0 mg/Kg (N=4) led to lower resistance ($R_7$ hz $cmH_2O$*s/L; respiratory system) relative to placebo. AVR-48 at 3 mg/Kg also led to less small airway resistance ($R_7$-20 hz-$cmH_2O$*s/L) and less reactance (X7 hz-$cmH_2O$*s/L).

Figure 18A:
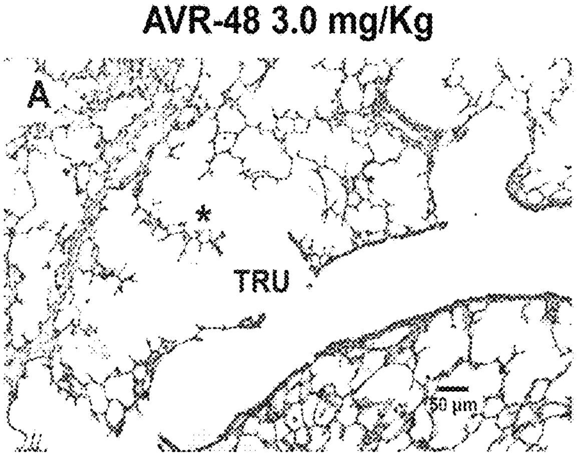
FIGS. 18A to 18E shows the histopathology of lung in pre-term lamb BPD model. The micrographs show terminal respiratory units (TRU) of the lung at the same magnification. Mechanical ventilation (MV) for 7 d leads to alveolar simplification (distended airspaces, few secondary septa, and thick mesenchyme) in vehicle treated PT lamb (FIG. 18D) which was significantly improved in AVR-48 lamb lung (FIG. 18C). Radial alveolar count is the number of tissue intersections across a terminal respiratory unit, from the center of the respiratory bronchiole to the perimeter of the terminal respiratory unit. Sheep, like humans, have terminal respiratory units (the human lung has about 150,000 terminal respiratory units, which are the physiologists' "alveolus" because these units are across which oxygen and carbon dioxide diffusion are measured (arterial blood gases). Preliminary results suggest that AVR-48 at 3.0 mg/Kg promotes alveoli formation (FIG. 18E).
Figure 18B:
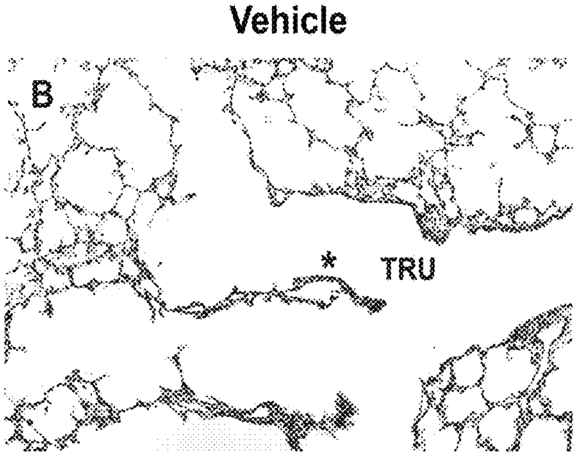
Figure 18C:
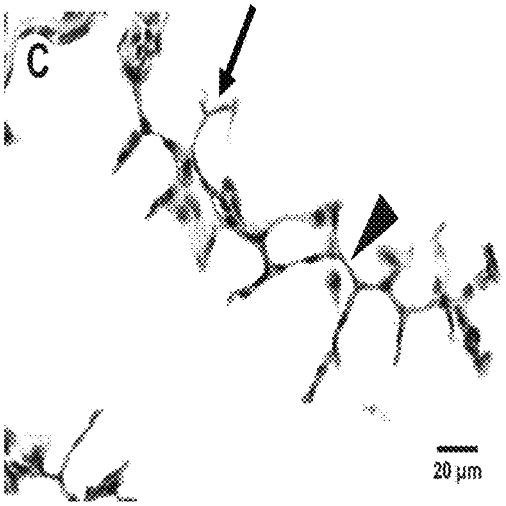
Figure 18D:
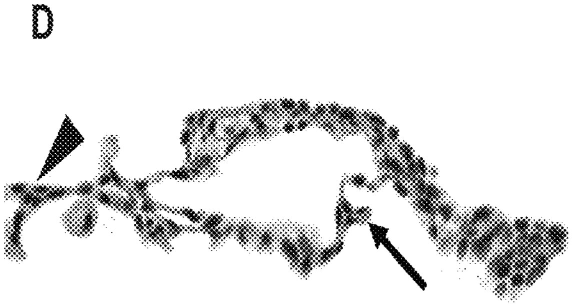
Figure 18E:
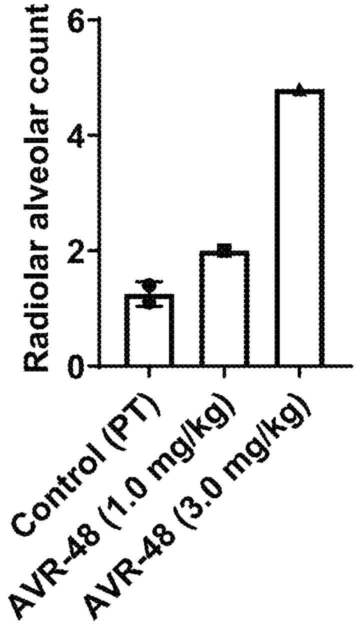

FIGS. 18A to 18E shows the histopathology of lung in pre-term lamb BPD model. The micrographs show terminal respiratory units (TRU) of the lung at the same magnification. Mechanical ventilation (MV) for 7 d leads to alveolar simplification (distended airspaces, few secondary septa, and thick mesenchyme) in vehicle treated PT lamb (FIG. 18D) which was significantly improved in AVR-48 lamb lung (FIG. 18C). Radial alveolar count is the number of tissue intersections across a terminal respiratory unit, from the center of the respiratory bronchiole to the perimeter of the terminal respiratory unit. Sheep, like humans, have terminal respiratory units (the human lung has about 150,000 terminal respiratory units, which are the physiologists' "alveolus" because these units are across which oxygen and carbon dioxide diffusion are measured (arterial blood gases). Preliminary results suggest that AVR-48 at 3.0 mg/Kg promotes alveoli formation (FIG. 18E). N=3.

Figure 19:
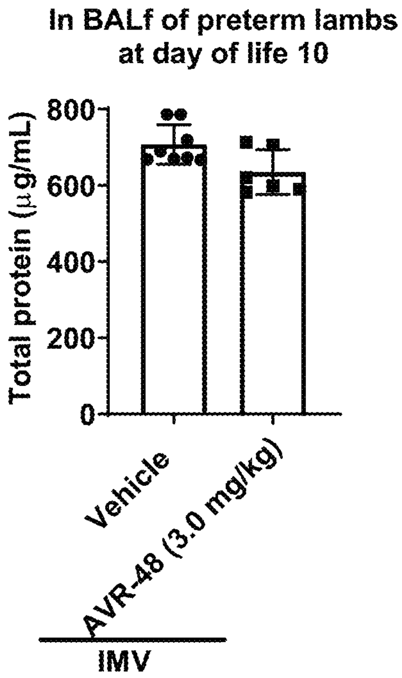
FIG. 19 shows the treatment with AVR-48 decreased the total protein concentration in BAL fluid as compared to vehicle treated lambs after 10 days. All preterm lambs were under invasive mechanical ventilation (intubated) for 7 days followed by 3 days of $O_2$ mask.

FIG. 19 shows the treatment with AVR-48 decreased the total protein concentration in BAL fluid as compared to vehicle treated lambs after 10 days. All preterm lambs were under invasive mechanical ventilation (intubated) for 7 days followed by 3 days of $O_2$ mask.

Figure 20:
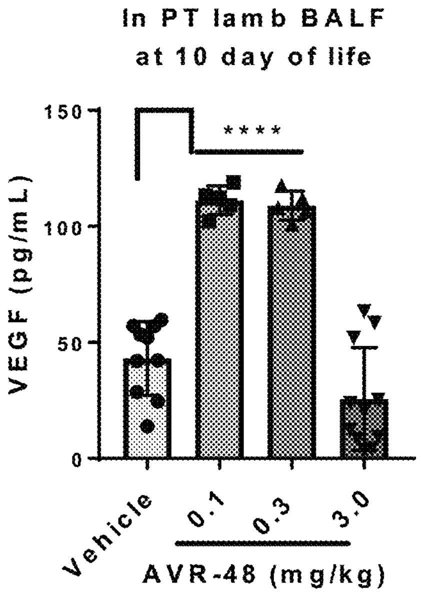
FIG. 20 shows the treatment with AVR-48 increase VEGF concentrations in BAL fluid at low doses where high dose (3.0 mg/kg) had no effect as compared to vehicle treated lambs after 10 days. All preterm lambs were under invasive mechanical ventilation (intubated) for 7 days followed by 3 days of $O_2$ mask.

FIG. 20 shows the treatment with AVR-48 increase VEGF concentrations in BAL fluid at low doses where high dose (3.0 mg/kg) had no effect as compared to vehicle treated lambs after 10 days. All preterm lambs were under invasive mechanical ventilation (intubated) for 7 days followed by 3 days of $O_2$ mask.

Figure 21:
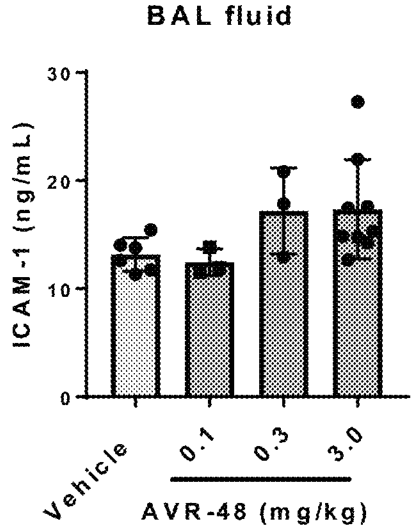
FIG. 21 shows the treatment with AVR-48 increase ICAM-1 concentrations in BAL fluid as compared to vehicle treated lambs after 10 days. All preterm lambs were under invasive mechanical ventilation (intubated) for 7 days followed by 3 days of $O_2$ mask. Decrease in total protein shows less pulmonary leakage and edema where increase in VEGF and ICAM-1 in BAL fluid correlated to the increased alveolation of the lung in AVR-48 treated lambs as observed from lung histopathology and radial alveolar count (FIG. 18E).

FIG. 21 shows the treatment with AVR-48 increase ICAM-1 concentrations in BAL fluid as compared to vehicle treated lambs after 10 days. All preterm lambs were under invasive mechanical ventilation (intubated) for 7 days followed by 3 days of $O_2$ mask. Decrease in total protein shows less pulmonary leakage and edema where increase in VEGF and ICAM-1 in BAL fluid correlated to the increased alveolation of the lung in AVR-48 treated lambs as observed from lung histopathology and radial alveolar count (FIG. 18E).

Figure 22:
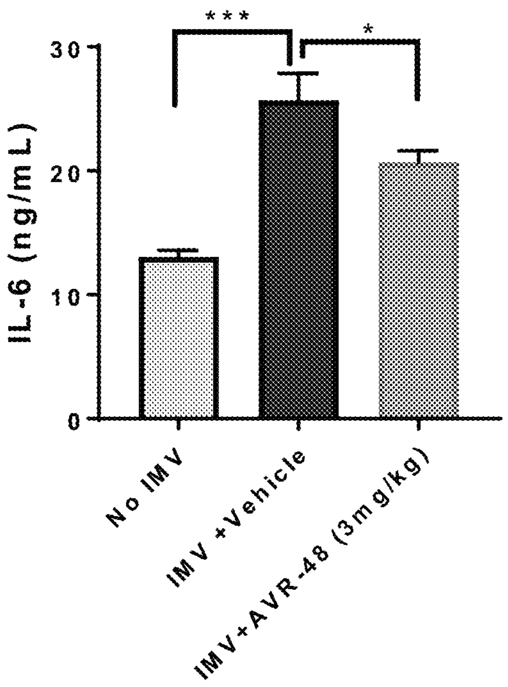
FIG. 22 shows the treatment with AVR-48 significantly decreased IL-6 concentration in plasma as compared to vehicle treated lambs after 10 days. All preterm lambs were under invasive mechanical ventilation (intubated) for 7 days followed by 3 days of $O_2$ mask. n=3-4. *p<0.05, ***p<0.001. One way ANOVA.

FIG. 22 shows the treatment with AVR-48 significantly decreased IL-6 concentration in plasma as compared to vehicle treated lambs after 10 days. All preterm lambs were under invasive mechanical ventilation (intubated) for 7 days followed by 3 days of $O_2$ mask. n=3-4. *$p<0.05$, ***$p<0.001$. One way ANOVA.

Figure 23:
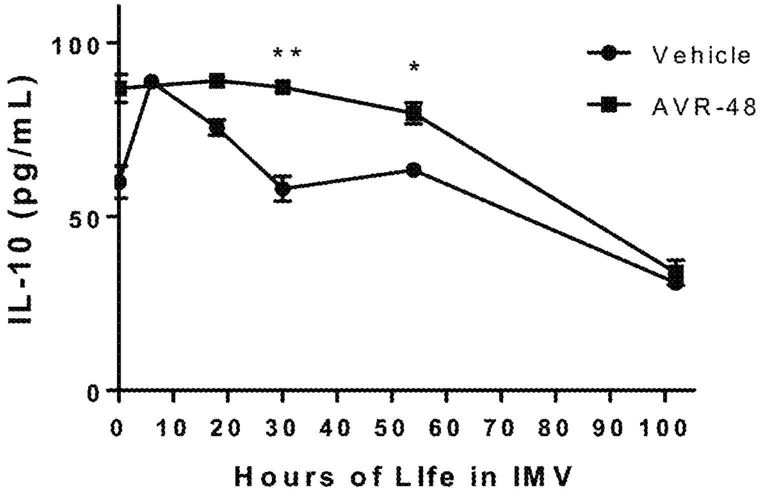
FIG. 23 shows the effect of AVR-48 treatment on IL-10 in lamb plasma. While IL-10 decreased in a time dependent manner in vehicle treated lamb plasma, treatment with AVR-48 (2/d for 7 days, first dose started at 6+h) significantly decreased IL-10 concentration in plasma at early time points (1-4 days) needed to inhibit the hyperinflammation as compared to vehicle treated lambs at different time points. All preterm lambs were under invasive mechanical ventilation (intubated) for 7 days followed by 3 days of $O_2$ mask. n=3-4. *p<0.05, **p<0.01. Two-way ANOVA.

FIG. 23 shows the effect of AVR-48 treatment on IL-10 in lamb plasma. While IL-10 decreased in a time-dependent manner in vehicle-treated lamb plasma, treatment with AVR-48 (2/d for 7 days, first dose started at 6+h) significantly decreased IL-10 concentration in plasma at early time points (1-4 days) needed to inhibit the hyperinflammation as compared to vehicle-treated lambs at different time points. All preterm lambs were under invasive mechanical ventilation (intubated) for 7 days followed by 3 days of $O_2$ mask. n=3-4. *$p<0.05$, **$p<0.01$. Two-way ANOVA.

Example 4: Synthesis of Biotinylated AVR-48 (Scheme-1)

Experimental Procedure: Biotin analog of AVR-48: To a stirred solution of AVR-48 (2.0 g, 5.84 mmol) in anhydrous $CH_2Cl_2$ triethylamine (1.5 equivalent) was added followed by drop-wise addition of MSCl (1.0 equivalent) and stirred for overnight, reaction completion noted by TLC that provided intermediate 2, in 89% of yield after column purification. This product was directly used in the next step without any further spectral analysis. To the 0-Mesyl derivative 2 (1 equivalent) in anhydrous DMF was added NaN3 (3 equivalent) and heated at 65° C. for 6 h to give intermediate 3 in 82% as a pure enough product determined by TLC to proceed next without any purification. The azide intermediate 3 was converted to intermediate amine 4 by using standard azide to amine reduction procedure using TPP, $H_2O$ by stirring at 23° C. overnight. This intermediate product 4, was then coupled with commercially available NH-succinamide-Biotin using 1.5 equivalents of EDCI, DIPEA and catalytic amount of HOBt to give 91% yield of Biotin analog of AVR-48 (BT-AVR-48) after column purification. The structure of BT-AVR-48 was confirmed by both $^1$HNMR and MS.

$^1$H NMR ($DMSOd_6$) of BT-AVR-48: δ 1.25 (m, 2H), 1.55-1.58 (m, 4H), 1.88 (s, 3H), 2.13 (t, 2H), 2.42-2.59 (dd, 2H), 2.73-2.84 (dd, 1H), 3.12-3.18 (m, 2H), 3.20-3.25 (m, 1H), 3.72-3.78 (m, 1H), 4.14 (m, 1H), 4.28 (m, 1H), 5.15 (d, 1H), 6.38-6.43 (d, 1H), 7.13-7.16 (d, 2H), 7.91-7.99 (m, 2H), 8.16-8.19 (d, 2H). LC-TOF (+ESI): 568 (M+).

Figure 24A:
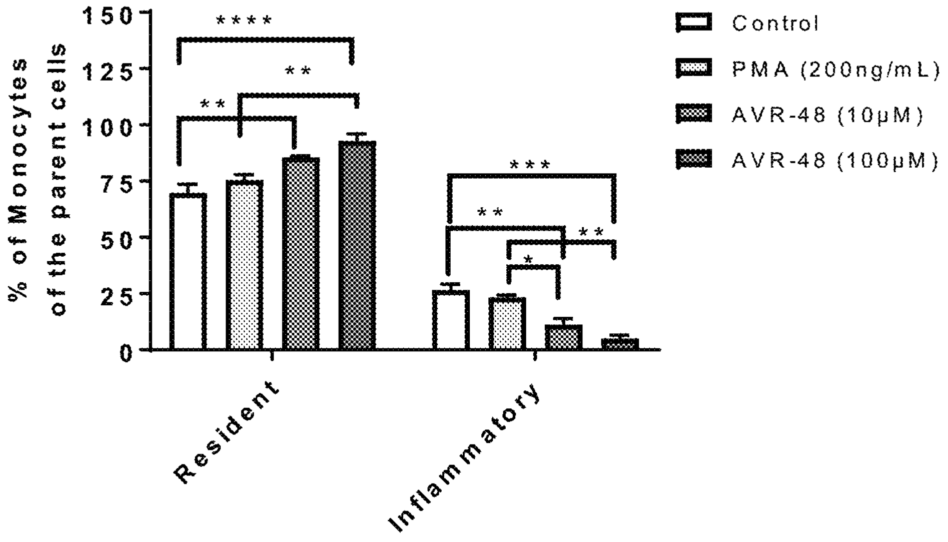
FIGS. 24A to 24C shows that treatment with AVR-48 (compound 8) for 48-72 h produces more resident/anti-inflammatory macrophages (Lytic hi/low) (FIGS. 24A, 24B). Biotin conjugated AVR-48 (BT-AVR-48) binds to mouse splenic monocytes (LY6c+, CD19−, CD3−) dose dependently (FIG. 24C) as determined by FACS analysis.

Example 5: AVR-48 Binds to Monocytes in Mouse Spleen Derived Monocytes and Polarizes them to Non-Inflammatory M2/Resident Macrophages in a Dose Dependent Manner Primary splenocytes of C57BL/6J mice (n=3-5) were treated of AVR 48 for 72 hrs. PMA (200 ng/mL) was used as a positive control. The cells were washed and stained for CD11b and MHC-II and were analyzed by FACS. Dead cells were excluded by Live/dead staining during analysis. It was observed that the expression levels of MHC-II and CD11b increased upon AVR48 stimulation in a dose dependent manner in splenocytes. Monocytes were further analyzed for Ly6c. As described by (Swirski et al, J Clin Invest, 2007, 117(1):195-205. doi: 10.1172/JCI29950), spleen cells with LY6c Hi are considered as inflammatory whereas Ly6c low as resident and anti-inflammatory (FIG. 24A). Next, live singlet cells that were CD11b hi and CD11c low, were gated for F4/80 and MHC-II expression. Cells having increased expression of F4/80 and MHC-II were considered as macrophages whereas cells having low expression of F4/80 were considered as monocytes.

Binding of biotinylated conjugated AVR-48 to splenic monocytes/macrophages.

Figure 24B:
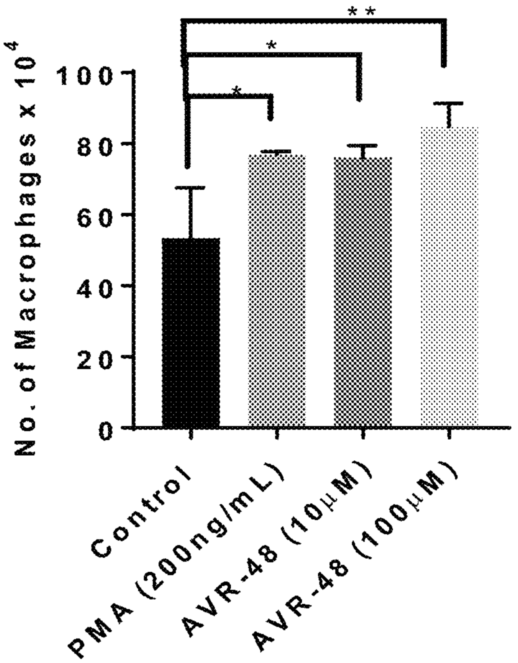
Figure 24C:
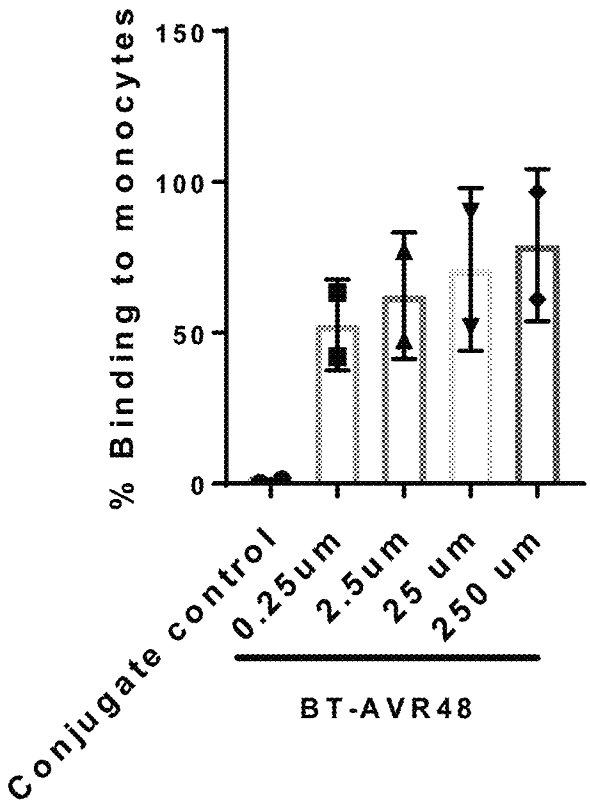

FIGS. 24A to 24C shows that treatment with AVR-48 (compound 8) for 48-72 h produces more resident/anti-inflammatory macrophages (Ly6c hi/low) (FIG. 24A, 24B). Biotin conjugated AVR-48 (BT-AVR-48) binds to mouse splenic monocytes (LY6c+, CD19−, CD3−) dose dependently (FIG. 24C) as determined by FACS analysis.

Briefly, cells were incubated at 4° C. for 1 hr followed by incubation with biotinylated AVR48 (0.25 μM, 2.5 μM, 25 μM, and 250 μM) along with monocyte (Ly6C) markers. Then the cells were probed with appropriate fluorescence coupled streptavidin and analyzed by FACS. Dead cells were excluded during analysis (FIG. 24C). N=2-3

Binding of biotinylated conjugated AVR-48 to TLR4 and CD163 receptor proteins in splenic monocytes/macrophages.

Figure 25A:
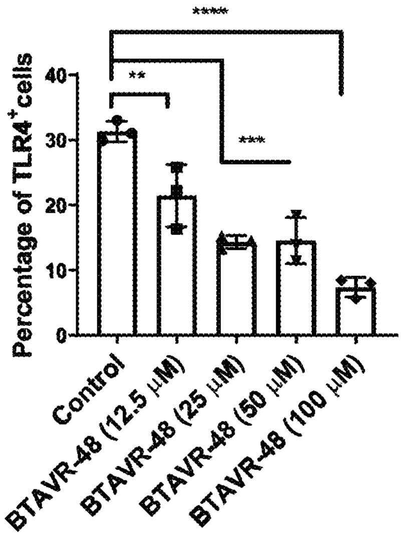
FIGS. 25A and 25B show that treatment with Biotin conjugated AVR-48 (BT-AVR-48) binds to both toll like receptor 4 (TLR4) and CD163 scavenger receptor proteins in mouse spleen derived monocytes (LY6c+, CD19−, CD3−) dose dependently as determined by FACS analysis.
Figure 25B:
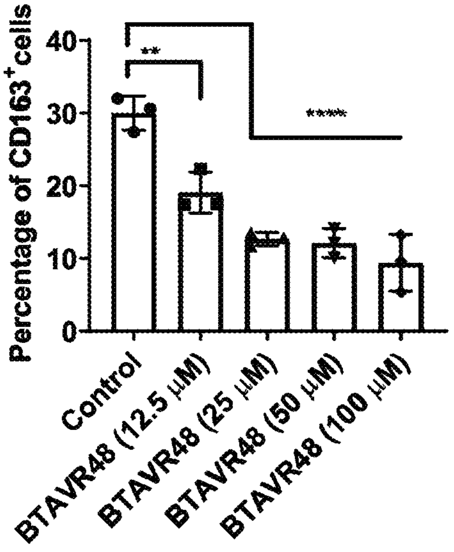

FIGS. 25A and 25B show that treatment with Biotin conjugated AVR-48 (BT-AVR-48) binds to both toll like receptor 4 (TLR4) and CD163 scavenger receptor proteins in mouse spleen derived monocytes (LY6c+, CD19−, CD3−) dose dependently as determined by FACS analysis.

Briefly, cells were incubated at 4° C. for 1 hr followed by incubation with biotinylated AVR48 (12.5 μM, 25 μM, 50 μM, and 100 μM) along with PE anti-mouse CD284 (TLR4) antibody (Biolegend) and Brilliant Violet 421™ anti-mouse CD163 antibody (Biolegend). Then the cells were probed with appropriate fluorescence coupled streptavidin and analyzed by FACS. Dead cells were excluded during analysis (FIGS. 25A and 25B). N=3

Example 6. AVR-48 Demonstrates Anti-Inflammatory and Immunomodulatory Activities in Human Blood Cells and in Whole Cord Blood Bronchopulmonary dysplasia (BPD) is a common chronic respiratory disease in premature infants. Inflammation is the cornerstone of lung injury in pre-term babies leading to BPD. AVR-48, a small molecule immunomodulator (1-4) for the prevention of BPD in at-risk preterm infants. AVR-48 was efficacious in preventing BPD phenotypes in a hyperoxia-induced mouse model and in a pre-term lamb model. The objective was to demonstrate the immunomodulatory and anti-inflammatory effect of AVR-48 using human lung epithelial cells, cord-blood mononuclear cells and whole cord blood.

Figure 26A:
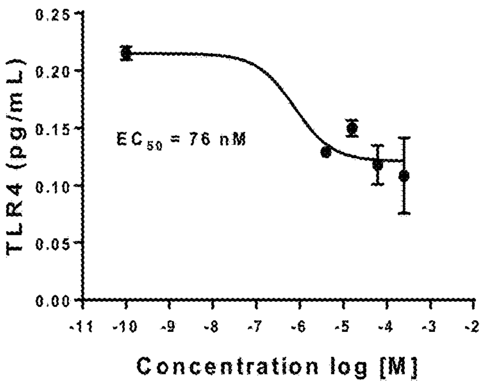
FIGS. 26A to 26C show that AVR-48 binds to TLR4 in THP-1 human monocyte cells (FIG. 26A) and increases IL-10 production (FIG. 26B). AVR-48 decreases LPS induced TNF-α production when pretreated for 24 h (FIG. 26C) as determined by ELISA.
Figure 26B:
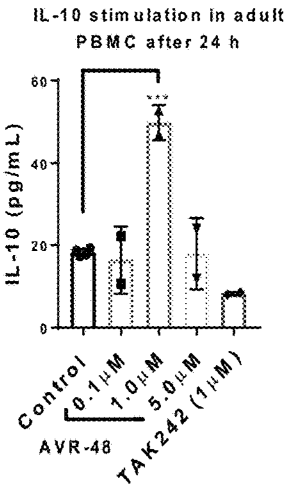
Figure 26C:
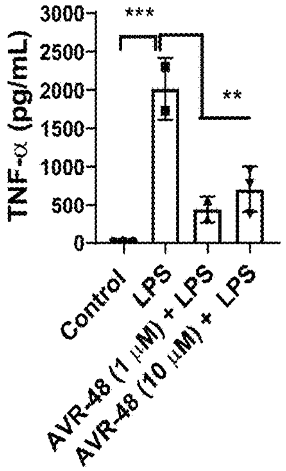

FIGS. 26A to 26C show that AVR-48 binds to TLR4 in THP-1 human monocyte cells (FIG. 26A) and increases IL-10 production (FIG. 26B). AVR-48 decreases LPS induced TNF-α production when pretreated for 24 h (FIG. 26C) as determined by ELISA.

FIG. 26A, TLR4 assay: $1\times10^5$ THP cells (ATCC) were seeded in 24 well plates and stimulated with phorbol myristyl actetate (PMA, 200 ng/mL) for 48 h. Cell lysates were prepared, total protein was quantified and treated with different concentrations (4, 16, 62.5 and 250 μM) of the AVR-48 for 2 h. ELISA was performed after to assess unbound TLR4 following manufacturer's instruction (Raybiotech). TLR4 $IC_{50}$ of the AVR-48 was calculated using GraphPad Prism7.04.

FIG. 26, shows that AVR-48 dose dependently increased secreted IL-10 levels in the supernatant of human peripheral blood monocytes (hPBMC) after 24h of post treatment. FIG. 26 C, Pretreatment (24 h) of AVR-48 to hPBMC followed by 6h of treatment with LPS (25 ng/ml) decreased the secreted TNF-α production in hPBMC cell supernatants. N=3.p<0.01, *p<0.001. One-way ANOVA.

Figure 27:
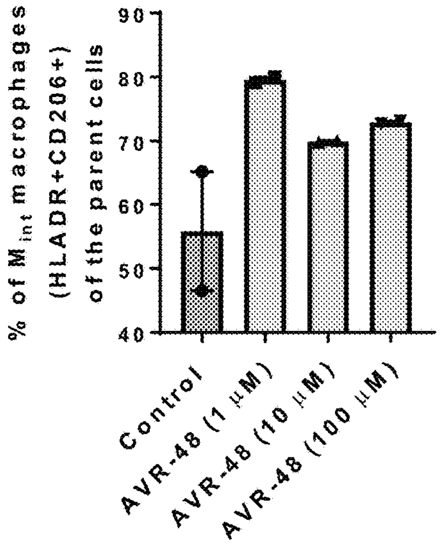
FIG. 27: Change in macrophage populations after AVR-48 treatment. Briefly, hPBMC were plated in a 96 well plate and treated with AVR 48 for 72 hrs. The cells were washed and stained for CD32, CD14, CD16, HLADR, CD86, CD206 anti-human antibodies and were analyzed by FACS. Dead cells were excluded by live/dead staining (7AAD) during analysis. The % of intermediate macrophages of the parent cells are determined as the macrophages stained positive for both HLADR and CD206 surface markers. The bar graph representing percentage of intermediate macrophages (Mint) of the parent macrophage populations (CD14+CD16+) after treatment with AVR-48. n=2 technical replicates and the experiment is repeated 3 times. AVR-48 binds to both toll-like receptor 4 (TLR4) and CD163 receptor on monocytes. In hPBMC, AVR-48 treatment for 72 h increased the percentage of intermediate macrophages and decreased M1 macrophages.

FIG. 27 shows the change in macrophage populations after AVR-48 treatment. Briefly, hPBMC were plated in a 96 well plate and treated with AVR 48 for 72 hrs. The cells were washed and stained for CD32, CD14, CD16, HLADR, CD86, CD206 anti-human antibodies and were analyzed by FACS. Dead cells were excluded by live/dead staining (7AAD) during analysis. The % of intermediate macrophages of the parent cells are determined as the macrophages stained positive for both HLADR and CD206 surface markers. The bar graph representing percentage of intermediate macrophages (Mint) of the parent macrophage populations (CD14+CD16+) after treatment with AVR-48. n=2 technical replicates and the experiment is repeated 3 times. AVR-48 binds to both toll-like receptor 4 (TLR4) and CD163 receptor on monocytes. In hPBMC, AVR-48 treatment for 72 h increased the percentage of intermediate macrophages and decreased M1 macrophages.

Figure 28A:
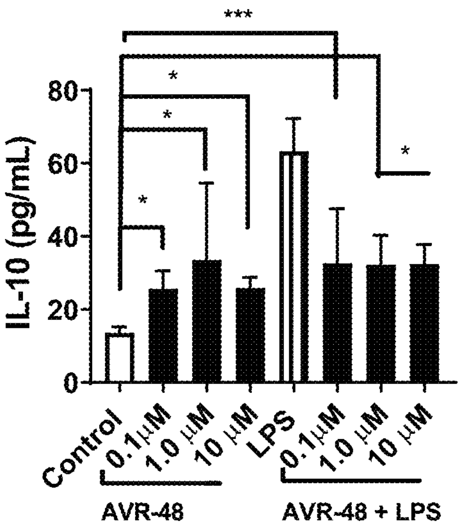
FIGS. 28A to 28B show that human cord blood monocytes (CBMC) treated with AVR-48 alone showed increased IL-10 (~2.5-fold) at 0.1-10 μM. LPS treatment significantly increased the IL-10 (~5-fold), IL-1β (~30 fold) (FIG. 28A & FIG. 28B). LPS+AVR-48 decreased both IL-10 and IL-1β significantly at 10 μM.
Figure 28B:
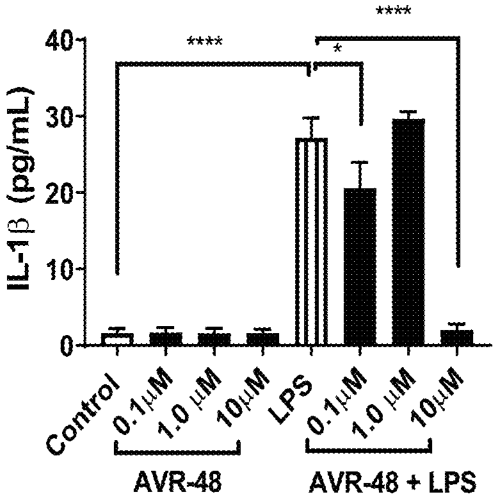

FIGS. 28A to 28B show that human cord blood monocytes (CBMC) treated with AVR-48 alone showed increased IL-10 (~2.5-fold) at 0.1-10 μM. LPS treatment significantly increased the IL-10 (~5-fold), IL-10 (~30 fold) (FIG. 28A & FIG. 28B). LPS+AVR-48 decreased both IL-10 and IL-1β significantly at 10 μM.

Figure 29:
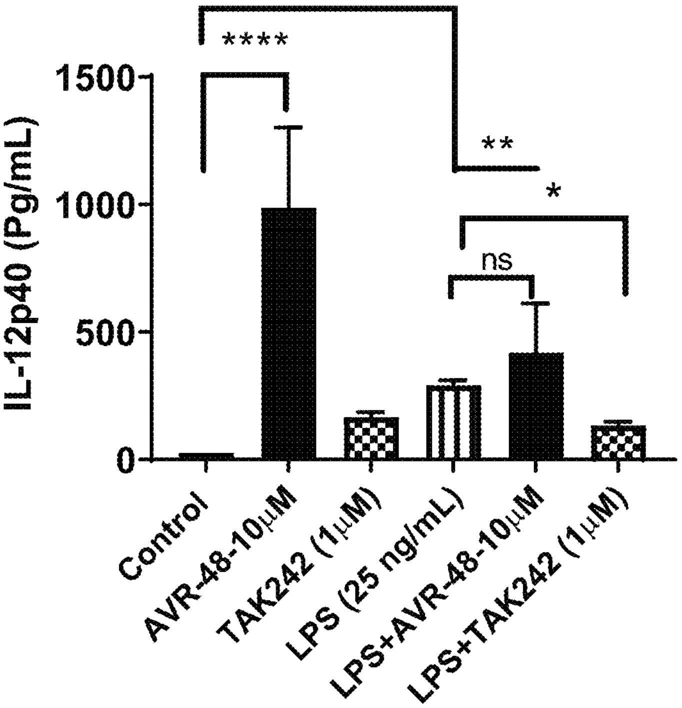
FIG. 29 shows immunostimulatory activity of AVR-48 in CBMC and increase in IL-12p40 cytokine. IL-12p40, is a marker for the innate immune response to infection and is down regulated in CBMC. Either AVR-48 (10 μM) alone or LPS+AVR-48 treatment produced a higher IL-12p40 response than only LPS indicating facilitation of an active immune system. However, a commercially available TLR4 antagonist TAK242 when tested showed to decrease the LPS induced increase in IL-12p40 level that clearly demonstrated AVR-48 are not TLR4 antagonists but TLR4 modulators and AVR-48 treatment is not immunosuppressive like a canonical TLR4 antagonist.

FIG. 29 shows immunostimulatory activity of AVR-48 in CBMC and increase in IL-12p40 cytokine. IL-12p40, is a marker for the innate immune response to infection and is down regulated in CBMC. Either AVR-48 (10 μM) alone or LPS+AVR-48 treatment produced a higher IL-12p40 response than only LPS indicating facilitation of an active immune system. However, a commercially available TLR4 antagonist TAK242 when tested showed to decrease the LPS induced increase in IL-12p40 level that clearly demonstrated AVR-48 are not TLR4 antagonists but TLR4 modulators and AVR-48 treatment is not immunosuppressive like a canonical TLR4 antagonist.

Figure 30A:
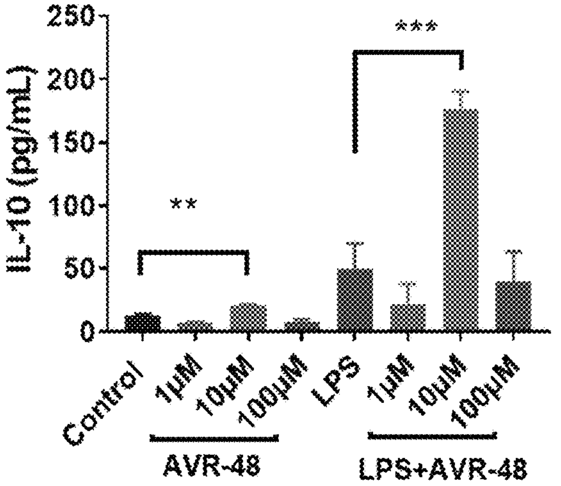
FIGS. 30A and 30B show that whole cord blood (WCB) treated with AVR-48 alone showed increased IL-10 (~1.5-fold) at 10 μM. LPS treatment moderately increased the IL-10 (~2.5-fold). LPS+AVR-48 increased IL-10 significantly at 10 μM (FIG. 30A). TNF-α was already upregulated in WCB where treatment with AVR-48 significantly decreased the TNF-α level alone or in combination with LPS (FIG. 30B). IL-1β and IFN-Y were not detected with either AVR-48 alone or in combination with LPS. N=3, *p<0.5, p<0.05, *p<0.005, ****p<0.001, One-way ANOVA.
Figure 30B:
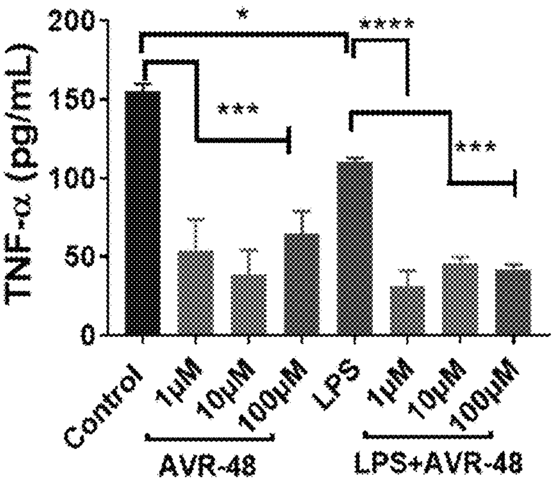

FIGS. 30A and 30B show that whole cord blood (WCB) treated with AVR-48 alone showed increased IL-10 (~1.5-fold) at 10 μM. LPS treatment moderately increased the IL-10 (~2.5-fold). LPS+AVR-48 increased IL-10 significantly at 10 μM (FIG. 30A). TNF-α was already upregulated in WCB where treatment with AVR-48 significantly decreased the TNF-α level alone or in combination with LPS (FIG. 30B). IL-1β and IFN-Y were not detected with either AVR-48 alone or in combination with LPS. N=3, *p<0.5, p<0.05, *p<0.005, ****p<0.001, One-way ANOVA.

Figure 31A:
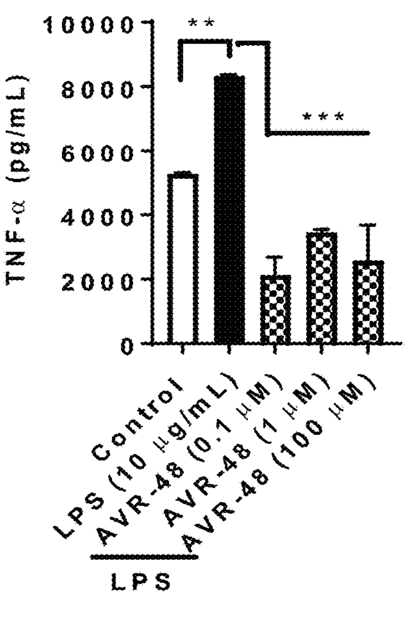
FIGS. 31A and 31B show that AVR-48 decreased both TNF-α and nitric oxide (NO) production in human lung alveolar type I epithelial cells (AT1) when co-treated with LPS as determined by ELISA. No significant level of IL-10 or IL-β were detected in the epithelial cells like observed in monocyte/macrophage cells.
Figure 31B:
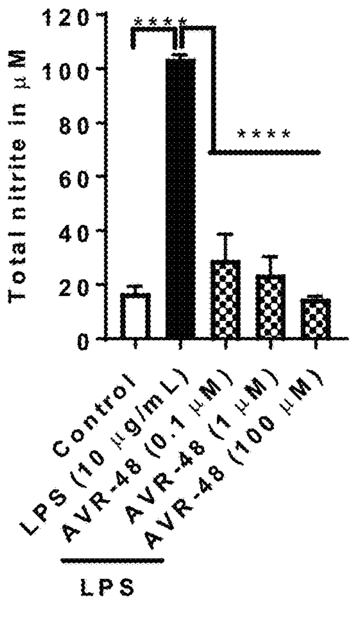

Example 7: AVR-48 Demonstrates Anti-Inflammatory Activities in Human Lung Epithelial Cell FIGS. 31A and 31B show that AVR-48 decreased both TNF-α and nitric oxide (NO) production in human lung alveolar type I epithelial cells (AT1) when co-treated with LPS as determined by ELISA. No significant level of IL-10 or IL-β were detected in the epithelial cells like observed in monocyte/macrophage cells.

It was found that binding of AVR-48 to the surface receptors of monocytes/macrophages in blood or in lungs is possibly via surface receptor TLR4 with a sub nanomolar EC50. AVR-48 is not a canonical TLR4 inhibitor/antagonist like TAK242 and is a receptor modulator. Pretreatment of AVR-48 selectively transforms monocytes to non-inflammatory/resident macrophages. IL-10 seems to be elevated after AVR-48 treatment to human peripheral and cord blood monocytes. TLR4 activation by LPS leads to inflammatory response and AVR-48 decreased, TNF-α levels significantly in human CBMC, whole cord blood as well as in lung epithelial cells. AVR-48 is a promising molecule with potential therapeutic benefits to prevent lung injury including the prevention of BPD.

Figure 32:
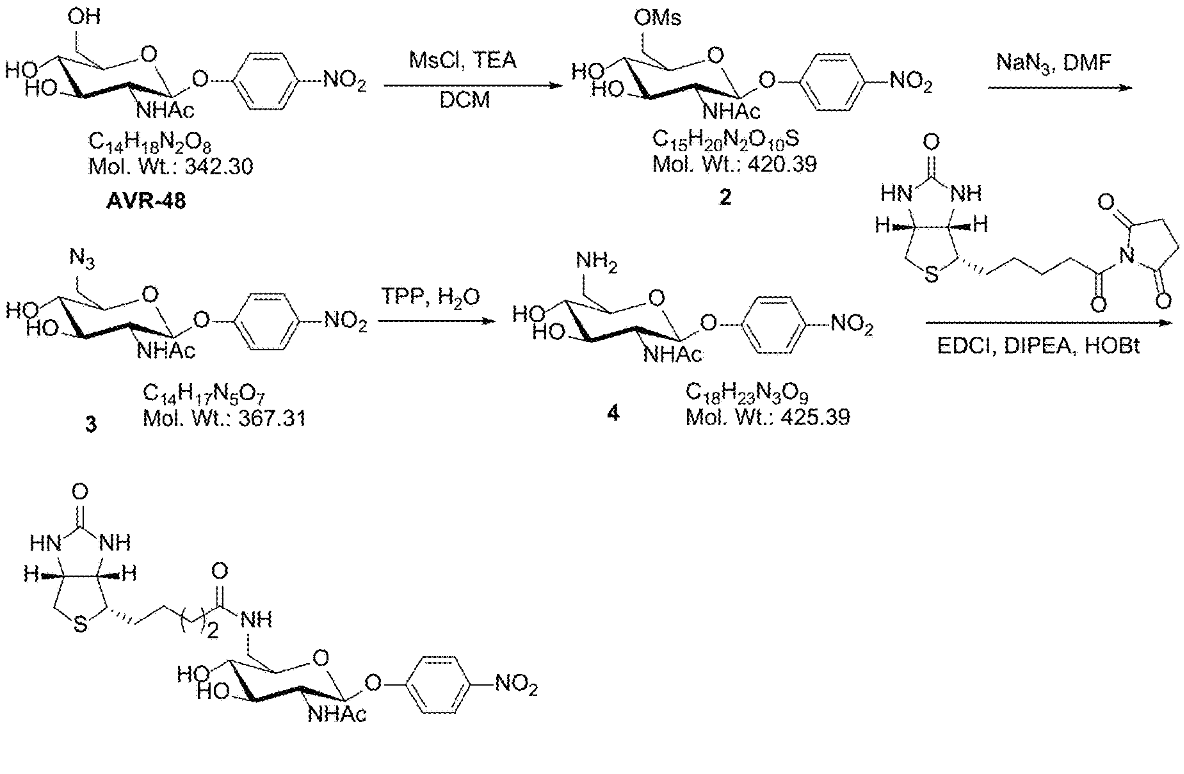
FIG. 32 synthesis of BT-AVR-48.
Figure 33:
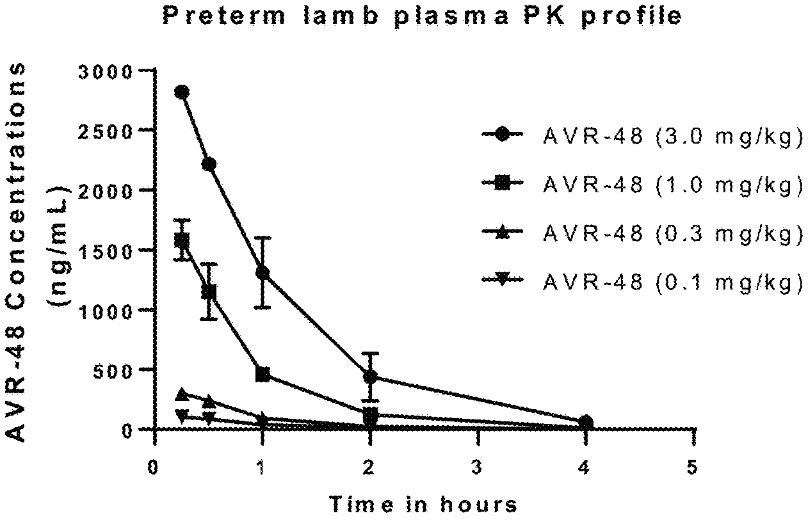
FIG. 33 shows the pK and formulation results via IV and oral dosing. Maximum drug concentration ($C_{max}$) of AVR-48 dosed as a saline solution at 3.0 mg/kg/dose (efficacy dose, n=3 preterm lambs) in plasma after single dose via intravenous administration showed linear decline in drug concentration, with half-life of 0.56+1.5 h and $C_{max}$=12.2±5.6 μM

FIG. 32 shows the synthesis of BT-AVR-48. FIG. 33 shows the pK and formulation results via IV and oral dosing. Maximum drug concentration ($C_{max}$) of AVR-48 dosed as a saline solution at 3.0 mg/kg/dose (efficacy dose, n=3 preterm lambs) in plasma after single dose via intravenous administration showed linear decline in drug concentration, with half-life of 0.56+1.5 h and $C_{max}$=12.2±5.6 μM.

Figure 34:
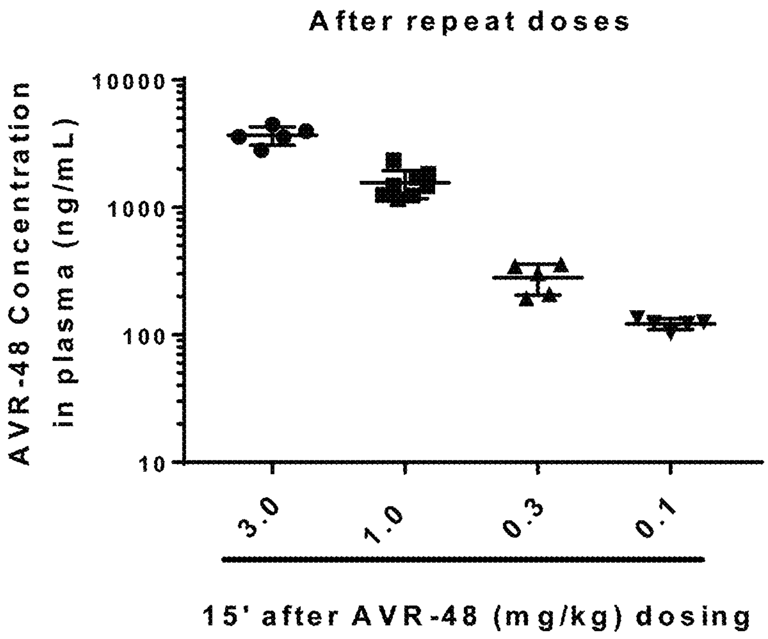
FIG. 34 shows that there is no drug accumulation after repeat IV dosing for 7 days to preterm lambs showing good clearance.

FIG. 34 shows that there is no drug accumulation after repeat IV dosing for 7 days to preterm lambs showing good clearance.

Method for formulation preparation and delivery to rats via oral route.

Formulation:

TABLE I

| Summary of ingredients used in the preparation of the nanosuspensions. | | | |
|---|---|---|---|
| Ingredient | Amount (%) | Amount (mg) | Amount (mg) |
| AVR-48 | 5 | 151.48 | — |
| AVR-84 | 5 | — | 150.38 |
| Hydroxypropyl cellulose SSL | 2.5 | 75.41 | 75.09 |
| Sodium dodecyl sulfate | 0.1 | 3.27 | 3.12 |
| Water | | Qs ad. 3000 | Qs ad. 3000 |

The test item, the stabilizer (HPC-SSL) and the surfactant (SDS) were accurately weighed and transferred in a 15-mL amber glass jar charged with 6 mL of yttrium-stabilized zirconia beads (0.8 mm). The suspension was brought to final weight with water in order to achieve the desired final concentration. The formulation was mixed using a vortex for at least 1 minute and then homogenized using a roller mill (Unitized Jar Mill, Model 755 RMV from U.S. Stoneware (purchased from Fisher Scientific Canada cat #08-381-1) at 50 rpm for 48 hours.

As the chemical stability of tested compounds has not been assessed, the content assay of AVR-48 and AVR-84 was evaluated at the end of nanomilling process by HPLC.

Particles size measurement was not possible as the suspensions resulted produced clear solutions when mixed with water, dilution required prior the particle size analysis.

For the animal study, the suspensions prepared at 50 mg/mL were diluted to 10 mg/mL using a blank vehicle prepared using the same proportions of excipients as those indicated in Table I. By diluting the concentrated suspension of AVR-84 a clear solution was obtained whereas for AVR-48 the solution was a homogeneous cloudy solution.

Animals and dosing: The male SD rats (N=3) were obtained from Charles River. Each animal was weighed before the administration of the test item. The animals were observed for potential clinical signs following the dosing. At the specified time points, t=15', 30', 1 h, 2 h, 3 h, 4 h, 6 h, 8 h and 24 h (N=3), blood (100 μL) was collected via the saphenous vein using MINIVETTE® POCT K3-EDTA. The blood samples were centrifuged for 10 min at 965 g and 4° C. within 30 min of collection, to obtain plasma. Plasma samples were kept frozen at −80° C. The plasma samples were thawed on ice and kept on ice during the sample preparation. Thirty μL of plasma samples were mixed with 75 μL of precipitation solution (80% acetonitrile and 20% methanol containing IS) was added. Samples were mixed and centrifuged at 3500 rpm for 10 min at 4° C. Forty μL of the supernatant was transferred to a 96 well plate, and 80 μL of water+0.1% formic acid was added and analyzed using the in house developed HPLC method.

Figure 35:
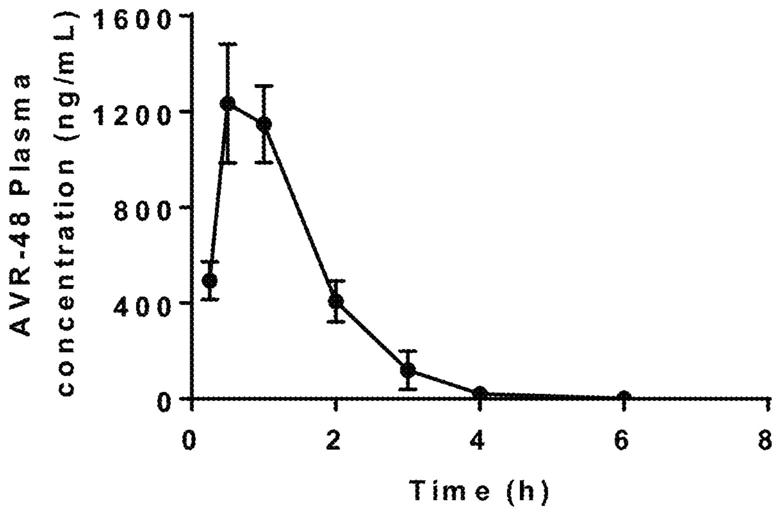
FIG. 35 shows an oral formulation of AVR-48 (Compound 8) was prepared and dosed to adult rats (n=3) at 100 mg/kg dose. The plasma showed linear decline in drug concentration consistent with previously reported IV profile, with $T_{max}$ of 0.7±0.3 h, half-life (T v2) of 0.6±0.4 h, and $C_{max}$ of 3.64±0.66 μM.

FIG. 35 shows an oral formulation of AVR-48 (Compound 8) was prepared and dosed to adult rats (n=3) at 100 mg/kg dose. The plasma showed linear decline in drug concentration consistent with previously reported IV profile, with $T_{max}$ of 0.7±0.3 h, half-life (T v2) of 0.6±0.4 h, and $C_{max}$ of 3.64±0.66 04.

Figure 36:
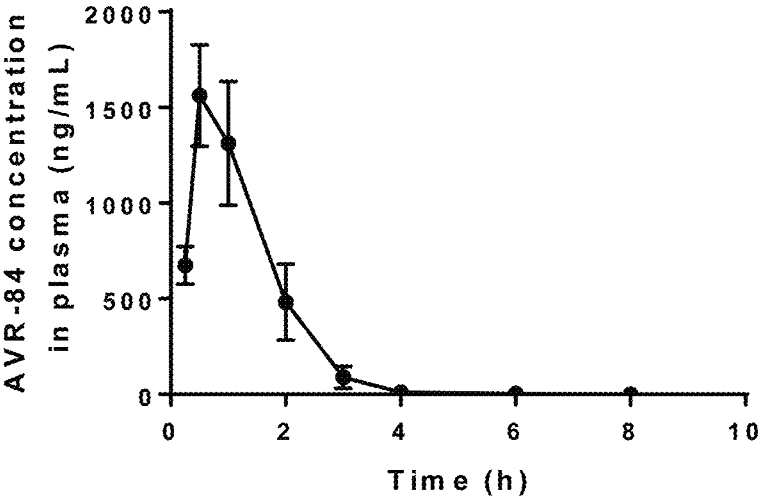
FIG. 36 shows an oral formulation of AVR-84 (compound 17) was prepared and dosed to adult rats (n=3) at 100 mg/kg dose. The plasma showed linear decline in drug concentration, with $T_{max}$ of 0.5±0.0 h, half-life (T v2) of 1.66±1.0 h, and $C_{max}$ of 4.56±0.77 μM.

FIG. 36 shows an oral formulation of AVR-84 (compound 17) was prepared and dosed to adult rats (n=3) at 100 mg/kg dose. The plasma showed linear decline in drug concentration, with $T_{max}$ of 0.5±0.0 h, half-life (T v2) of 1.66±1.0 h, and $C_{max}$ of 4.56±0.77 04.

It is contemplated that any embodiment discussed in this specification can be implemented with respect to any method, kit, reagent, or composition of the invention, and vice versa. Furthermore, compositions of the invention can be used to achieve the methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES—EXAMPLE 1

Abdullah, O. M., T. Seidel, M. Dahl, A. D. Gomez, G. Yiep, J. Cortino, F. B. Sachse, K. H. Albertine and E. W. Hsu (2016). "Diffusion tensor imaging and histology of developing hearts." NMR Biomed 29(10): 1338-1349.

Albertine, K. H. (2012). "Brain injury in chronically ventilated preterm neonates: collateral damage related to ventilation strategy." Clin Perinatol 39(3): 727-740.

Albertine, K. H., M. J. Dahl, L. W. Gonzales, Z. M. Wang, D. Metcalfe, D. M. Hyde, C. G. Plopper, B. C. Starcher, D. P. Carlton and R. D. Bland (2010). "Chronic lung disease in preterm lambs: effect of daily vitamin A treatment on alveolarization." Am J Physiol Lung Cell Mol Physiol 299(1): L59-72.

Albertine, K. H., G. P. Jones, B. C. Starcher, J. F. Bohnsack, P. L. Davis, S. C. Cho, D. P. Carlton and R. D. Bland (1999). "Chronic lung injury in preterm lambs. Disordered respiratory tract development." Am J Respir Crit Care Med 159(3): 945-958.

Dahl, M. J., S. Bowen, T. Aoki, A. Rebentisch, E. Dawson, L. Pettet, H. Emerson, B. Yu, Z. Wang, H. Yang, C. Zhang, A. P. Presson, L. Joss-Moore, D. M. Null, B. A. Yoder and K. H. Albertine (2018). "Former-preterm lambs have persistent alveolar simplification at 2 and 5 months corrected postnatal age." Am J Physiol Lung Cell Mol Physiol 315(5): L816-1833.

Joss-Moore, L. A., D. B. Metcalfe, K. H. Albertine, R. A. McKnight and R. H. Lane (2010). "Epigenetics and fetal adaptation to perinatal events: diversity through fidelity." J Anim Sci 88 (13 Suppl): E216-222.

Kadam, S. D., A. M. White, K. J. Staley and F. E. Dudek (2010). "Continuous electroencephalographic monitoring with radio-telemetry in a rat model of perinatal hypoxia-ischemia reveals progressive post-stroke epilepsy." J Neurosci 30(1): 404-415.

Null, D. M., J. Alvord, W. Leavitt, A. Wint, M. J. Dahl, A. P. Presson, R. H. Lane, R. J. DiGeronimo, B. A. Yoder and K. H. Albertine (2014). "High-frequency nasal ventilation for 21 d maintains gas exchange with lower respiratory pressures and promotes alveolarization in preterm lambs." Pediatr Res 75(4): 507-516.

Pierce, R. A., K. H. Albertine, B. C. Starcher, J. F. Bohnsack, D. P. Carlton and R. D. Bland (1997). "Chronic lung injury in preterm lambs: disordered pulmonary elastin deposition." Am J Physiol 272 (3 Pt 1): L452-460.

Reyburn, B., M. Li, D. B. Metcalfe, N. J. Kroll, J. Alvord, A. Wint, M. J. Dahl, J. Sun, L. Dong, Z. M. Wang, C. Callaway, R. A. McKnight, L. Moyer-Mileur, B. A. Yoder, D. M. Null, R. H. Lane and K. H. Albertine (2008). "Nasal ventilation alters mesenchymal cell turnover and improves alveolarization in preterm lambs." Am J Respir Crit Care Med 178(4): 407-418.

Roberts, J. K., C. Stockmann, M. J. Dahl, K. H. Albertine, E. Egan, Z. Lin, C. A. Reilly, P. L. Ballard, R. A. Ballard and R. M. Ward (2016). "Pharmacokinetics of Budesonide Administered with Surfactant in Premature Lambs: Implications for Neonatal Clinical Trials." Curr Clin Pharmacol 11(1): 53-61.

Visconti, K., P. Senthamaraikannan, M. W. Kemp, M. Saito, B. W. Kramer, J. P. Newnham, A. H. Jobe and S. G. Kallapur (2018). "Extremely preterm fetal sheep lung responses to antenatal steroids and inflammation." Am J Obstet Gynecol 218(3): 349.e341-349.e310.

REFERENCES—EXAMPLE 2

Nature Scientific Report, 2019 Feb. 27; 9(1):2904

U. S. Pat Publication 20200022995.

J infect dis, 2010, 202, 1754-1763.

Abdullah, O. M., T. Seidel, M. Dahl, A. D. Gomez, G. Yiep, J. Cortino, F. B. Sachse, K. H. Albertine and E. W. Hsu (2016). "Diffusion tensor imaging and histology of developing hearts." NMR Biomed 29(10): 1338-1349.

Abman, S. H. (2010). "Impaired vascular endothelial growth factor signaling in the pathogenesis of neonatal pulmonary vascular disease." Adv Exp Med Biol 661: 323-335.

Aghai, Z. H., S. Faqiri, J. G. Saslow, T. Nakhla, S. Farhath, A. Kumar, R. Eydelman, L. Strande, G. Stahl, P. Leone and V. Bhandari (2008). "Angiopoietin 2 concentrations in infants developing bronchopulmonary dysplasia: attenuation by dexamethasone." J Perinatol 28(2): 149-155.

Albertine, K. H. (2012). "Brain injury in chronically ventilated preterm neonates: collateral damage related to ventilation strategy." Clin Perinatol 39(3): 727-740.

Albertine, K. H., M. J. Dahl, L. W. Gonzales, Z. M. Wang, D. Metcalfe, D. M. Hyde, C. G. Plopper, B. C. Starcher, D. P. Carlton and R. D. Bland (2010). "Chronic lung disease in preterm lambs: effect of daily vitamin A treatment on alveolarization." Am J Physiol Lung Cell Mol Physiol 299(1): L59-72.

Albertine, K. H., G. P. Jones, B. C. Starcher, J. F. Bohnsack, P. L. Davis, S. C. Cho, D. P. Carlton and R. D. Bland (1999). "Chronic lung injury in preterm lambs. Disordered respiratory tract development." Am J Respir Crit Care Med 159(3): 945-958.

Alejandre-Alcazar, M. A., G. Kwapiszewska, I. Reiss, O. V. Amarie, L. M. Marsh, J. Sevilla-Perez, M. Wygrecka, B. Eul, S. Kobrich, M. Hesse, R. T. Schermuly, W. Seeger, O. Eickelberg and R. E. Morty (2007). "Hyperoxia modulates TGF-beta/BMP signaling in a mouse model of bronchopulmonary dysplasia." Am J Physiol Lung Cell Mol Physiol 292(2): L537-549.

Andrews, E. a. S., A (2020). "Is inhaled budesonide a useful adjunct for the prevention or management of bronchopulmonary dysplasia?" Arch Dis Child 105: 508-511.

Bassler, D. (2017). "Inhaled budesonide for the prevention of bronchopulmonary dysplasia." J Matern Fetal Neonatal Med 30(19): 2372-2374.

Bassler, D., H. L. Halliday, R. Plavka, M. Hallman, E. S. Shinwell, P. H. Jarreau, V. Carnielli, J. van den Anker, M. Schwab and C. F. Poets (2010). "The Neonatal European Study of Inhaled Steroids (NEUROSIS): an eu-funded international randomised controlled trial in preterm infants." Neonatology 97(1): 52-55.

Bassler, D., E. S. Shinwell, M. Hallman, P. H. Jarreau, R. Plavka, V. Carnielli, C. Meisner, C. Engel, A. Koch, K. Kreutzer, J. N. van den Anker, M. Schwab, H. L. Halliday, C. F. Poets and G. Neonatal European Study of Inhaled Steroids Trial (2018). "Long-Term Effects of Inhaled Budesonide for Bronchopulmonary Dysplasia." N Engl J Med 378(2): 148-157.

Bhandari, V. (2002). "Developmental differences in the role of interleukins in hyperoxic lung injury in animal models." Front Biosci 7: d1624-1633.

Bhandari, V. (2014). "Drug therapy trials for the prevention of bronchopulmonary dysplasia: current and future targets." Front Pediatr 2: 76.

Bhandari, V. (2016). Bronchopulmonary Dysplasia.

Bhandari, V., R. Choo-Wing, C. G. Lee, K. Yusuf, J. H. Nedrelow, N. Ambalavanan, H. Malkus, R. J. Homer and J. A. Elias (2008). "Developmental regulation of NO-mediated VEGF-induced effects in the lung." Am J Respir Cell Mol Biol 39(4): 420-430.

Bhandari, V., R. Choo-Wing, C. G. Lee, Z. Zhu, J. H. Nedrelow, G. L. Chupp, X. Zhang, M. A. Matthay, L. B. Ware, R. J. Homer, P. J. Lee, A. Geick, A. R. de Fougerolles and J. A. Elias (2006). "Hyperoxia causes angiopoietin 2-mediated acute lung injury and necrotic cell death." Nat Med 12(11): 1286-1293.

Bhandari, V. and J. A. Elias (2006). "Cytokines in tolerance to hyperoxia-induced injury in the developing and adult lung." Free Radic Biol Med 41(1): 4-18.

Chen, X., M. Orriols, F. J. Walther, E. H. Laghmani, A. M. Hoogeboom, A. C. B. Hogen-Esch, P. S. Hiemstra, G. Folkerts, M. T. H. Goumans, P. Ten Dijke, N. W. Morrell and G. T. M. Wagenaar (2017). "Bone Morphogenetic Protein 9 Protects against Neonatal Hyperoxia-Induced Impairment of Alveolarization and Pulmonary Inflammation." Front Physiol 8: 486.

Chen, Y., Q. Li, Y. Liu, L. Shu, N. Wang, Y. Wu, X. Sun and L. Wang (2015). "Attenuation of hyperoxia-induced lung injury in neonatal rats by 1alpha,25-Dihydroxyvitamin D3." Exp Lung Res 41(6): 344-352.

Curtale, G., M. Mirolo, T. A. Renzi, M. Rossato, F. Bazzoni and M. Locati (2013). "Negative regulation of Toll-like receptor 4 signaling by IL-10-dependent microRNA-146b." Proc Natl Acad Sci USA 110(28): 11499-11504.

Dahl, M. J., S. Bowen, T. Aoki, A. Rebentisch, E. Dawson, L. Pettet, H. Emerson, B. Yu, Z. Wang, H. Yang, C. Zhang, A. P. Presson, L. Joss-Moore, D. M. Null, B. A. Yoder and K. H. Albertine (2018). "Former-preterm lambs have persistent alveolar simplification at 2 and 5 months corrected postnatal age." Am J Physiol Lung Cell Mol Physiol 315(5): L816-1833.

Das, P., S. Acharya, D. Shah, B. Agarwal, V. Prahaladan and V. Bhandari (2020). "Chitin Analog AVR-25 Prevents Experimental Bronchopulmonary Dysplasia." J Pediatr Intensive Care 9(3): 225-232.

Das, P., T. Curstedt, B. Agarwal, V. M. Prahaladan, J. Ramirez, S. Bhandari, M. A. Syed, F. Salomone, C. Casiraghi, N. Pelizzi and V. Bhandari (2020). "Small Molecule Inhibitor Adjuvant Surfactant Therapy Attenuates Ventilator- and Hyperoxia-Induced Lung Injury in Preterm Rabbits." Front Physiol 11: 266.

De Paepe, M. E., L. C. Hanley, Z. Lacourse, T. Pasquariello and Q. Mao (2011). "Pulmonary dendritic cells in lungs of preterm infants: neglected participants in bronchopulmonary dysplasia?" Pediatr Dev Pathol 14(1): 20-27.

Filippone, M., D. Nardo, L. Bonadies, S. Salvadori and E. Baraldi (2019). "Update on Postnatal Corticosteroids to Prevent or Treat Bronchopulmonary Dysplasia." Am J Perinatol 36 (S 02): S58-S62.

Gilfillan, M., P. Das, D. Shah, M. A. Alam and V. Bhandari (2020). "Inhibition of microRNA-451 is associated with increased expression of Macrophage Migration Inhibitory Factor and mitgation of the cardio-pulmonary phenotype in a murine model of Bronchopulmonary Dysplasia." Respir Res 21(1): 92.

Hansmann, G., H. Sallmon, C. C. Roehr, S. Kourembanas, E. D. Austin, M. Koestenberger and N. European Pediatric Pulmonary Vascular Disease (2021). "Pulmonary hypertension in bronchopulmonary dysplasia." Pediatr Res 89(3): 446-455.

Horbar, J. D., E. M. Edwards, L. T. Greenberg, K. A. Morrow, R. F. Soll, M. E. Buus-Frank and J. S. Buzas (2017). "Variation in Performance of Neonatal Intensive Care Units in the United States." JAMA Pediatr 171(3): e164396.

Janes, K. A., M. P. Fresneau, A. Marazuela, A. Fabra and M. a. J. Alonso (2001). "Chitosan nanoparticles as delivery systems for doxorubicin." Journal of Controlled Release 73(2-3): 255-267.

Jensen, E. A., R. S. Roberts and B. Schmidt (2020). "Drugs to Prevent Bronchopulmonary Dysplasia: Effect of Baseline Risk on the Number Needed to Treat." J Pediatr 222: 244-247.

Joss-Moore, L. A., D. B. Metcalfe, K. H. Albertine, R. A. McKnight and R. H. Lane (2010). "Epigenetics and fetal adaptation to perinatal events: diversity through fidelity." J Anim Sci 88 (13 Suppl): E216-222.

Jung, Y. H., J. Jang, H.-S. Kim, S. H. Shin, C. W. Choi, E.-K. Kim and B. I. Kim (2019). "Respiratory severity score as a predictive factor for severe bronchopulmonary dysplasia or death in extremely preterm infants." BMC Pediatrics 19(1): 121.

Kim, H. M., B. S. Park, J.-I. Kim, S. E. Kim, J. Lee, S. C. Oh, P. Enkhbayar, N. Matsushima, H. Lee, O. J. Yoo and J.-O. Lee (2007). "Crystal Structure of the TLR4-MD-2 Complex with Bound Endotoxin Antagonist Eritoran." Cell 130(5): 906-917.

Leary, S., P. Das, D. Ponnalagu, H. Singh and V. Bhandari (2019). "Genetic Strain and Sex Differences in a Hyperoxia-Induced Mouse Model of Varying Severity of Bronchopulmonary Dysplasia." Am J Pathol 189(5): 999-1014.

Li, N., C. Zhuang, M. Wang, X. Sun, S. Nie and W. Pan (2009). "Liposome coated with low molecular weight chitosan and its potential use in ocular drug delivery." International Journal of Pharmaceutics 379(1): 131-138.

Liu, Y., P. Jiang, M. Du, K. Chen, A. Chen, Y. Wang, F. Cao, S. Deng and Y. Xu (2015). "Hyperoxia-induced immature brain injury through the TLR4 signaling pathway in newborn mice." Brain Res 1610: 51-60.

Lui, K., S. K. Lee, S. Kusuda, M. Adams, M. Vento, B. Reichman, B. A. Darlow, L. Lehtonen, N. Modi, M. Norman, S. Hakansson, D. Bassler, F. Rusconi, A. Lodha, J. Yang, P. S. Shah and I. International Network for Evaluation of Outcomes of neonates (2019). "Trends in Outcomes for Neonates Born Very Preterm and Very Low Birth Weight in 11 High-Income Countries." J Pediatr 215: 32-40 e14.

Meau-Petit, V., G. Thouvenin, N. Guillemot-Lambert, V. Champion, I. Tillous-Borde, F. Flamein, L. de Saint Blanquat, S. Essouri, J. Guilbert, N. Nathan, I. Guellec, S. Kout, R. Epaud and M. Levy (2013). "[Bronchopulmonary dysplasia-associated pulmonary arterial hypertension of very preterm infants]." Arch Pediatr 20(1): 44-53.

Null, D. M., J. Alvord, W. Leavitt, A. Wint, M. J. Dahl, A. P. Presson, R. H. Lane, R. J. DiGeronimo, B. A. Yoder and K. H. Albertine (2014). "High-frequency nasal ventilation for 21 d maintains gas exchange with lower respiratory pressures and promotes alveolarization in preterm lambs." Pediatr Res 75(4): 507-516.

Panda, S. K., S. Kumar, N. C. Tupperwar, T. Vaidya, A. George, S. Rath, V. Bal and B. Ravindran (2012). "Chitohexaose activates macrophages by alternate pathway through TLR4 and blocks endotoxemia." PLoS Pathog 8(5): e1002717.

Pierce, R. A., K. H. Albertine, B. C. Starcher, J. F. Bohnsack, D. P. Carlton and R. D. Bland (1997). "Chronic lung injury in preterm lambs: disordered pulmonary elastin deposition." Am J Physiol 272 (3 Pt 1): L452-460.

Potter, C. F., N. T. Kuo, C. F. Farver, J. T. McMahon, C. H. Chang, F. H. Agani, M. A. Haxhiu and R. J. Martin (1999). "Effects of hyperoxia on nitric oxide synthase expression, nitric oxide activity, and lung injury in rat pups." Pediatr Res 45(1): 8-13.

Reyburn, B., M. Li, D. B. Metcalfe, N. J. Kroll, J. Alvord, A. Wint, M. J. Dahl, J. Sun, L. Dong, Z. M. Wang, C. Callaway, R. A. McKnight, L. Moyer-Mileur, B. A. Yoder, D. M. Null, R. H. Lane and K. H. Albertine (2008). "Nasal ventilation alters mesenchymal cell turnover and improves alveolarization in preterm lambs." Am J Respir Crit Care Med 178(4): 407-418.

Sahni, M. and V. Bhandari (2020). "Recent advances in understanding and management of bronchopulmonary dysplasia." F1000Res 9.

Sahni, M., B. Yeboah, P. Das, D. Shah, D. Ponnalagu, H. Singh, L. D. Nelin and V. Bhandari (2020). "Novel biomarkers of bronchopulmonary dysplasia and bronchopulmonary dysplasia-associated pulmonary hypertension." J Perinatol 40(11): 1634-1643.

Shah, D., P. Das, S. Acharya, B. Agarwal, D. J. Christensen, S. M. Robertson and V. Bhandari (2021). "Small Immunomodulatory Molecules as Potential Therapeutics in Experimental Murine Models of Acute Lung Injury (ALI)/Acute Respiratory Distress Syndrome (ARDS)." Int J Mol Sci 22(5).

Speer, C. P. (2006). "Pulmonary inflammation and bronchopulmonary dysplasia." J Perinatol 26 Suppl 1: S57-62; discussion S63-54.

Stenmark, K. R. and S. H. Abman (2005). "Lung vascular development: implications for the pathogenesis of bronchopulmonary dysplasia." Annu Rev Physiol 67: 623-661.

Strueby, L. and B. Thebaud (2018). "Novel therapeutics for bronchopulmonary dysplasia." Curr Opin Pediatr 30(3): 378-383.

Suchismita Acharya, P. D., Beamon Agarwal (2020). Novel Immunodulating Small Molecules, AyuVis Research Inc.

Sun, H., R. Choo-Wing, A. Sureshbabu, J. Fan, L. Leng, S. Yu, D. Jiang, P. Noble, R. J. Homer, R. Bucala and V. Bhandari (2013). "A critical regulatory role for macrophage migration inhibitory factor in hyperoxia-induced injury in the developing murine lung." PLoS One 8(4): e60560.

Sun, Y., C. Chen, X. Zhang, X. Weng, A. Sheng, Y. Zhu, S. Chen, X. Zheng and C. Lu (2019). "High Neutrophil-to-Lymphocyte Ratio Is an Early Predictor of Bronchopulmonary Dysplasia." Front Pediatr 7: 464.

Sureshbabu, A., M. Syed, P. Das, C. Janer, G. Pryhuber, A. Rahman, S. Andersson, R. J. Homer and V. Bhandari (2016). "Inhibition of Regulatory-Associated Protein of Mechanistic Target of Rapamycin Prevents Hyperoxia-Induced Lung Injury by Enhancing Autophagy and Reducing Apoptosis in Neonatal Mice." Am J Respir Cell Mol Biol 55(5): 722-735.

Syed, M., P. Das, A. Pawar, Z. H. Aghai, A. Kaskinen, Z. W. Zhuang, N. Ambalavanan, G. Pryhuber, S. Andersson and V. Bhandari (2017). "Hyperoxia causes miR-34a-mediated injury via angiopoietin-1 in neonatal lungs." Nat Commun 8(1): 1173.

Tam, J. S. Y., J. K. Coller, P. A. Hughes, C. A. Prestidge and J. M. Bowen (2021). "Toll-like receptor 4 (TLR4) antagonists as potential therapeutics for intestinal inflammation." Indian J Gastroenterol.

Thebaud, B., K. N. Goss, M. Laughon, J. A. Whitsett, S. H. Abman, R. H. Steinhorn, J. L. Aschner, P. G. Davis, S. A. McGrath-Morrow, R. F. Soll and A. H. Jobe (2019). "Bronchopulmonary dysplasia." Nat Rev Dis Primers 5(1): 78.

Tolia, V. N., K. Murthy, P. S. McKinley, M. M. Bennett and R. H. Clark (2014). "The effect of the national shortage of vitamin A on death or chronic lung disease in extremely low-birth-weight infants." JAMA Pediatr 168(11): 1039-1044.

Williams, J., R. Lansdown, R. Sweitzer, M. Romanowski, R. LaBell, R. Ramaswami and E. Unger (2003). "Nanoparticle drug delivery system for intravenous delivery of topoisomerase inhibitors." Journal of Controlled Release 91(1-2): 167-172.
Yee, M., R. J. White, H. A. Awad, W. A. Bates, S. A. McGrath-Morrow and M. A. O'Reilly (2011). "Neonatal hyperoxia causes pulmonary vascular disease and shortens life span in aging mice." Am J Pathol 178(6): 2601-2610.

What is claimed is:

1. A method for preventing at least one of: neonatal lung injury, bronchopulmonary dysplasia (BPD), or BPD-associated pulmonary hypertension (BPD-PH), comprising:

administering to the subject in need thereof a therapeutically effective amount of a lung surfactant isolated from a lung extract or a synthetic equivalent thereof; and a compound of formula (I) or stereoisomer, enantiomer, tautomer or a pharmaceutically acceptable salt thereof:

Formula-I

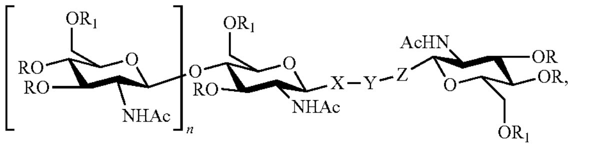

wherein X=O; Y=Phenyl, a phenyl group substituted with at least one methyl, a phenyl group substituted with at least one nitro, a phenyl group substituted with at least one nitrogen containing group, a phenyl group substituted with at least one boron containing group; Z=none; R=H, C(O)$R_2$, $SO_2R_2$; $R_1$=H, C(O)$R_2$, $SO_2R_2$; $R_2$=ethyl, methyl, isopropyl, n-propyl, t-butyl, n-butyl, $NH_2$, $NR_3R_4$; $R_3$, $R_4$=ethyl, methyl, isopropyl, n-propyl, t-butyl, n-butyl, three to six membered cycloalkyl, wherein an amount of the compound is selected to prevent the at least one of: neonatal lung injury, bronchopulmonary dysplasia (BPD), or BPD-associated pulmonary hypertension (BPD-PH), wherein the compound of formula (I) is provided in an amount of about 0.5 to 100 mg/kg that is synergistic with the lung surfactant.

2. The method of claim 1, wherein the compound of formula (I) is formulated into a pharmaceutical composition comprising one or more pharmaceutically acceptable excipients, buffers, or salts.

3. The method of claim 1, wherein the compound of formula (I) is formulated into a pharmaceutical composition adapted for pulmonary, alveolar, enteral, parenteral, intravenous, topical, or oral administration.

4. The method of claim 1, wherein the compound of formula (I) is formulated into an aerosol, a nebulizer, or an inhaler.

5. The method of claim 1, wherein the compound of formula (I) forms an inhalation dosage form.

6. The method of claim 1, further comprising adding one or more liposomes, polymers, salts, or buffers.

7. The method of claim 1, further comprising adding one or more additional therapeutic agent selected from the group consisting of corticosteroids, bronchodilators, anticholinergics, vasodilators, diuretics, anti-hypertensive agents, acetazolamide, antibiotics, antivirals, immunosuppressive drugs, and surfactants.

8. The method of claim 1, wherein the compound of formula (I) is provided in an amount that competitively inhibits inflammation and modulates macrophages to protect lung tissue damage or limit lung tissue injury.

9. The method of claim 1, wherein the subject is a pediatric or adult human or a pediatric or adult animal.

10. The method of claim 1, wherein the compound of formula (I) is formulated for a delivery device that is a spray device or a pressurized delivery device.

11. The method of claim 1, wherein the compound of formula I is:

8

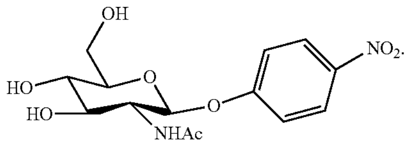

12. A method for preventing at least one of: neonatal lung injury, bronchopulmonary dysplasia (BPD), or BPD-associated pulmonary hypertension (BPD-PH), comprising:

administering to the subject in need thereof a therapeutically effective amount of a lung surfactant isolated from a lung extract or a synthetic equivalent thereof; and a compound or stereoisomer, enantiomer, tautomer or a pharmaceutically acceptable salt thereof, selected from:

1

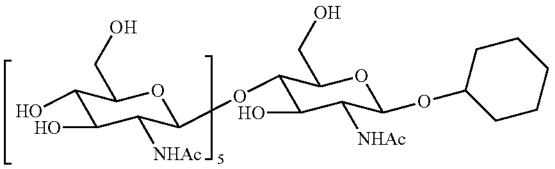

2

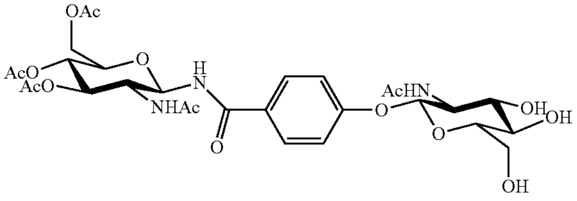

3

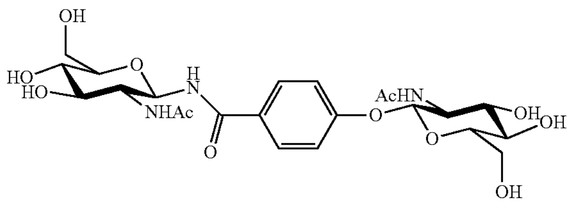

-continued
4
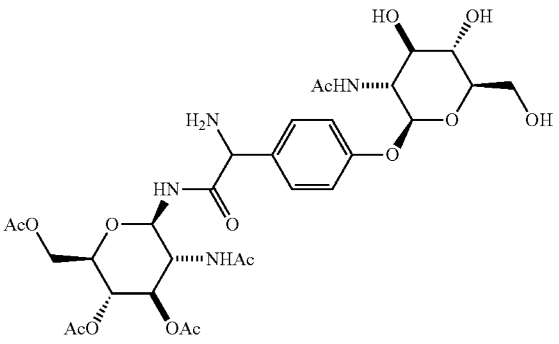
5
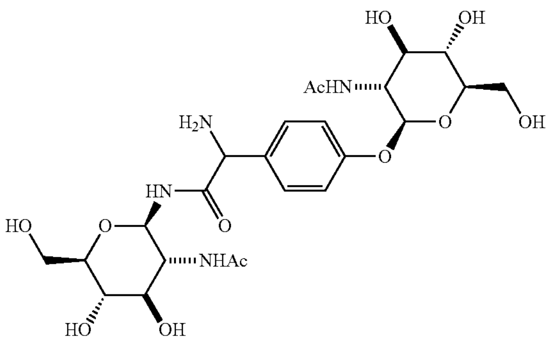
6
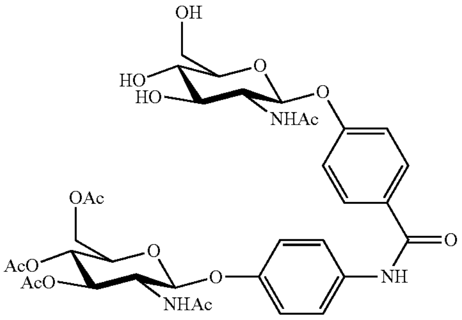
7
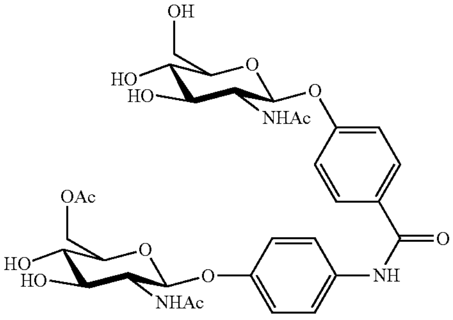
9
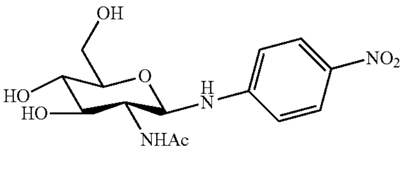
-continued
10
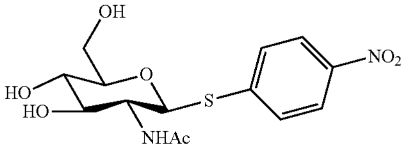
11
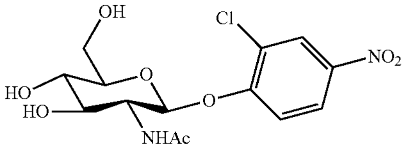
12
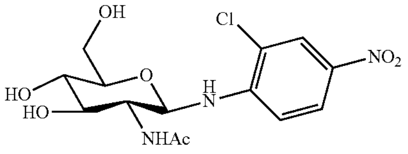
13
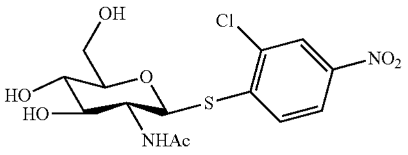
14
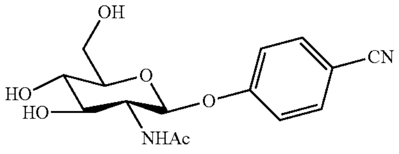
15
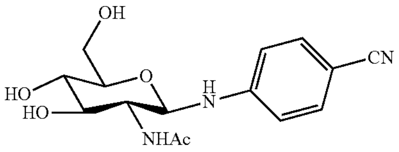
16
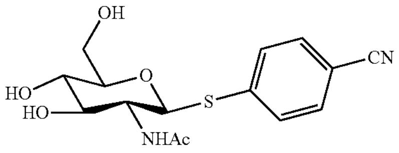
17
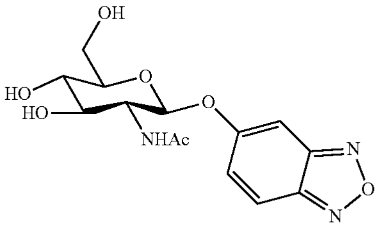
18
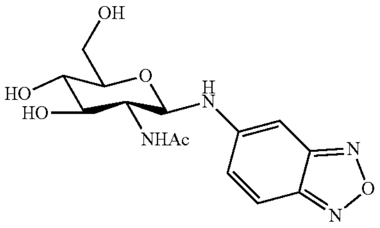

-continued
19
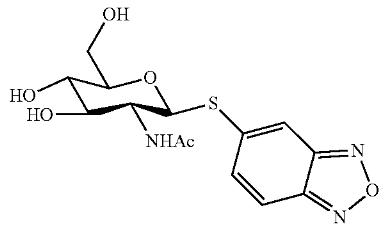
20
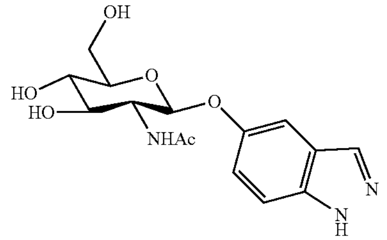
21
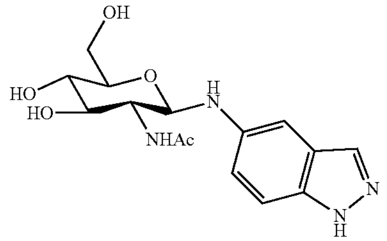
22
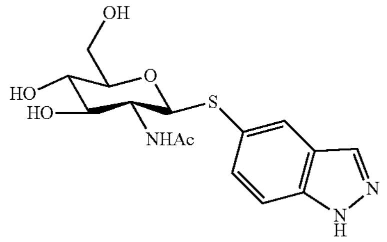
23
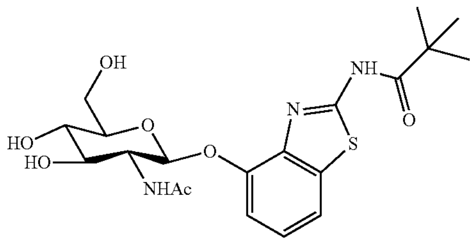
24
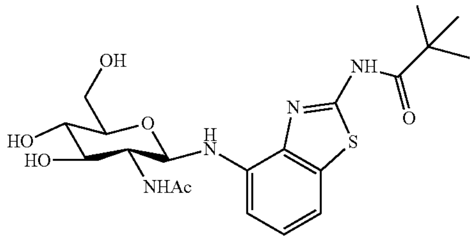
-continued
25
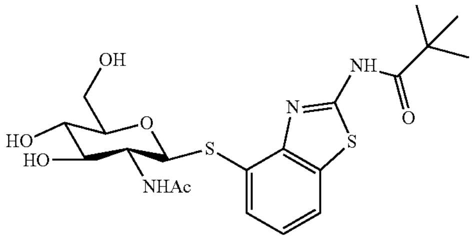
26
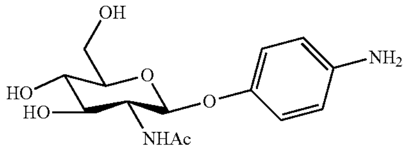
27
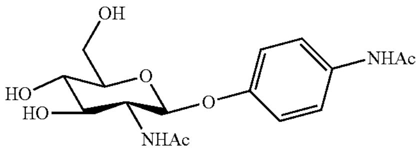
29
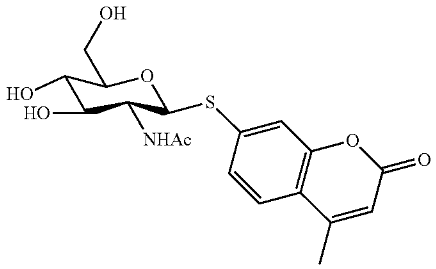
28
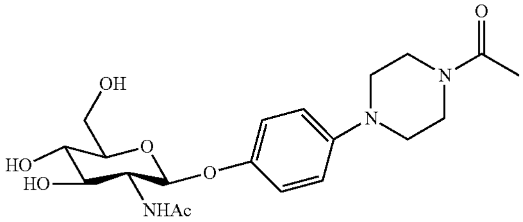
30
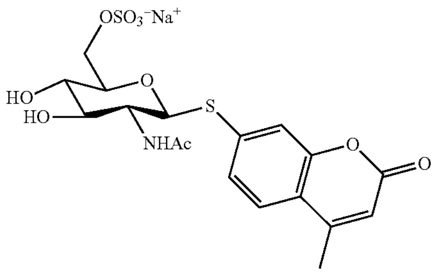
31
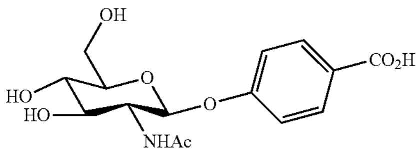

-continued

32

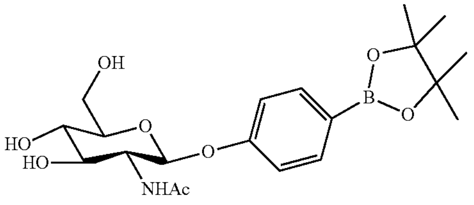

33

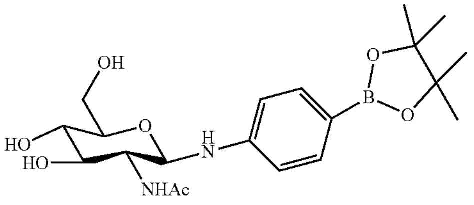

34

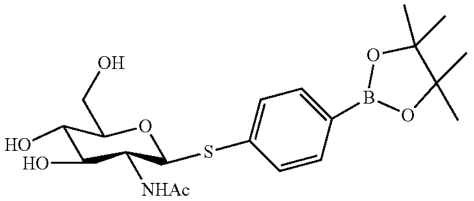

35

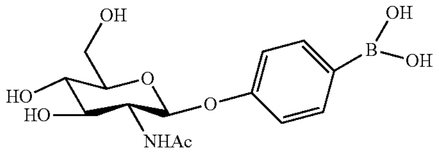

36

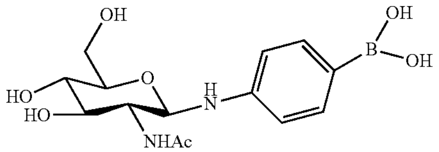

37

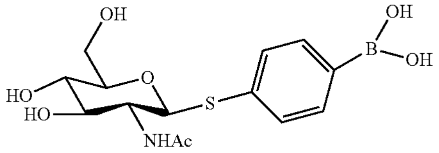

38

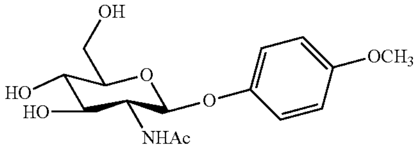

39

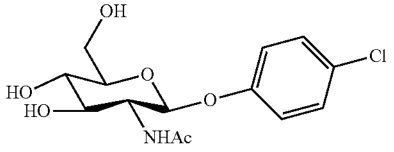

or

40

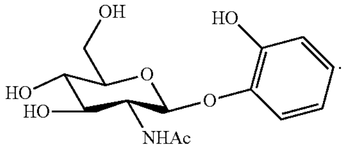

13. The method of claim 1, further comprising the step of identifying a subject in need of treatment for a pulmonary inflammation, distress or insufficiency prior to the treatment.

14. The method of claim 1, wherein the compound of formula (I) is provided in an amount of about 1 mg/kg.

15. The method of claim 1, wherein the compound of formula (I) is provided in an amount of about 2 mg/kg.

16. The method of claim 1, wherein the compound of formula (I) is provided in an amount of about 3 mg/kg.

17. The method of claim 1, wherein the compound of formula (I) is provided in an amount of about 5 mg/kg.

18. The method of claim 1, wherein the compound of formula (I) is provided in an amount of about 10 mg/kg.

19. A method for preventing at least one of: neonatal lung injury, bronchopulmonary dysplasia (BPD), or BPD-associated pulmonary hypertension (BPD-PH), comprising:

administering to the subject in need thereof a therapeutically effective amount of a lung surfactant isolated from a lung extract or a synthetic equivalent thereof; and a compound of formula (I) or stereoisomer, enantiomer, tautomer or a pharmaceutically acceptable salt thereof:

8

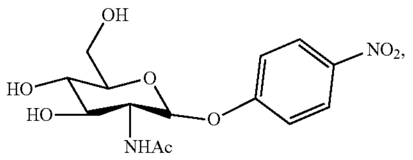

wherein an amount of the compound is selected to prevent the at least one of: neonatal lung injury, bronchopulmonary dysplasia (BPD), or BPD-associated pulmonary hypertension (BPD-PH), wherein the compound of formula (I) is provided in an amount of about 0.5 to 100 mg/kg that is synergistic with the lung surfactant.

20. The method of claim 19, wherein the compound of formula (I) is formulated into a pharmaceutical composition comprising one or more pharmaceutically acceptable excipients, buffers, or salts.

21. The method of claim 19, wherein the compound of formula (I) is formulated into a pharmaceutical composition adapted for pulmonary, alveolar, enteral, parenteral, intravenous, topical, or oral administration.

22. The method of claim 19, wherein the compound of formula (I) is formulated into an aerosol, a nebulizer, or an inhaler.

23. The method of claim 19, wherein the compound of formula (I) forms an inhalation dosage form.

24. The method of claim 19, further comprising adding one or more liposomes, polymers, salts, or buffers.

25. The method of claim 19, further comprising adding one or more additional therapeutic agents selected from the group consisting of corticosteroids, bronchodilators, anticholinergics, vasodilators, diuretics, anti-hypertensive agents, acetazolamide, antibiotics, antivirals, immunosuppressive drugs, and surfactants.

26. The method of claim 19, wherein the compound of formula (I) is provided in an amount that competitively inhibits inflammation and modulates macrophages to protect lung tissue damage or limit lung tissue injury.

27. The method of claim 19, wherein the subject is a pediatric or adult human or a pediatric or adult animal.

28. The method of claim 19, wherein the compound of formula (I) is formulated for a delivery device that is a spray device or a pressurized delivery device.

29. The method of claim 19, wherein the compound of formula (I) is provided in an amount of about 1 mg/kg.

30. The method of claim 19, wherein the compound of formula (I) is provided in an amount of about 2 mg/kg.

31. The method of claim 19, wherein the compound of formula (I) is provided in an amount of about 3 mg/kg.

32. The method of claim 19, wherein the compound of formula (I) is provided in an amount of about 5 mg/kg.

33. The method of claim 19, wherein the compound of formula (I) is provided in an amount of about 10 mg/kg.

34. The method of claim 12, further comprising the step of identifying a subject in need of treatment for a pulmonary inflammation, distress or insufficiency prior to the treatment.

35. The method of claim 12, wherein the compound is provided in an amount of about 1 mg/kg.

36. The method of claim 12, wherein the compound is provided in an amount of about 2 mg/kg.

37. The method of claim 12, wherein the compound is provided in an amount of about 3 mg/kg.

38. The method of claim 12, wherein the compound is provided in an amount of about 5 mg/kg.

39. The method of claim 12, wherein the compound is provided in an amount of about 10 mg/kg.

* * * * *